(12) United States Patent
Tanokura et al.

(10) Patent No.: US 12,227,563 B2
(45) Date of Patent: Feb. 18, 2025

(54) ANTI-IGF-I RECEPTOR HUMANIZED ANTIBODY

(71) Applicant: Teijin Pharma Limited, Tokyo (JP)

(72) Inventors: Akira Tanokura, Tokyo (JP); Hirotsugu Kato, Tokyo (JP); Hiroshi Eguchi, Tokyo (JP); Kenichiro Takagi, Tokyo (JP); Satoshi Yamamura, Tokyo (JP); Naoko Namiki, Tokyo (JP); Daisuke Ishikawa, Kikuchi (JP); Hirofumi Higuchi, Kikuchi (JP); Tomoyo Takeo, Kikuchi (JP); Masayo Ohori, Kikuchi (JP)

(73) Assignee: Teijin Pharma Limited, Tokyo (JP)

( * ) Notice: Subject to any disclaimer, the term of this patent is extended or adjusted under 35 U.S.C. 154(b) by 430 days.

(21) Appl. No.: 17/299,383

(22) PCT Filed: Dec. 2, 2019

(86) PCT No.: PCT/JP2019/047050
§ 371 (c)(1),
(2) Date: Jun. 3, 2021

(87) PCT Pub. No.: WO2020/116398
PCT Pub. Date: Jun. 11, 2020

(65) Prior Publication Data
US 2022/0033485 A1 Feb. 3, 2022

(30) Foreign Application Priority Data
Dec. 3, 2018 (JP) ................................. 2018-226669

(51) Int. Cl.
| | |
|---|---|
| A61K 39/00 | (2006.01) |
| A61P 3/10 | (2006.01) |
| C07K 16/22 | (2006.01) |
| C12N 5/077 | (2010.01) |

(52) U.S. Cl.
CPC ............... *C07K 16/22* (2013.01); *A61P 3/10* (2018.01); *C12N 5/0658* (2013.01); *C07K 2317/24* (2013.01); *C07K 2317/565* (2013.01)

(58) Field of Classification Search
None
See application file for complete search history.

(56) References Cited

U.S. PATENT DOCUMENTS

| | | |
|---|---|---|
| 2003/0235582 A1 | 12/2003 | Singh et al. |
| 2004/0086503 A1 | 5/2004 | Cohen et al. |
| 2009/0253628 A1 | 10/2009 | Holtmann et al. |
| 2009/0265797 A1 | 10/2009 | Goetsch et al. |
| 2020/0115460 A1 | 4/2020 | Eguchi et al. |

FOREIGN PATENT DOCUMENTS

| | | |
|---|---|---|
| JP | 2004-531217 A | 10/2004 |
| JP | 2005-533493 A | 11/2005 |
| JP | 2009-502129 A | 1/2009 |
| JP | 2011-518778 A | 6/2011 |
| WO | 2018/221521 A1 | 12/2018 |

OTHER PUBLICATIONS

Edwards et al. (J. Mol. Biol. 334: 103-118, 2003).*
Torres et al. (Trends in Immunol. 29(2): 91-97, 2008).*
Khan et al. (J. Immunol. 192: 5398-5405, 2014).*
Poosarla et al. (Biotech. Bioengineer. 124(6): 1331-1342, 2017).*
Paul, Fundamental Immunology, 3rd Edition, 1993, pp. 292-295, under the heading "Fv Structure and Diversity in Three Dimensions".*
Rudikoff et al. (PNAS 79: 1979-1983, 1982).*
Maccallum, et al. (J. Mol. Biol. 262: 732-745, 1996).*
De Pacalis et al. (J. Immunol. 169: 3076-3084, 2002).*
Casset et al. (Biochem. Biophys. Res. Comm. 307: 198-205, 2003).*
Chen et al. (J. Mol. Biol. 293: 865-881, 1999).*
Wu et al. (J. Mol. Biol. 294: 151-162, 1999).*
Ohlsson, C. et al., "The role of liver-derived insulin-like growth factor-I", Endocr Rev, 2009. 30(5): pp. 494-535 (16 pages total).
Kavran, J.M. et al., "How IGF-I activates its receptor", Elife, 2014. 3. (28 pages total).
Bailyes, E.M. et al., "Insulin receptor/IGF-I receptor hybrids are widely distributed in mammalian tissues: quantification of individual receptor species by selective immunoprecipitation and immunoblotting", Biochem J, 1997, vol. 327 ( Pt 1): pp. 209-215 (7 pages total).
Pandini, G. et al., "Insulin/insulin-like growth factor I hybrid receptors have different biological characteristics depending on the insulin receptor isoform involved", J Biol Chem, 2002. 277(42): pp. 39684-39695 (13 pages total).
"Highlights of Prescribing Information", Somazon IF. 2015 (84 pages total).
Fukushima, T. et al., "Phosphatidylinositol 3-kinase (PI3K) activity bound to insulin-like growth factor-I (IGF-I) receptor, which is continuously sustained by IGF-I stimulation, is required for IGF-I-induced cell proliferation", J Biol Chem, 2012, vol. 287, No. 35, pp. 29713-29721(10 page total).
Schiaffino, S. and C. Mammucari, "Regulation of skeletal muscle growth by the IGF-I-Akt/PKB pathway: insights from genetic models", Skelet Muscle, 2011, vol. 1, No. 4 (14 pages total).
Boonen, S. et al., "Musculoskeletal effects of the recombinant human IGF-I/IGF binding protein-3 complex in osteoporotic patients with proximal femoral fracture: a double-blind, placebo-controlled pilot study", J Clin Endocrinol Metab, 2002. Vol. 87, No. 4, pp. 1593-1599 (7 pages total).

(Continued)

*Primary Examiner* — Christine J Saoud
(74) *Attorney, Agent, or Firm* — Sughrue Mion, PLLC

(57) ABSTRACT

Provided is a humanized antibody that, through IGF-I receptor, increases muscle mass but does not lower the blood glucose level. This humanized antibody: is an anti-IGF-I receptor humanized antibody, a fragment thereof, or a derivative thereof; has a specific amino acid sequence such as SEQ ID NOs: 1 to 6 serving as a CDR sequence; and specifically binds to IGF-I receptor extracellular domain.

6 Claims, 4 Drawing Sheets

Specification includes a Sequence Listing.

(56) References Cited

OTHER PUBLICATIONS

Barton-Davis, E.R. et al., "Viral mediated expression of insulin-like growth factor I blocks the aging-related loss of skeletal muscle function", Proc Natl Acad Sci USA, 1998. 95(26): pp. 15603-15607 (5 pages total).

Lamberts, S.W., A.W. van den Beld, and A.J. van der Lely, "The endocrinology of aging", Science, 1997, vol. 278, No. 5337, pp. 419-424 (7 pages total).

Musaro, A. et al., "Localized IGF-I transgene expression sustains hypertrophy and regeneration in senescent skeletal muscle", Nat Genet, 2001, vol. 27, No. 2, pp. 195-200 (6 pages total).

Temel, J.S. et al., "Anamorelin in patients with non-small-cell lung cancer and cachexia (ROMANA 1 and ROMANA 2): results from two randomized, double-blind, phase 3 trials", Lancet Oncol., 2016, vol. 17, No. 4, pp. 519-531 (13 pages total).

Glass, D.J., "Signaling pathways perturbing muscle mass", Curr Opin Clin Nutr Metab Care, 2010, vol. 13, No. 3, pp. 225-229 (5 pages total).

Lee, S.J. and A.C. McPherron, "Regulation of myostatin activity and muscle growth", Proc Natl Acad Sci U S A, 2001, vol. 98, No. 16, pp. 9306-9311 (6 pages total).

Amirouche, A. et al., "Down-regulation of Akt/mammalian target of rapamycin signaling pathway in response to myostatin overexpression in skeletal muscle", Endocrinology, 2009, vol. 150, No. 1, pp. 286-294 (9 pages total).

Woodhouse, L. et al., "A Phase 2 Randomized Study Investigating the Efficacy and Safety of Myostatin Antibody LY2495655 versus Placebo in Patients Undergoing Elective Total Hip Arthroplasty", Journal of Frailty & Aging, 2016, vol. 5, No. 1, pp. 62-70 (9 pages total).

Becker, C., et al., "Myostatin antibody (LY2495655) in older weak fallers: a proof-of-concept, randomized, phase 2 trial", Lancet Diabetes Endocrinol, 2015, vol. 3, No. 12, pp. 948-957 (10 pages total).

Amato, A.A. et al., "Treatment of sporadic inclusion body myositis with bimagrumab", Neurology, 2014, vol. 83, No. 24, pp. 2239-2246 (8 pages total).

Puche, J.E. and I. Castilla-Cortazar, "Human conditions of insulin-like growth factor-I (IGF-I) deficiency", Journal of Translational Medicine, 2012, vol. 10, No. 224 (29 pages total).

Kohn, A.D et al., "Expression of a constitutively active Akt Ser/Thr kinase in 3T3-L1 adipocytes stimulates glucose uptake and glucose transporter 4 translocation", Journal of Biol Chem, 1996, vol. 271, No. 49, pp. 31372-31378 (8 pages total).

Cho, H. et al., "Insulin resistance and a diabetes mellitus-like syndrome in mice lacking the protein kinase Akt2 (PKBB)", Science, 2001, vol. 292, No. 5522, pp. 1728-1731 (5 pages total).

Green, C.J. et al., "Use of Akt inhibitor and a drug-resistant mutant validates a critical role for protein kinase B/Akt in the insulin-dependent regulation of glucose and system A amino acid uptake", Journal of Biol. Chem., 2008, vol. 283, No. 41, pp. 27653-27667 (16 pages total).

"Center for Drug Evaluation and Research", FDA Application Material, Application No. 21-884, 2005 (108 pages total).

García-Fernández, M. et al., "Low doses of insulin-like growth factor I improve insulin resistance, lipid metabolism, and oxidative damage in aging rats", Endocrinology, 2008, vol. 149, No. 5, pp. 2433-2442 (10 pages total).

Puche, J.E. et al., "Low doses of insulin-like growth factor-I induce mitochondrial protection in aging rats", Endocrinology, 2008, vol. 149, No. 5, pp. 2620-2627 (8 pages total).

Joseph D'Ercole, A. and P. Ye, "Minireview: Expanding the mind: insulin-like growth factor I and brain development", Endocrinology, 2008, vol. 149, No. 12, pp. 5958-5962 (5 pages total).

Abuzzahab, M.J. et al., "IGF-I receptor mutations resulting in intrauterine and postnatal growth retardation", New England J. of Med, 2003, vol. 349, No. 23, pp. 2211-2222 (12 pages total).

Woods, K.A. et al., "Intrauterine growth retardation and postnatal growth failure associated with deletion of the insulin-like growth factor I gene", New England J. Med., 1996, vol. 335, No. 18, pp. 1363-1367 (5 pages total).

Pèrez, R., et al., "Mitochondrial protection by low doses of insulin-like growth factor-I in experimental cirrhosis", World J Gastroenterol, 2008, vol. 14, No. 17, pp. 2731-2739 (9 pages total).

Kang, B.P., et al., "IGF-I inhibits the mitochondrial apoptosis program in mesangial cells exposed to high glucose", Am J Physiol Renal Physiol, 2003, vol. 285, No. 5, pp. F1013-1024 (13 pages total).

Bhaskar, V. et al., "A fully human, allosteric monoclonal antibody that activates the insulin receptor and improves glycemic control", Diabetes, 2012, vol. 61, No. 5, pp. 1263-1271 (9 pages total).

Xiong, L. et al., "Growth-stimulatory monoclonal antibodies against human insulin-like growth factor I receptor", Proc. Natl. Acad.Sci. U S A, 1992, vol. 89, No. 12, pp. 5356-5360 (5 pages total).

Runnels, H.A. et al., "Human monoclonal antibodies to the insulin-like growth factor 1 receptor inhibit receptor activation and tumor growth in preclinical studies", Adv Ther, 2010, vol. 27, No. 7, pp. 458-475 (18 pages total).

Soos, M.A. et al., "A panel of monoclonal antibodies for the type I insulin-like growth factor receptor, Epitope mapping, effects on ligand binding, and biological activity", J Biol. Chem., 1992, vol. 267, No. 18, pp. 12955-12963 (9 pages total).

Kato, H. et al., "Role of tyrosine kinase activity in signal transduction by the insulin-like growth factor-I (IGF-I) receptor, Characterization of kinase-deficient IGF-I receptors and the action of an IGF-I-mimetic antibody (αIR-3)", J Biol. Chem., 1993, vol. 268, No. 4, pp. 2655-2661 (7 pages total).

Atzori, F. et al., "A Phase I Pharmacokinetic and Pharmacodynamic Study of Dalotuzumab (MK-0646), an Anti-Insulin-like Growth Factor-1 Receptor Monoclonal Antibody, in Patients with Advanced Solid Tumors", Clin. Cancer Res., 2011, vol. 17, No. 19, pp. 6304-6313 (10 pages total).

De Bono J. S. et al., "Phase II randomized study of figitumumab plus docetaxel and docetaxel alone with crossover for metastatic castration-resistant prostate cancer", Clin. Cancer Res., 2014, vol. 20, No. 7, pp. 1925-1934 (11 pages total).

* cited by examiner

FIG. 1

```
IGF1R_MOUSE    EMTNLKDIGLYNLRNITRGAIRIEKNADLCYLSTIDWSLILDAVSNNYIVGNKPPKECGD 180
IGF1R_RAT      EMTNLKDIGLYNLRNITRGAIRIEKNADLCYLSTIDWSLILDAVSNNYIVGNKPPKECGD 180
IGF1R_HUMAN    EMTNLKDIGLYNLRNITRGAIRIEKNADLCYLSTVDWSLILDAVSNNYIVGNKPPKECGD 180
IGF1R_CAVY     EMTNLKDIGLYNLRNITRGAIRIEKNADLCYLSTVDWSLILDAVSNNYIVGNKSPKECGD 180
IGF1R_RABIT    EMTNLKDIGLYNLRNITRGAIRIEKNADLCYLSTVDWSLILDAVSNNYIVGNKSPKECGD 180
               ****************************:*******************.******

IGF1R_MOUSE    LCPGTLEEKPMCEKTTINNEYNYRCWTTNRCQKMCPSVCGKRACTENNECCHPECLGSCH 240
IGF1R_RAT      LCPGTLEEKPMCEKTTINNEYNYRCWTTNRCQKMCPSVCGKRACTENNECCHPECLGSCH 240
IGF1R_HUMAN    LCPGTMEEKPMCEKTTINNEYNYRCWTTNRCQKMCPSTCGKRACTENNECCHPECLGSCS 240
IGF1R_CAVY     LCPGTMEEKPLCEKTTINNEYNYRCWTTNRCQKMCPSACGKRACTEYGECCHPECLGSCH 240
IGF1R_RABIT    MCPGTLEEKPLCEKTAINNEYNYRCWTTNRCQKMCPSACGKRACTENNECCHPECLGSCH 240
               :****:****:****:*****************.********  :***********

IGF1R_MOUSE    TPDDNTTCVACRHYYYKGVCVPACPPGTYRFEGWRCVDRDFCANIPNAESSDSDGFVIHD 300
IGF1R_RAT      TPDDNTTCVACRHYYYKGVCVPACPPGTYRFEGWRCVDRDFCANIPNAESSDSDGFVIHD 300
IGF1R_HUMAN    APDNDTACVACRHYYYAGVCVPACPPNTYRFEGWRCVDRDFCANILSAESSDSEGFVIHD 300
IGF1R_CAVY     APDDDTACVACRHFYYAGICVPACPPGTYRFEGWRCVHRDFCANIPNAESSDSEGFVIHD 300
IGF1R_RABIT    APDDDTACVACRHYYFSGVCVPACPPNTYRFEGWRCVDRDFCANIPNADGGDSEGFVIHD 300
               :**::*:******:*:* :*******.*********.*******  *: . **:******

IGF1R_MOUSE    QECMQECPSGFIRNSTQSMYCIPCEGPCPKVCGDEEKKTKTIDSVTSAQMLQGCTILKGN 360
IGF1R_RAT      QECMQECPSGFIRNSTQSMYCIPCEGPCPKVCGDEEKKTKTIDSVTSAQMLQGCTILKGN 360
IGF1R_HUMAN    GECMQECPSGFIRNGSQSMYCIPCEGPCPKVCE-EEKKTKTIDSVTSAQMLQGCTIFKGN 359
IGF1R_CAVY     GECMQECPSGFIRNGSQSMYCIPCEGPCPKVCE-EEKKTKTIDSVTSAQMLQGCTIFKGN 359
IGF1R_RABIT    GECMQECPSGFIRNGSQSMFCIPCEGPCPKVCE-EDKKTKTIDSVNSAQMLQGCTIFKGN 359
               .***********:.***:***************  *:********.**********:***
```

ANTI-IGF-I RECEPTOR HUMANIZED ANTIBODY

CROSS-REFERENCE TO RELATED APPLICATIONS

This application is a National Stage of International Application No. PCT/JP2019/047050 filed Dec. 2, 2019, which claims priority under U.S.C. § 119(a) to Japanese Patent Application No. JP2018-226669 filed on Dec. 3, 2018.

INCORPORATION BY REFERENCE OF SEQUENCE LISTING

The content of the electronically submitted sequence listing, file name: Q263951substitutesequencelistingasfiled; size: 103,413 bytes; and date of creation: Feb. 21, 2024, filed herewith, is incorporated herein by reference in its entirety.

TECHNICAL FIELD

The present invention relates to an anti-IGF-I receptor humanized antibody and, more specifically, to an anti-IGF-I receptor humanized antibody which specifically binds to an IGF-I receptor of a vertebrate.

BACKGROUND ART

1. IGF-I

IGF-I is an insulin-like growth factor secreted mainly from the liver through activation of a growth hormone (GH) receptor by the growth hormone secreted from the pituitary gland, and affects an IGF-I receptor to thereby express a variety of physiological functions in various organs. Because of this, IGF-I is expected to be used for the treatment of a variety of diseases. Since the amino acid sequence of IGF-I has a high similarity of about 40% to that of proinsulin, IGF-I can bind to an insulin receptor and thereby express insulin-like effects (Non-Patent Literature 1). In addition, since the amino acid sequence of the IGF-I receptor has a high similarity of about 60% to that of an insulin receptor, these receptors can form a heterodimer (Non-Patent Literature 1). Insulin can act on the insulin receptor to thereby express a strong effect of lowering the level of blood glucose, and is thus used as a hypoglycemic drug.

2. IGF-I Receptor

An IGF-I receptor is a transmembrane protein consisting of an alpha chain and a beta chain, and has six extracellular domains (L1, CR, L2, Fn1, Fn2, and Fn3), a transmembrane domain, and an intracellular domain (Non-Patent Literature 2). The intracellular domain of the IGF-I receptor incorporates a tyrosine kinase. The extracellular domain is a CR (cysteine-rich domain) and participates in activation of the intracellular tyrosine kinase associated with conformational change of the IGF-I receptor, which occurs when IGF-I binds to the IGF-I receptor. The IGF-I receptor forms a homodimeric complex (homo-type). IGF-I binding to the IGF-I receptor (homo-type) triggers signaling via activation of the receptor kinase. The IGF-I receptor also forms a heterodimeric complex (hetero-type) with the insulin receptor. Insulin or IGF-I binding to the IGF-I receptor (hetero-type) triggers signaling via activation of the receptor kinase (Non-Patent Literatures 3 and 4).

3. Physiological Effects of IGF-I

IGF-I has been shown to exhibit growth promoting effects, such as increasing the body length and the body weight, and insulin-like metabolic effects, such as glucose metabolism acceleration and hypoglycemic effects. It has been revealed that mecasermin, a human recombinant IGF-1, improves symptoms related to insulin receptor abnormality, such as hyperglycemia, hyperinsulinemia, acanthosis nigricans and hirsutism. IGF-I has also been shown to improve growth disorder of dwarfism resistant to growth hormone (Non-Patent Literature 5).

4. Growth Promoting Effects of IGF-I

IGF-I is known to enhance the ability of human chondrocytes for synthesizing DNA. In addition, administration of IGF-I increases the weight and elongates the femur bone length in the hypophysectomized rat (Non-patent Literature 5).

5. Effect of IGF-I on Increasing Muscle Mass

Enhancement of cell proliferation activity with IGF-I requires continuous activation of the IGF-I receptor (Non-Patent Literature 6). An animal engineered to overexpress the IGF-I receptor exhibits increased muscle mass (Non-Patent Literature 7). Sustained administration of IGF-I/IGFBP3 to a patient with proximal femur fracture enhances her/his grip strength and improves her/his ability of standing from a seated position without assistance (Non-Patent Literature 8). The muscle IGF-I levels of the elderly humans and mice are known to be lower than those of the young (Non-Patent Literatures 9 and 10). Over expression of IGF-I specifically in muscle tissues of elderly mice improved their muscle masses compared to wild-type mice (Non-Patent Literature 11).

6. Precedent Products for Increasing Muscle Mass

Anamorelin, a ghrelin receptor agonist, increased lean body mass in a clinical trial for cachexia, which is a disuse muscle atrophy. However, it involves adverse effects such as inducing nausea and hyperglycemia (Non-Patent Literature 12).

Myostatin, a negative control factor of skeletal myogenesis, affects activin receptor II (ActRII) to thereby inhibit Akt/mTOR (Non-Patent Literatures 13 to 15). LY2495655, an anti-myostatin antibody, increases the muscle masses of patients who received total hip replacement arthroplasty and those of elderly subjects (Non-Patent Literatures 16 and 17).

Bimagrumab, an anti-ActRII antibody, increases the muscle mass of neuromuscular disease patients (Non-Patent Literature 18). However, there is no drug so far which promotes formation of skeletal muscles and can thereby be used for the treatment of a subject in need thereof.

7. Hypoglycemic Effect of IGF-I

IGF-I is known to have hypoglycemic effect as an insulin-like effect. IGF-I enhances glucose uptake effect of rat muscle-derived cells (Non-Patent Literature 5). Administration of IGF-I also reduces the blood glucose level of rats (Non-Patent Literature 5).

It has been reported that the glucose lowering effect of IGF-I cause hypoglycemia as a clinical adverse effect (Non-Patent Literature 19). In addition, administration of IGF-I to a human subject causes hypoglycemia. Therefore, at the onset of IGF-I treatment, it is necessary to keep controlling the dosage starting from a low dosage with observing various clinical findings including the blood glucose level after administration (Non-Patent Literature 5).

IGF-I expresses hypoglycemic effect via promotion of Akt phosphorylation, which is a downstream signal of the IGF-I receptor. An active variant of Akt enhances glucose uptake by 3T3-L1 cells (Non-Patent Literature 20). On the other hand, an Akt2-deficient mouse exhibited elevated blood glucose level (Non-Patent Literature 21). An Akt inhibitor inhibits insulin-induced glucose uptake by rat muscle-derived cells (Non-Patent Literature 22). In addition, IGF-I is also known to activate an insulin receptor which plays a role in hypoglycemic effect. These findings suggest that the hypoglycemic effect of IGF-I involves overactivation of Akt and activation of the insulin receptor.

8. Short Half-Life of IGF-I in Blood

IGF-I has a short half-life in blood, and therefore requires frequent administrations when used in treatment. In fact, mecasermin, a human recombinant IGF-I, has a blood half-life of about 11 hours to about 16 hours, and therefore needs to be administered once to twice daily in the treatment of dwarfism (Non-Patent Literature 5).

About 70 to 80% of IGF-I is bound to IGFBP3 in blood, while a free form of IGF-I exhibits physiological effect. Binding of IGF-I to IGFBP3 maintains its half-life in blood to a time period of from about 10 hours to about 16 hours (Non-Patent Literature 1).

IPLEX, a combination drug of IGF-I with IGFBP3, exhibited a blood half-life extended from that of IGF-I to a time period of about 21 hours to about 26 hours, and thereby allowed for reduction of administration frequency to once daily (Non-Patent Literature 23). However, IPLEX was already withdrawn from the market.

There has been also an attempt to develop a PEGylated IGF-I with improved IGF-I kinetics, but no drug has successfully been developed so far and is currently available (Patent Literature 1).

9. Therapeutic Effects Expected to be Achieved Via IGF-I's Effects

IGF-I is known to affect various organs and exerts a wide variety of physiological functions (Non-Patent Literature 19).

IGF-I has been reported to have neuroprotective effect on the central nervous system by protecting mitochondria and antioxidant effect via activation of the IGF-I receptor (Non-Patent Literatures 24 and 25). IGF-I promotes regeneration of injured neurites (Non-Patent Literature 26).

IGF-I is a main factor of growth promotion (Non-Patent Literatures 27 and 28). In fact, mecasermin, a human recombinant IGF-I, is clinically used as a drug for the treatment of dwarfism.

IGF-I is deemed to be effective in the treatment of hepatic cirrhosis, which evolves from liver damage or chronic liver disease and involves hepatic fibrosis. Administration of IGF-I improved hepatic fibrosis in a model animal of hepatic cirrhosis (Non-Patent Literature 29).

IGF-I is also known to play a role in the development and functions of kidney. IGF-I has protective effect against oxidative stress and apoptosis due to glucotoxicity in mesangial cells of kidney (Non-Patent Literature 30). IGF-I is expected as a drug for the treatment of nephropathy.

Examples of conditions expected to be improved via IGF-I administration include: dwarfism, Laron syndrome, hepatic cirrhosis, hepatic fibrosis, aging, intrauterine growth restriction (IUGR), neurological disease, cerebral stroke, spinal cord injury, cardiovascular protection, diabetes, insulin resistant, metabolic syndrome, nephropathy, osteoporosis, cystic fibrosis, wound healing, myotonic dystrophy, AIDS-associated sarcopenia, HIV-associated fat redistribution syndrome, burn, Crohn's disease, Werner's syndrome, X-linked combined immunodeficiency disease, hearing loss, anorexia nervosa, and retinopathy of prematurity (Non-Patent Literature 19).

Thus, IGF-I is expected as a drug for the treatment of a variety of diseases because of its wide spectrum of physiological effects. However, problems such as its adverse hypoglycemic effect and its short half-life requiring multiple administrations have prevented its clinical applications.

10. IGF-I Receptor Agonist Antibodies

In general, antibody formulations have long half-life, and prove effective if administered once to twice a month. Although some IGF-I receptor agonist antibodies have been reported to be effective in activating the receptor in vitro, no antibodies have been reported to exhibit agonistic activity against the IGF-I receptor in vivo (Non-Patent Literatures 31 to 35).

Specifically, antibodies 3B7 and 2D1 enhance cellular DNA synthesis in vitro (Non-Patent Literature 32).

Antibodies 11A1, 11A4, 11A11, and 24-57 enhance tyrosine phosphorylation of IGF-1 receptor in vitro (Non-Patent Literature 33).

Antibodies 16-13, 17-69, 24-57, 24-60, 24-31, and 26-3 are shown to be effective in promoting cellular DNA synthesis and glucose uptake in vitro, and have the potential to exhibit hypoglycemic effect (Non-Patent Literatures 34 and 35).

However, no IGF-1 receptor agonist antibody has been reported to exhibit cell proliferation effects in an in vitro experiment using primary cultured cells, inter alia, human myoblast cells, let alone muscle-mass increasing effects in vivo.

11. IGF-I Receptor Antagonist Antibodies

There are attempts to use an antibody which binds to the IGF-1 receptor for the treatment of malignancies, based on its antagonist effect of inhibiting binding of IGF-1 to the IGF-1 receptor. However, existing IGF-1 receptor antagonist antibodies have various adverse effects such as hyperglycemia in monotherapy (Non-Patent Literature 36), and exhibit increased incidence of hyperglycemia when used in combination with other anticancer agents (Non-Patent Literature 37). Accordingly, their therapeutic applications are expected to be limited.

LIST OF CITATIONS

Patent Literature

[Patent Literature 1] JP2011-518778A

Non-Patent Literature

[Non-Patent Literature 1] Ohlsson, C., et al., The role of liver-derived insulin-like growth factor-1. Endocr Rev, 2009. 30(5): p. 494-535.

[Non-Patent Literature 2] Kavran, J. M., et al., How IGF-I activates its receptor. Elife, 2014. 3.

[Non-Patent Literature 3] Bailyes, E. M., et al., Insulin receptor/IGF-I receptor hybrids are widely distributed in mammalian tissues: quantification of individual receptor species by selective immunoprecipitation and immunoblotting. Biochem J, 1997. 327 (Pt 1): p. 209-15.

[Non-Patent Literature 4] Pandini, G., et al., Insulin/insulin-like growth factor I hybrid receptors have different biological characteristics depending on the insulin receptor isoform involved. J Biol Chem, 2002. 277(42): p. 39684-95.

[Non-Patent Literature 5] OrphanPacific, IF. 2015.

[Non-Patent Literature 6] Fukushima, T., et al., Phosphatidylinositol 3-kinase (PI3K) activity bound to insulin-like growth factor-I (IGF-1) receptor, which is continuously sustained by IGF-I stimulation, is required for IGF-1-induced cell proliferation. J Biol Chem, 2012. 287(35): p. 29713-21.

[Non-Patent Literature 7] Schiaffino, S. and C. Mammucari, Regulation of skeletal muscle growth by the IGF-I-Akt/PKB pathway: insights from genetic models. Skelet Muscle, 2011. 1(1): p. 4.

[Non-Patent Literature 8] Boonen, S., et al., Musculoskeletal effects of the recombinant human IGF-I/IGF binding protein-3 complex in osteoporotic patients with proximal femoral fracture: a double-blind, placebo-controlled pilot study. J Clin Endocrinol Metab, 2002. 87(4): p. 1593-9.

[Non-Patent Literature 9] Barton-Davis, E. R., et al., Viral mediated expression of insulin-like growth factor I blocks the aging-related loss of skeletal muscle function. Proc Natl Acad Sci USA, 1998. 95(26): p. 15603-7.

[Non-Patent Literature 10] Lamberts, S. W., A. W. van den Beld, and A. J. van der Lely, The endocrinology of aging. Science, 1997. 278(5337): p. 419-24.

[Non-Patent Literature 11] Musaro, A., et al., Localized IGF-I transgene expression sustains hypertrophy and regeneration in senescent skeletal muscle. Nat Genet, 2001. 27(2): p. 195-200.

[Non-Patent Literature 12] Temel, J. S., et al., Anamorelin in patients with non-small-cell lung cancer and cachexia (ROMANA 1 and ROMANA 2): results from two randomized, double-blind, phase 3 trials. Lancet Oncol, 2016. 17(4): p. 519-31.

[Non-Patent Literature 13] Glass, D. J., Signaling pathways perturbing muscle mass. Curr Opin Clin Nutr Metab Care, 2010. 13(3): p. 225-9.

[Non-Patent Literature 14] Lee, S. J. and A. C. McPherron, Regulation of myostatin activity and muscle growth. Proc Natl Acad Sci USA, 2001. 98(16): p. 9306-11.

[Non-Patent Literature 15] Amirouche, A., et al., Down-regulation of Akt/mammalian target of rapamycin signaling pathway in response to myostatin overexpression in skeletal muscle. Endocrinology, 2009. 150(1): p. 286-94.

[Non-Patent Literature 16] Woodhouse, L., et al., A Phase 2 Randomized Study Investigating the Efficacy and Safety of Myostatin Antibody LY2495655 versus Placebo in Patients Undergoing Elective Total Hip Arthroplasty. J Frailty Aging, 2016. 5(1): p. 62-70.

[Non-Patent Literature 17] Becker, C., et al., Myostatin antibody (LY2495655) in older weak fallers: a proof-of-concept, randomized, phase 2 trial. Lancet Diabetes Endocrinol, 2015. 3(12): p. 948-57.

[Non-Patent Literature 18] Amato, A. A., et al., Treatment of sporadic inclusion body myositis with bimagrumab. Neurology, 2014. 83(24): p. 2239-46.

[Non-Patent Literature 19] Puche, J. E. and I. Castilla-Cortazar, Human conditions of insulin-like growth factor-I (IGF-1) deficiency. J Transl Med, 2012. 10: p. 224.

[Non-Patent Literature 20] Kohn, A. D., et al., Expression of a constitutively active Akt Ser/Thr kinase in 3T3-L1 adipocytes stimulates glucose uptake and glucose transporter 4 translocation. J Biol Chem, 1996. 271(49): p. 31372-8.

[Non-Patent Literature 21] Cho, H., et al., Insulin resistance and a diabetes mellitus-like syndrome in mice lacking the protein kinase Akt2 (PKB beta). Science, 2001. 292(5522): p. 1728-31.

[Non-Patent Literature 22] Green, C. J., et al., Use of Akt inhibitor and a drug-resistant mutant validates a critical role for protein kinase B/Akt in the insulin-dependent regulation of glucose and system A amino acid uptake. J Biol Chem, 2008. 283(41): p. 27653-67.

[Non-Patent Literature 23] Submission for marketing application to FDA, APPLICATION NUMBER, 21-884

[Non-Patent Literature 24] Garcia-Fernandez, M., et al., Low doses of insulin-like growth factor I improve insulin resistance, lipid metabolism, and oxidative damage in aging rats. Endocrinology, 2008. 149(5): p. 2433-42.

[Non-Patent Literature 25] Puche, J. E., et al., Low doses of insulin-like growth factor-I induce mitochondrial protection in aging rats. Endocrinology, 2008. 149(5): p. 2620-7.

[Non-Patent Literature 26] Joseph D'Ercole, A. and P. Ye, Expanding the mind: insulin-like growth factor I and brain development. Endocrinology, 2008. 149(12): p. 5958-62.

[Non-Patent Literature 27] Abuzzahab, M. J., et al., IGF-I receptor mutations resulting in intrauterine and post-natal growth retardation. N Engl J Med, 2003. 349(23): p. 2211-22.

[Non-Patent Literature 28] Woods, K. A., et al., Intrauterine growth retardation and postnatal growth failure associated with deletion of the insulin-like growth factor I gene. N Engl J Med, 1996. 335(18): p. 1363-7.

[Non-Patent Literature 29] Perez, R., et al., Mitochondrial protection by low doses of insulin-like growth factor-I in experimental cirrhosis. World J Gastroenterol, 2008. 14(17): p. 2731-9.

[Non-Patent Literature 30] Kang, B. P., et al., IGF-I inhibits the mitochondrial apoptosis program in mesangial cells exposed to high glucose. Am J Physiol Renal Physiol, 2003. 285(5): p. F1013-24.

[Non-Patent Literature 31] Bhaskar, V., et al., A fully human, allosteric monoclonal antibody that activates the insulin receptor and improves glycemic control. Diabetes, 2012. 61(5): p. 1263-71.

[Non-Patent Literature 32] Xiong, L., et al., Growth-stimulatory monoclonal antibodies against human insulin-like growth factor I receptor. Proc Natl Acad Sci USA, 1992. 89(12): p. 5356-60.

[Non-Patent Literature 33] Runnels, H. A., et al., Human monoclonal antibodies to the insulin-like growth factor 1 receptor inhibit receptor activation and tumor growth in preclinical studies. Adv Ther, 2010. 27(7): p. 458-75.

[Non-Patent Literature 34] Soos, M. A., et al., A panel of monoclonal antibodies for the type I insulin-like growth factor receptor. Epitope mapping, effects on ligand binding, and biological activity. J Biol Chem, 1992. 267(18): p. 12955-63.

[Non-Patent Literature 35] Kato, H., et al., Role of tyrosine kinase activity in signal transduction by the insulin-like growth factor-I (IGF-1) receptor. Characterization of kinase-deficient IGF-1 receptors and the action of an IGF-1-mimetic antibody (alpha IR-3). J Biol Chem, 1993. 268(4): p. 2655-61.

[Non-Patent Literature 36] Atzori, F., et al., A Phase I Pharmacokinetic and Pharmacodynamic Study of Dalotuzumab (MK-0646), an Anti-Insulin-like Growth Factor-1 Receptor Monoclonal Antibody, in Patients with Advanced Solid Tumors. Clin Cancer Res., 2011.17(19): p. 6304-12.

[Non-Patent Literature 37] de Bono J. S., et al., Phase II randomized study of figitumumab plus docetaxel and docetaxel alone with crossover for metastatic castration-resistant prostate cancer. Clin Cancer Res., 2014.20(7): p. 1925-34.

SUMMARY OF INVENTION

Problem to be Solved by the Invention

An objective of the present invention is to provide an anti-IGF-I receptor humanized antibody or its fragment or a derivative thereof which specifically binds to an IGF-1 receptor of a vertebrate. Another objective of the present invention is to provide an antibody which increases the muscle mass via the IGF-1 receptor while not lowering the blood glucose level.

Means to Solve the Problem

The present invention relates to the following aspects:
Aspect [1]
An anti-IGF-I receptor humanized antibody or its fragment or a derivative thereof comprising:
  as a sequence of CDR-1 of the heavy chain variable region (CDR-H1), the amino acid sequence defined in SEQ ID NO:1, or an amino acid sequence derived from the amino acid sequence defined in SEQ ID NO:1 via substitution of one amino acid residue;
  as a sequence of CDR-2 of the heavy chain variable region (CDR-H2), the amino acid sequence defined in SEQ ID NO:2, or an amino acid sequence derived from the amino acid sequence defined in SEQ ID NO:2 via substitution of one or two amino acid residues;
  as a sequence of CDR-3 of the heavy chain variable region (CDR-H3), the amino acid sequence defined in SEQ ID NO:3, or an amino acid sequence derived from the amino acid sequence defined in SEQ ID NO:3 via substitution of one or two amino acid residues;
  as a sequence of CDR-1 of the light chain variable region (CDR-L1), the amino acid sequence defined in SEQ ID NO:4, or an amino acid sequence derived from the amino acid sequence defined in SEQ ID NO:4 via substitution of one or two amino acid residues;
  as a sequence of CDR-2 of the light chain variable region (CDR-L2), the amino acid sequence defined in SEQ ID NO:5, or an amino acid sequence derived from the amino acid sequence defined in SEQ ID NO:5 via substitution of one amino acid residue; and
  as a sequence of CDR-3 of the light chain variable region (CDR-L3), the amino acid sequence defined in SEQ ID NO:6, or an amino acid sequence derived from the amino acid sequence defined in SEQ ID NO:6 via substitution of one or two amino acid residues;
  wherein the antibody, fragment, or derivative thereof specifically binds to an extracellular domain of SEQ ID NO:14 (human IGF-1 receptor).
Aspect [2]
The anti-IGF-I receptor humanized antibody or its fragment or a derivative thereof according to [1], comprising:
  as a sequence of a heavy-chain variable region, the amino acid sequence defined in SEQ ID NO:7, or an amino acid sequence derived from the amino acid sequence defined in SEQ ID NO:7 via substitution, deletion, or addition of one or several amino acid residues; and
  as a sequence of a light-chain variable region, the amino acid sequence defined in SEQ ID NO:8, or an amino acid sequence derived from the amino acid sequence defined in SEQ ID NO:8 via substitution, deletion, or addition of one or several amino acid residues.
Aspect [3]
The anti-IGF-I receptor humanized antibody or its fragment or a derivative thereof according to [1] or [2], comprising:
  as a sequence of a heavy-chain variable region, the amino acid sequence defined in SEQ ID NO:7; and
  as a sequence of a light-chain variable region, an amino acid sequence selected from SEQ ID NOs:8, 9, 10, 11, and 12.
Aspect [4]
The anti-IGF-I receptor humanized antibody or its fragment or a derivative thereof according to any one of [1] to [3], comprising:
  as heavy- and light-chain constant regions, the constant regions of each class of human immunogloblin.
Aspect [5]
The anti-IGF-I receptor humanized antibody or its fragment or a derivative thereof according to [4], wherein the heavy-chain constant region is the heavy-chain constant region of human IgG class 4.
Aspect [6]
The anti-IGF-I receptor humanized antibody or its fragment or a derivative thereof according to any one of [1] to [5], which binds to an epitope comprising a peptide having an amino acid sequence corresponding to the amino acid residues Nos. 308 to 319 (ProSerGlyPheIleArgAsnGlySerGlnSerMet) of SEQ ID NO:14 (human IGF-1 receptor) or a region in the visinity thereof.
Aspect [7]
The anti-IGF-I receptor humanized antibody or its fragment or a derivative thereof according to any one of [1] to [6], which, when administered at a dosage sufficient to induce proliferation of cultured myoblasts derived from human or guinea pig, does not induce glucose uptake of the cultured cells.
Aspect [8]
The anti-IGF-I receptor humanized antibody or its fragment or a derivative thereof according to any one of [1] to [7], which, when administered to a vertebrate at a dosage sufficient to induce an increase in the muscle mass and/or the body length of the vertebrate, does not decrease the blood glucose level of the vertebrate.
Aspect [9]
The anti-IGF-I receptor humanized antibody or its fragment or a derivative thereof according to [8], which, when administered to a vertebrate at a blood exposure level which is 10 times or more an effective dosage to induce an increase in the muscle mass and/or the body length of the vertebrate, does not decrease the blood glucose level of the vertebrate.
Aspect [10]
A nucleic acid molecule consisting of a polynucleotide sequence encoding an anti-IGF-1 receptor humanized antibody or its fragment or a derivative thereof according to any one of [1] to [9].
Aspect [11]
A cloning vector or expression vector comprising at least one nucleic acid molecule according to [10].
Aspect [12]
A recombinant cell derived by introducing a vector according to [11] into a host cell.
Aspect [13]
A process of producing an anti-IGF-I receptor humanized antibody or its fragment or a derivative thereof according to any one of [1] to [9], comprising culturing a recombinant cell according to [12]; and
purifying an anti-IGF-I receptor humanized antibody or its fragment or a derivative thereof produced by the recombinant cell.

Aspect [14]

A pharmaceutical composition comprising, as an active ingredient, an anti-IGF-I receptor humanized antibody or its fragment or a derivative thereof according to any one of [1] to [9], a nucleic acid molecule according to [10], a vector according to [11], or a recombinant cell according to [12].

Aspect [15]

A pharmaceutical composition according to [14], for use in the treatment of muscle atrophic disease or dwarfism.

Aspect [16]

A pharmaceutical composition according to [15], wherein the muscle atrophic disease is disuse muscle atrophy, sarcopenia, or cachexia.

Aspect [17]

A pharmaceutical composition according to [15], wherein the dwarfism is Laron-type dwarfism or growth-hormone resistant dwarfism.

Effect of the Invention

The antibody or its fragment or a derivative thereof according to the present invention has an effect of specifically binding to an IGF-1 receptor of a vertebrate.

BRIEF EXPLANATION OF THE DRAWINGS

FIG. 1 illustrates aligned amino acid sequences of CR domains of the mouse (SEQ ID NO: 26), rat (residues 121-360 of SEQ ID NO: 20), human (residues 121-359 of SEQ ID NO: 14), guinea pig (residues 121-359 of SEQ ID NO: 16) and rabbit (SEQ ID NO: 25) IGF-1 receptors, in which the amino acid sequences are indicated using the one letter code (IGF1R_MOUSE: SEQ ID NO: 27, IGF1R_RAT: position 121 to position 360 of SEQ ID NO: 20, IGF1R_HUMAN: position 121 to position 359 of SEQ ID NO: 14, IGF1R_CAVY: position 121 to position 359 of SEQ ID NO: 16, and IGF1R_RABIT: SEQ ID NO: 28);

EMBODIMENTS OF THE INVENTION

Figure 2:
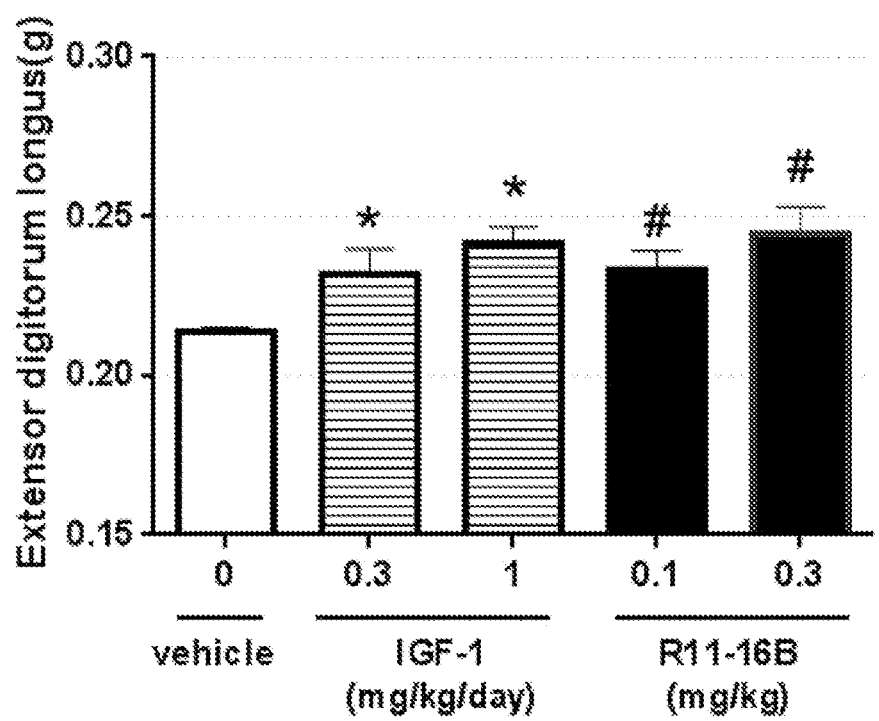
FIG. 2 is a graph indicating the weights of extensor digitorum longus muscles of guinea pigs that received continuous administration of IGF-I with an osmotic pump or single-dose intravenous administration of anti-IGF-I receptor humanized antibody R11-16B at two weeks after administration.

In the following description, the present invention will be explained with reference to specific embodiments, although the present invention should not be limited to these embodiments in any way. All the literatures cited in the present specification, including patent publications, unexamined application publications, and non-patent literatures, are hereby incorporated by reference in their entirety for all purposes.

[IGF]

In the present disclosure, IGF refers to as an insulin-like growth factor, which may be either IGF-I or IGF-II. Both IGF-I and IGF-II are biological ligands having agonist activities which bind to an IGF-I receptor (insulin-like growth factor-I receptor) and transduce signals such as cell division and metabolism into the cell. IGF-I and IGF-II are also known to have cross-avidity to an insulin receptor (INSR), which is structurally similar to the IGF-I receptor. The present specification will mainly discuss IGF-I, since its properties such as physiological functions are known more than those of IGF-II. However, in the context of discussion about various effects and diseases mediated via binding of a ligand to the IGF-I receptor, both IGF-I and IGF-II may collectively be mentioned.

IGF-I, also referred to as somatomedin C, is a single polypeptide hormone consisting of 70 amino acids. The sequence of human IGF-I is available, e.g., on the EMBL-EBI with UniProtKB accession number P50919. The amino acid sequence of mature IGF-I is shown in SEQ ID NO:13 of the sequence listing attached hereto. This sequence consisting of 70 amino acids is conserved in many species. In the present invention, the term "IGF-I" without any limitation means an IGF-I protein having such hormone activity, unless specified otherwise.

IGF-I is produced by a variety of cells in the living body, including liver cells, and exists in blood and other body fluids. Therefore, wild-type IGF-I can be obtained via purification from body fluid of an animal or from a primary cultured cell or a cultured cell line derived from an animal. Since a growth hormone induces IGF-I production by cells, IGF-I can also be purified from body fluid of an animal to which a growth hormone has been administered, or from a primary cultured animal cell or an animal cell line incubated in the presence of a growth hormone. As a different method, IGF-I can also be obtained from a recombinant cell prepared by transfection of an expression vector carrying a nucleic acid molecule encoding an amino acid sequence of IGF-I into a host such as a prokaryotic organism (e.g., *E. coli*) or a eukaryotic cell including a yeast, an insect cell, or a cultured mammal-derived cell, or from a transgenic animal or a transgenic plant into which an IGF-I gene has been transfected. Human IGF-I is also available as a research reagent (Enzo Life Sciences, catalog: ADI-908-059-0100, Abnova, catalog: P3452, etc.) or as a pharmaceutical product (SOMAZON® mecasermin, INCRELEX®, etc.). The in vivo and in vitro activities of IGF-I for use can be evaluated as specific activities relative to an IGF-I standard substance under NIBSC code: 91/554, whose activity corresponds to one international unit/microgram. The standard substance is available from World Health Organization's National Institute for Biological Standards and Control (NIBSC). In the context of the present invention, IGF-I is considered as having a specific activity equivalent to the IGF-I of NIBSC code: 91/554.

[Igf-I Receptor]

In the present disclosure, the term "IGF-I receptor" refers to as an insulin-like growth factor-I receptor. The term "IGF-I receptor" used herein means an IGF-I receptor protein, unless specified otherwise. The IGF-I receptor is a protein formed with two subunits, each consisting of an alpha chain and a beta chain. The amino acid sequence of a human IGF-I receptor is indicated in SEQ ID NO:14, of which a subsequence consisting of the $31^{st}$ to $735^{th}$ amino acid residues represents the alpha chain, while a subsequence starting from the $740^{th}$ amino acid residue represents the beta chain. The alpha chain of the IGF-I receptor has a portion to which IGF-I binds, while the beta chain has a transmembrane structure and exhibits a function to transmit signals into the cell. The alpha chain of the IGF-I receptor can be divided into L1, CR, L2, FnIII-1, and FnIII-2a/ID/FnIII-2b domains. According to the amino acid sequence of the human IGF-I receptor defined in SEQ ID NO:14, the $31^{st}$ to $179^{th}$ residues correspond to the L1 domain, the $180^{th}$ to $328^{th}$ residues correspond to the CR domain, the $329^{th}$ to $491^{st}$ residues correspond to the L2 domain, the $492^{nd}$ to $607^{th}$ residues correspond to the FnIII-1 domain, and the $608^{th}$ to $735^{th}$ residues correspond to the FnIII-2a/ID/FnIII-2b domain. Among them, the CR (cysteine-rich) domain is involved in the activation of an intracellular tyrosine kinase in the beta chain, which is associated with a conformational change of the IGF-I receptor occurring when IGF-I binds to the receptor. The amino acid sequence of human IGF-I receptor is available, e.g., on EMBL-EBI with UniProtKB-accession number P08069, and is also indicated in the sequence listing as SEQ ID NO:14.

The IGF-I receptor is known to be expressed in a wide range of tissues and cells in the living body, and receives various stimuli via IGF-I, such as induction of cell proliferation and activation of intracellular signals. In particular, effects of IGF-I on myoblasts via the IGF-I receptor can be evaluated using cell proliferation activities as indicators. For this reason, myoblasts are useful in analyzing the effects of antibodies binding to the IGF-I receptor. Cells expressing an IGF-I receptor derived from human or any other vertebrate can be prepared artificially, by transfection of an expression vector carrying a nucleic acid molecule encoding the amino acid sequence of an IGF-I receptor derived from human or any other vertebrate into a eukaryotic host cell, such as a cultured insect cell or a mammal-derived cell, to prepare a recombinant cell expressing the IGF-I receptor encoded by the transfected nucleic acid on its cell membrane. The resultant cell expressing the IGF-I receptor can be used for analysis of the binding ability and intracellular signal transmissibility of antibodies.

[Anti-IGF-I Receptor Humanized Antibody]

One aspect of the present invention provides a novel anti-IGF-I receptor humanized antibody (hereinafter referred to as "the antibody of the present invention" as appropriate).

In the present disclosure, the term "an antibody" indicates a glycoprotein containing at least two heavy (H) chains and two light (L) chains coupled together via disulfide bindings. Each heavy chain has a heavy chain variable region (abbreviated as VH) and a heavy chain constant region. The heavy chain constant region contains three domains, i.e., CH1, CH2, and CH3. Each light chain contains a light chain variable region (abbreviated as VL) and a light chain constant region. A light chain constant region has one domain, i.e., CL. There are two types of light chain constant regions, i.e., λ (lambda) chain and κ (kappa) chain. Heavy chain constant regions are classified into γ (gamma) chain, μ (mu) chain, α (alpha) chain, δ (delta) chain and ε (epsilon) chain, and different types of heavy chain constant regions result in different isotypes of antibodies, i.e., IgG, IgM, IgA, IgD, and IgE, respectively. Each of the VH and VL is also divided into four relatively conserved regions (FR-1, FR-2, FR-3, and FR-4), collectively referred to as framework regions (FR), and three highly variable regions (CDR-1, CDR-2, and CDR-3), collectively referred to as complementarity determining regions (CDR). The VH region includes the three CDRs and the four FRs arranged in the order of FR-1, CDR-1 (CDR-H1), FR-2, CDR-2 (CDR-H2), FR-3, CDR-3 (CDR-H3), and FR-4 from the amino terminal to the carboxyl terminal. The VL includes the three CDRs and the four FRs arranged in the order of FR-1, CDR-1 (CDR-L1), FR-2, CDR-2 (CDR-L2), FR-3, CDR-3 (CDR-L3), and FR-4 from the amino terminal to the carboxyl terminal. The variable region of each of the heavy chain and the light chain includes a binding domain, which interacts with an antigen.

The antibody of the present invention may be a fragment and/or derivative of an antibody. Examples of antibody fragments include F(ab')2, Fab, and Fv. Examples of antibody derivatives include: antibodies to which an amino acid mutation has been introduced in its constant region; antibodies in which the domain arrangement of the constant regions has been modified; antibodies having two or more Fc's per molecule; antibodies consisting only of a heavy chain or only of a light chain; antibodies with modified glycosylation; bispecific antibodies; conjugates of antibodies or antibody fragments with compounds or proteins other than antibodies; antibody enzymes; nanobodies; tandem scFv's; bispecific tandem scFv's; diabodies; and VHHs. The term "antibody" used herein encompasses such fragments and/or derivatives of antibodies, unless otherwise specified.

In the present disclosure, the term "antigen-antibody reaction" used herein means that an antibody binds to an IGF-I receptor with an affinity represented by an equilibrium dissociation constant (KD) of $1\times10^{-7}$M or less. The antibody of the present invention should preferably bind to an IGF-I receptor with a KD of usually $1\times10^{-5}$M or less, particularly $1\times10^{-6}$M or less, more particularly $1\times10^{-7}$M or less.

In the present disclosure, the term "specificity" of an antibody to an antigen means that high antigen-antibody reaction occurs between the antibody and the antigen. In the context of the present disclosure, the term "the IGF-I receptor-specific antibody" means an antibody which, when used at a concentration sufficient to significantly cause antigen-antibody reaction with cells expressing an IGF-I receptor, causes antigen-antibody reaction with an INSR at a reactivity of 1.5 times or less the reactivity with a Mock cell. The INSR has a high similarity to an IGF-I receptor in primary structure (amino acid sequence) and higher-order structure.

A person skilled in the art would be able to carry out measurement of antigen-antibody reaction by selecting an appropriate binding assay in a system of a solid phase or liquid phase. Examples of such assays include, although not limited to: enzyme-linked immunosorbent assay (ELISA), enzyme immunoassay (EIA), surface plasmon resonance (SPR), fluorescence resonance energy transfer (FRET), and luminescence resonance energy transfer (LRET). Measurement of antigen-antibody binding affinity can be carried out by, e.g., labelling an antibody and/or an antigen with, e.g., an enzyme, a fluorescent material, a luminescent material, or a radioisotope, and detecting the antigen-antibody reaction using a method suitable for measuring the physical and/or chemical properties characteristic to the label used.

By binding to the CR domain of the IGF-I receptor, the antibody of the present invention is deemed to activate a homo-type receptor, in which the IGF-I receptor forms a dimer, or a hetero-type receptor, in which the IGF-I receptor and INSR form a dimer.

The antibody of the invention should preferably have specific amino acid sequences as CDR sequences, as will be explained in details below. In the context of the present invention, the term "identity" of amino acid sequences used herein means the ratio of identical amino acid residues between the sequences, while the term "similarity" of amino acid sequences used herein means the ratio of identical or similar amino acid residues between the sequences. The similarity and identity of amino acid sequences can be determined, e.g., using BLAST method (with default conditions of PBLAST provided by NCBI).

The term "similar amino acid residues" used herein means a group of amino acid residues having side chains with similar chemical properties (e.g., electric charge or hydrophobicity). Groups of similar amino acid residues include:
1) amino acid residues having aliphatic side chains: glycine, alanine, valine, leucine, and isoleucine residues;
2) amino acid residues having aliphatic hydroxyl side chains: serine and threonine residues;
3) amino acid residues having amide-containing side chains: asparagine and glutamine residues;
4) amino acid residues having aromatic side chains: phenylalanine, tyrosine, and tryptophan residues;
5) amino acid residues having basic side chains: lysine, arginine, and histidine residues;
6) amino acid residues having acidic side chains: aspartic acid and glutamic acid residues; and
7) amino acid residues having sulfur-containing side chains: cysteine and methionine residues.

According to the present invention, a heavy chain variable region CDR-1 (CDR-H1) sequence is preferably an amino acid sequence defined in SEQ ID NO:1 (SerTyrTrpMetHis) or an amino acid sequence derived from SEQ ID NO:1 via substitution of an amino acid residue at any one position. In addition, the CDR-H1 sequence in the heavy chain variable region preferably has 80% or more homology (preferably identity) with SEQ ID NO: 1.

A heavy chain variable region CDR-2 (CDR-H2) sequence is preferably an amino acid sequence defined in SEQ ID NO:2 (GluThrAsnProSerAsnSerValThrAsnTyrAsnGluLysPheLysSer) or an amino acid sequence derived from SEQ ID NO: 2 via substitution of one or more amino acid residues at any one or two positions. In addition, the CDR-H2 sequence in the heavy chain variable region has preferably 88% or more, more preferably 94% homology (preferably identity) with SEQ ID NO: 2.

A heavy chain variable region CDR-3 (CDR-H3) sequence is preferably an amino acid sequence defined in SEQ ID NO:3 (GlyArgGlyArgGlyPheAlaTyr) or an amino acid sequence derived from SEQ ID NO: 3 via substitution of one or more amino acid residues at any one or two positions. In addition, the CDR-H3 sequence in the heavy chain variable region has preferably 75% or more, more preferably 87% or more homology (preferably identity) with SEQ ID NO: 3.

A light chain variable region CDR-1 (CDR-L1) sequence is preferably an amino acid sequence defined in SEQ ID NO: 4 (ArgAlaSerGlnAsnIleAsnPheTrpLeuSer) or an amino acid sequence derived from SEQ ID NO: 4 via substitution of one or more amino acid residues at any one or two positions. In addition, the CDR-L1 sequence in the light chain variable region has preferably 81% or more, more preferably 90% or more homology (preferably identity) with SEQ ID NO: 4.

A light chain variable region CDR-2 (CDR-L2) sequence is preferably an amino acid sequence defined in SEQ ID NO: 5 (LysAlaSerAsnLeuHisThr) or an amino acid sequence derived from SEQ ID NO: 5 via substitution of an amino acid residue at any one position. In addition, the CDR-L2 sequence in the light chain variable region preferably has 85% or more homology (preferably identity) with SEQ ID NO: 5.

A light chain variable region CDR-3 (CDR-L3) sequence is preferably an amino acid sequence defined in SEQ ID NO: 6 (LeuGlnGlyGlnSerTyrProTyrThr) or an amino acid sequence derived from SEQ ID NO: 6 via substitution of one or more amino acid residues at any one or two positions. In addition, the CDR-L3 sequence in the light chain variable region has preferably 77% or more, more preferably 88% or more homology (preferably identity) with SEQ ID NO: 6.

In particular, the antibody of the present invention preferably has any combination of the following CDR sequences: the amino acid sequence of SEQ ID NO: 1 as the CDR-H1 sequence; the amino acid sequence of SEQ ID NO: 2 as the CDR-H2 sequence; the amino acid sequence of SEQ ID NO: 3 as the CDR-H3 sequence; the amino acid sequence of SEQ ID NO: 4 as the CDR-L1 sequence; the amino acid sequence of SEQ ID NO: 5 as the CDR-L2 sequence; and the amino acid sequence of SEQ ID NO: 6 as the CDR-L3 sequence.

Examples of the method of identifying each sequence of CDR-H1, CDR-H2, CDR-H3, CDR-L1, CDR-L2, or CDR-L3 in an antibody include a Kabat method (Kabat et al., The Journal of Immunology, 1991, Vol. 147, No. 5, pp. 1709-1719) and a Chothia method (Al-Lazikani et al., Journal of Molecular Biology, 1997, Vol. 273, No. 4, pp. 927-948). These methods are technologically common to those skilled in the art, and their overview may be available from, for example, the Internet web page of Dr. Andrew C. R. Martin's Group (www.bioinf.org.uk/abs/).

A framework sequence of an immunoglobulin, which is the antibody of the present invention, is preferably a framework sequence in each class of a human immunoglobulin.

The heavy chain variable region and the light chain variable region in the antibody of the present invention preferably has specific amino acid sequences, as described below in detail. In the present disclosure, the phrase "one or several positions" indicates one position, two positions, three positions, four positions, five positions, six positions, seven positions, eight positions, nine positions, or ten positions unless otherwise specified.

The heavy chain variable region in the antibody of the present invention preferably has an amino acid sequence defined in SEQ ID NO: 7, an amino acid sequence derived from SEQ ID NO: 7 via substitution of one or more amino acid residues at any one or several positions, or an amino acid sequence having 90% or more homology (preferably identity) with SEQ ID NO: 7. The light chain variable region in the antibody of the present invention preferably has an amino acid sequence defined in SEQ ID NO: 8, an amino acid sequence derived from SEQ ID NO: 8 via substitution of one or more amino acid residues at any one or several positions, or an amino acid sequence having 90% or more homology (preferably identity) with SEQ ID NO: 8.

In particular, the antibody of the present invention preferably has SEQ ID NO: 7 as the heavy chain variable region, and SEQ ID NO: 8 as the light chain variable region or a sequences including an amino acid sequence in which Tyr is replaced with Ala, Ser, Phe or Cys at position 36 (Kabat number: L36) of SEQ ID NO: 8 (SEQ ID NO: 9, SEQ ID NO: 10, SEQ ID NO: 11 and SEQ ID NO: 12, respectively).

The amino acid sequence of each framework region and/or each constant region of the heavy chain and light chain in the antibody of the present invention may be selected from, for example, human IgG, IgA, IgM, IgE, and IgD classes and variants thereof. One example of the heavy chain constant region in the antibody of the present invention is a heavy chain constant region of human IgG4.

[Epitope of Anti-IGF-I Receptor Humanized Antibody]

The antibody of the present invention uses a CR domain of IGF-I receptor as an epitope. The antibody of the present invention preferably binds to or to its vicinity of an epitope including a peptide having an amino acid sequence corresponding to amino acid numbers 308 to 319 (ProSerGlyPheIleArgAsnGlySerGlnSerMet) of SEQ ID NO: 14 (human IGF-I receptor). The antibody of the present invention probably binds to the CR domain of IGF-I receptor and thereby activate a homo-type receptor in which the IGF-I receptor forms a dimer or a hetero-type receptor in which the IGF-I receptor and INSR form a dimer. It is noted that the agonist antibody of the present invention described later (i.e., the antibody of the present invention which is an agonist antibody) has no avidity to the INSR having a high similarity to a primary structure (amino acid sequence) and a higher structure of the IGF-I receptor.

[IGF-I Receptor Agonist Antibody and Antagonist Antibody]

The antibody of the present invention includes both an agonist antibody and an antagonist antibody (hereinafter, the agonist antibody and the antagonist antibody of the present invention, respectively, will be appropriately referred to as "the inventive agonist antibody" and "the inventive antagonist antibody"). The inventive agonist antibody has an effect to enhance the proliferation activity on myoblast cells by IGF-I in independent use. In contrast, the inventive antagonist antibody has an effect to block the proliferation activity on myoblast cells by IGF-I in combined use with IGF-I.

The inventive agonist antibody is preferably a human IgG class or its variant, more preferably a human IgG4 subclass or its variant or a human IgG1 subclass or its variant. In one example, a stabilized IgG4 constant region includes proline at position 241 in the hinge region in accordance with the Kabat's numbering scheme. This position corresponds to position 228 in the hinge region in accordance with the EU numbering scheme (Kabat et al., Sequences of Proteins of Immunological Interest, DIANE Publishing, 1992, Edelman et al., Proc. Natl. Acad. Sci USA, 63, 78-85, 1969). The residue at this position in human IgG4 is usually serine, and the replacement of serine with proline can lead to stabilization. In another example, incorporation of N297A mutation into the constant region of IgG1 serves to minimize the ability to bind to Fc receptors and/or fix a complement.

The inventive agonist antibody strongly binds to a specific domain of the IGF-I receptor and has an effect to enhance in vitro proliferation activity on myoblast cells.

In addition, the inventive agonist antibody is characterized by having no effect of enhancing in vitro glucose uptake into differentiated muscle cells. In detail, the inventive agonist antibody has no effect of enhancing in vitro glucose uptake into cultured differentiated muscle cells at an effective concentration to enhance the proliferation activity on myoblast cells (e.g., myoblast cells derived from humans or guinea pigs), more preferably at a concentration 10 times higher, or more preferably even at a concentration 100 times higher than the effective concentration.

The inventive agonist antibody has no hypoglycemic effect at a dose that exhibits an effect of increasing muscle mass. IGF-I has a significant hypoglycemic effect in the case of administration at a dose that exhibits an effect of increasing muscle mass. However, the inventive agonist antibody does not have an effect of lowering a blood glucose level in a vertebrate at a dose that induces an increase in muscle mass and/or body length of the vertebrate. The inventive agonist antibody does not preferably have an effect of lowering a blood glucose level in a vertebrate even in the case that the antibody is administered such that a blood exposure level reaches 10 times or more an effective dose that induces an increase in muscle mass and/or body length of the vertebrate.

Furthermore, the inventive agonist antibody has an in vivo activity to increase muscle mass in single administration comparable to that in sustained administration of IGF-I. In addition, the inventive agonist antibody has a long half-life in blood, and exhibits an effect of increasing muscle mass in single administration to the vertebrate.

These results demonstrate that the inventive agonist antibody has a high potential as a therapeutic agent or prophylactic agent, which is an advantage of IGF-I, in various diseases associated with IGF-I receptors, such as disuse muscle atrophy and dwarfism, and can overcome a hypoglycemic effect and a short half-life in blood, which are disadvantages of IGF-I.

In contrast, the inventive antagonist antibody has an effect to block the binding of IGF-I to the IGF-I receptor.

In one embodiment, the inventive antagonist antibody activates the IGF-I receptor but blocks the effect of IGF-I on the IGF-I receptor. In this case, the antibody has an effect to counteract an additive agonist activity of IGF-I, for example, the proliferation-inducing activity of myoblast cells by IGF-I.

In another embodiment, the inventive antagonist antibody binds to the IGF-I receptor but does not activate the IGF-I receptor. Examples of such antagonist antibodies that cause no activation due to cross-linking of the IGF-I receptor include, but are not limited to, antibodies that are monovalent in antigen binding, such as Fab and scFv, antibodies that have bivalent binding positions, such as bispecific antibodies, but bind to specific domain of the IGF-I receptor at only one side of the binding positions, and antibodies in which the distance between the bivalent binding positions is varied with, for example, a linker.

In an antagonist antibody that binds to the IGF-I receptor but does not have agonist activity among the inventive antagonist antibodies, a method of measuring antigen-antibody reaction between the antibody and the IGF-I receptor can confirm that such an antibody has an avidity to the IGF-I receptor, while a cell proliferation assay on cells, for example, myoblast cells can confirm that such an antibody does not have a cell proliferation-inducing activity.

In addition, the inventive antagonist antibody does not affect in vitro glucose uptake into differentiated muscle cells or in vivo blood glucose level. Accordingly, the inventive antagonist antibody serves as an anti-IGF-I receptor humanized antibody that does not cause side effects, such as hyperglycemia, and has a high potential as a therapeutic agent or a prophylactic agent for malignant tumors, such as breast cancer, colon cancer, sarcoma, lung cancer, prostate cancer, thyroid cancer, and myeloma.

[Cross-Reaction]

The antibody of the present invention should preferably cross-react with the IGF-I receptor of another vertebrate. The term "cross-reaction" means that while the antibody causes antigen-antibody reaction with the IGF-I receptor from a target animal (such as human), the antibody also has an ability to bind to an antigen derived from another animal different from the target animal. The antibody should preferably has a cross-reactivity with the IGF-I receptor of a different animal from the target animal whose IGF-I receptor is the target of the antigen-antibody reaction by the antibody, such as human or a non-human animal including guinea pig, monkey, rabbit, cow, pig, horse, sheep, dog, or fowl. Example 4 described later demonstrates that an anti-IGF-I receptor humanized antibody, R11-16B, was shown to bind to the ProSerGlyPheIleArgAsnGlySerGlnSerMet sequence in the CR domain of the human IGF-I receptor. Since this ProSerGlyPheIleArgAsnGlySerGlnSerMet sequence is conserved in the homologous parts of the IGF-I receptors of monkey (cynomolgus monkey), rabbit, guinea pig, cow, sheep, horse, and dog, this antibody has cross-binding ability to the IGF-I receptors from these species. In addition, since the amino acid sequences of the homologous parts of mouse and rat are both ProSerGlyPheIleArgAsnSerThr-GlnSerMet, screening for an anti-IGF-1 receptor antibody which binds to this part makes it possible to obtain an antibody which binds to the IGF-1 receptors of, e.g., mouse and rat, and also has similar characteristics and functions as those of R11-16B.

Alternatively, a cell or an animal of a species which does not cross-react with the antibody of the present invention can be altered via genetic engineering into a cell or an animal expressing an IGF-1 receptor with which the antibody of the present invention cross-reacts.

[Proliferation-Inducing Activity of Vertebrate-Derived Cells and Activity to Induce an Increase in the Muscle Mass and/or the Body Length]

An anti-IGF-I receptor humanized antibody according to an embodiment of the present invention has proliferation-inducing activity of vertebrate-derived cells. Although IGF-1 receptor agonist antibodies were already known, no antibody has been reported to show the proliferation-inducing activity of primary cultured cells, particularly myoblasts. Also, there has been no known antibody reported so far as having cell proliferation-inducing activity at a dosage lower than the $EC_{50}$ value of IGF-1 in vitro.

The term "vertebrate-derived cells" in the context of the present disclosure should preferably be cells derived from mammals, birds, reptiles, amphibia, or fish, more preferably cells derived from mammals or birds, further more preferably cells derived from human, monkey, rabbit, guinea pig, cow, pig, sheep, horse or dog. Cells derived from these species which express an IGF-1 receptor with which the antibody of the present invention cross-reacts can be induced to proliferate by the antibody of the present invention. The "vertebrate-derived cells" according to the present disclosure also encompass: cells and animals engineered to express an IGF-1 receptor of a species with which the antibody of the present invention cross-reacts; and modified animal cells derived from such engineered cells and animals.

An antibody's proliferation-inducing activity of vertebrate-derived cells can be analyzed in vitro using primary cultured cells, established cell lines, or transformants derived from such cells.

In the present disclosure, the term "primary cultured cells" means cells which were isolated from an organ or a tissue of a living organism, and can typically be subcultured for some passages. Primary cultured cells derived from a vertebrate can be obtained from an organ or a tissue of the vertebrate via enzyme treatment, dispersion with physical means, or explant method. An organ or a tissue or its fragment obtained from the vertebrate can also be used for analyzing the antibody's activity above. Preferable examples of organs and tissues from which primary cells are prepared include: endocrine tissues such as thyroid, parathyroid, and adrenal gland; immune tissues such as appendix, tonsil, lymph nodes, and spleen; respiratory organs such as trachea and lung; digestive organs such as stomach, duodenum, small intestine, and large intestine; urinary organs such as kidney and urinary bladder; male genital organs such as vas deferens, testicle, and prostate; female genital organs such as breast and fallopian tube; and muscle tissues such as heart muscle and skeletal muscles. More preferred examples include liver, kidney, or digestive organs or muscle tissues, among which muscle tissues are still more preferred. Primary cultured cells which can be used for analyzing the proliferation-inducing activity of an antibody of the present invention are cells which express an IGF-I receptor and can be induced to proliferate by IGF-I binding to the IGF-I receptor. Typical examples thereof are skeletal muscle myoblasts, which are primary cultured cells isolated from muscle tissue. Human- or animal-derived primary cultured cells available by assignment or commercially on the market can also be obtained and used. Human primary cultured cells are available from various institutions and companies, e.g., ATCC®, ECACC, Lonza, GIBCO®, Cell Applications, ScienCell research laboratories, and Promo-Cell.

In the present disclosure, the term "cell line" means a line of cultured cells which were derived from a living organism and then immortalized such that they can semipermanently proliferate with maintaining their specific properties. Cell lines are divided into non-tumor-derived cell lines and tumor-derived cell lines. Vertebrate-derived cell lines which can be used for analyzing the proliferation-inducing activity of the antibody of the present invention are cells which express an IGF-I receptor and can be induced to proliferate by IGF-I binding to the IGF-I receptor. Examples of cell lines which express an IGF-I receptor and can be induced to proliferate by IGF-I include, although not limited to: human neuroblastoma SH-SY5Y, human epidermal keratinocyte line HaCaT, human alveolar basal epithelial adenocarcinoma cell line A549, human colon-adenocarcinoma cell line Caco-2, human hepatocellular cancer cell line HepG2, human cervical cancer cell line Hela, human cervical cancer cell line SiHa, human breast cancer cell line MCF7, human pluripotent human embryonal carcinoma line NTERA-2, and human bone cancer cell line U-2-OS.

In the present disclosure, transformants which can be used for analyzing the proliferation-inducing activity of the antibody of the present invention are transformants derived from primary cultured cells and cell lines as described above. Examples of such transformants include: iPS cells produced from primary cultured cells; and cells and tissues differentiated from such iPS cells. Examples of other transformants include primary cultured cells and cell lines engineered to incorporate a gene so as to transiently or permanently express the gene. Examples of genes to be introduced into and expressed by such cells include IGF-I receptor genes of human and other species.

Methods for determining the cell proliferation-inducing activity by the antibody of the present invention in vertebrate-derived cells include: cell counting, measurement of DNA synthesis, and measurement of change in the metabolic enzyme activity. Methods for cell counting include methods using blood cell counting plates or cell counting devices such as Coulter counters. Methods for measuring DNA synthesis include methods based on uptake of [3H]-thymidine or 5-bromo-2'-deoxyulysine (BrdU). Method for measuring the change in metabolic enzyme activity include MTT method, XTT method, and WST method. A person skilled in the art could also employ other methods as appropriate.

The cell proliferation-inducing activity can be determined by that the proliferation of cultured cells reacted with the antibody of the present invention increases compared to that of cultured cells not reacted with the antibody. In this case, the inducing activity can favorably be normalized through the measurement using IGF-I, an original ligand of the IGF-I receptor, that is reacted under the same conditions as a control. An $EC_{50}$ value indicates a concentration at which 50% of the maximum proliferation-inducing activity is given in the case that the antibody of the present invention and IGF-I are reacted with various concentrations to the cultured cells. In the case that the proliferation-inducing activity is evaluated with human skeletal muscle myoblast cells, the antibody of the present invention has preferably an $EC_{50}$ value in the cell proliferation-inducing activity equivalent to that of IGF-I, more preferably an $EC_{50}$ value of 1/10 or less, further more preferably 1/20 or less, most preferably 1/50 or less that of IGF-I. In addition, in the case that the proliferation-inducing activity is evaluated with human skeletal muscle myoblast cells, the antibody of the present invention has an $EC_{50}$ value of preferably 0.5 nmol/L or less, more preferably 0.3 nmol/L or less, most preferably 0.1 nmol/L or less.

Methods for measuring the activity to induce growth of vertebrate-derived cells in vivo include: a method involving administering the antibody of the present invention to a vertebrate and measuring changes in the weight, size, cell count, etc., for the entire body of the individual which received the administration or for an organ or a tissue isolated from the individual; and a method involving using an animal with a graft of vertebrate cells and measuring changes in the weight, size, cell count, etc., of the graft including vertebrate cells. Measurements for the entire body of an individual include: measurements of the body weight, the body length, and the circumferences of four limbs; measurement of the body composition, using impedance method; and measurement of the creatinine height coefficient. Measurements for an organ, a tissue, or a graft from an individual include: in the case of a non-human animal, a method involving directly recovering the target organ, tissue or graft and measuring its weight, size, or the number of cells included therein. Non-invasive measurements for an organ, a tissue, or a graft from an individual include: image analysis using X-ray photography, CT, and MRI; and contrast methods using tracers with isotopes or fluorescent substances. If the target tissue is skeletal muscle, then a change in the muscle force can also be used as an indicator. A person skilled in the art could also employ any other methods as appropriate for analyzing the activity of the antibody of the present invention to induce growth of vertebrate-derived cells in vivo. Methods for measuring the activity of the antibody of the present invention to induce growth of vertebrate-derived cells in vivo include: carrying out measurements using, e.g., the methods mentioned above for individuals who received administration of the antibody of the present invention and individuals who received administration of a different antibody other than the antibody of the present invention or any other control substance, and comparing the resultant measurements between these individuals.

The antibody of the present invention is characterized by having a longer duration of cell proliferation-inducing effect relative to the time of contact with the cells compared to the duration of the wild-type IGF-I, and thereby exhibits improved sustainability. In in vitro cell proliferation-inducing activities, when cells were contacted with the wild-type IGF-I and then washed with culture medium without IGF-I, the cell proliferation induction activity of the wild-type IGF-I disappeared after the washing. On the other hand, when cells were contacted with IGF11-16 antibody (JP 2017-106529) which was a base of design of the antibody of the present invention and then washed with culture medium without IGF11-16, the cell proliferation-inducing activity continued even after the washing. In Example 8 described later, which compares the kinetics of IGF-I and R11-16B antibody (the antibody of the present invention) in blood, about 50% or higher of the wild-type IGF-I administered to an animal disappeared from the blood within 24 hours after the administration, while 60% or higher of the R11-16B antibody administered to an animal remained in the blood even 48 hours after the administration. Thus, the R11-16B antibody was shown to remain in the blood for a long time. These results indicate that the antibody of the present invention exhibits a long-term effect of inducing cell proliferation both in vitro and in vivo.

The antibody of the present invention is also expected to exhibit an in vivo effect of increasing the muscle mass and/or the body length. Specifically, IGF-I has an effect of inducing the growth and differentiation of myoblasts in skeletal muscles as mentioned above, as well as an effect of broadening muscle fibers. It is expected that these effects collectively lead to the effect of increasing the muscle mass. Like IGF-I, when the antibody of the present invention is administered to an animal, it also exhibits an effect of increasing the muscle mass of the animal. The antibody of the present invention is the first antibody which has been shown to exhibit an in vivo effect of increasing the muscle mass.

Methods for measuring the activity of the antibody of the present invention to increase the muscle mass include: for the entire body of the individual which received the administration, measurement of the body weight, the body length, and the circumferences of four limbs; measurement of the body composition, using impedance method; and measurement of the creatinine, and height coefficient. Other methods include: image analysis using X-ray photography, CT, and MRI; contrast methods using tracers with isotopes or fluorescent substances; and measurement of a change in the muscle force. In the case of a non-human animal, a method involving directly recovering the target organ, tissue or graft and measuring its weight and/or size can also be used. The effect of increasing the muscle mass can be evaluated by: comparing the muscle mass increases between an individual to which the antibody of the present invention was administered and an individual to which the antibody was not administered; or comparing the muscle masses of an individual before and after administration of the antibody of the present invention. The effect of increasing the muscle mass can be determined if there is any increase in the muscle mass of an individual before and after the administration of the antibody of the present invention. Preferably, the effect achieved by administration of the antibody of the present invention can be determined when there is a difference of preferably 103% or higher, more preferably 104% or higher of the muscle mass between an individual to which the antibody of the present invention was administered and an individual to which the antibody was not administered, or of the same individual between before and after administration of the antibody of the present invention. IGF-I also plays a role in the bone growth, and has an effect of increasing the body length (the body height in the case of the human). Therefore, the antibody of the present invention also exhibits an effect of increasing the body length when administered to an animal. The effect of the antibody of the present invention in increasing the body length of an individual can be determined by measuring the body weight, the body length, and the circumferences of four limbs of the individual.

[Effects on Glucose Uptake by Vertebrate-Derived Cells and/or Blood Glucose Level in Animal]

An antibody according to one embodiment of the present invention is characterized by not affecting glucose uptake into differentiated muscle cells derived from a vertebrate and/or blood glucose level in the vertebrate. IGF-I is known to cause an increase in the glucose uptake into the cells and a decrease in the blood glucose level as part of an agonistic effect on the IGF-I receptor. However, the inventive agonist antibody that functions as an IGF-I receptor agonist antibody has unexpected effects that the antibody does not induce the glucose uptake into differentiated muscle cells even at a dose of 100 times or more the in vitro $EC_{50}$ value in proliferation-inducing activity in vertebrate-derived cells, and does not vary the blood glucose level even at a blood exposure level of 10 times or more the effective dose that induces an increase in muscle mass in parenteral administration to the animal. In addition, the inventive antagonist antibody functioning as the IGF-I receptor antagonist antibody does not also affect the glucose uptake into differentiated muscle cells of vertebrate-derived cells and/or the blood glucose level in a vertebrate, resulting in an advantageous effect on avoidance of, for example, hyperglycemia, which has been an unsatisfactory problem for use of the conventional IGF-I receptor antagonist antibody in treatment for humans. The vertebrate-derived cells in the present disclosure are as described above.

In order to analyze the effect of the antibody of the present invention in not affecting the intracellular glucose uptake by vertebrate-derived cells in vitro, it is possible to use primary cultured cells, cell lines, and transformants derived from such cells. The primary cultured cells, established cells, and transformant cells in the present disclosure are as described above.

Examples of methods for determining the effect of the antibody of the present invention on the glucose uptake by vertebrate-derived cells include: measurement of the intracellular glucose concentration; measurement of the intracellular uptake of a glucose analog tracer substance; and measurement of a change in the amount of a glucose transporter. Methods for measuring the glucose concentration include absorbance measurement methods such as enzyme method. Methods for measuring the intracellular uptake amount of a glucose analog tracer substance include measurement of the uptake amount of [3H]-2'-deoxyglucose. Methods for measuring a change in the amount of a glucose transporter include immunocytostaining and western blotting. A person skilled in the art could also employ other methods as appropriate. The fact that there is no effect on the intracellular glucose uptake can be confirmed if the intracellular glucose uptake of the cultured cells reacted with the antibody of the present invention is almost the same of the intracellular glucose uptake of the cultured cells in the absence of the antibody. In this case, it is convenient to also carry out the measurement under the same conditions using IGF-I, which is an original legend for the IGF-I receptor, as a control.

The cultured cells to be tested are treated with either the antibody of the present invention or IGF-I with varying its concentration, and the glucose uptake of the treatment group is indicated as a percentage when the intracellular glucose uptake of the non-treatment group is determined as 100%. When human differentiated muscle cells are used for evaluating the glucose uptake, the glucose uptake achieved by the antibody of the present invention should preferably be equal to or less than the glucose uptake achieved by IGF-I at the same concentration. More preferably, the glucose uptake achieved by the antibody of the present invention should be 110% or less, still more preferably 100%, of the glucose uptake amount of the non-treatment group. When human differentiated muscle cells are used for evaluating the glucose uptake, the glucose uptake achieved by the antibody of the present invention added at an amount of 100 nmol/L should preferably be 110% or less, more preferably 105% or less, still more preferably from 95% to 100%.

Methods for determining the glucose uptake by vertebrate-derived cells in vivo include: methods involving parenterally administering the antibody of the present invention to a vertebrate and determining a change in the glucose content of an organ or a tissue of the individual. Methods of measurement for the entire body of the individual which received the administration include: measurement of the blood glucose level; and hemoglobin A1C using glycosylated proteins as indicators. Methods of measuring the glucose uptake for an organ or a tissue of an individual include: in the case of a non-human animal, directly recovering the target organ or tissue, and calculating the concentration of glucose or a tracer. Non-invasive methods for measuring the glucose uptake individual for an organ or a tissue of an individual include: image analysis using X-ray photography, CT, and MRI; and contrast methods using tracers with isotopes or fluorescent substances. If the target tissue is a skeletal muscle, then the glucose clamp can also be used as an indicator. A person skilled in the art could also employ any other methods as appropriate for analyzing the effect of the antibody of the present invention on the glucose uptake by vertebrate-derived cells in vivo.

The antibody of the present invention is also characterized in that when administered to a vertebrate even at an effective dosage sufficient to increase the muscle mass of the vertebrate, preferably at a dosage of 10 times or more the effective dosage, it does not change the blood glucose level of the vertebrate. When evaluating the effect of the antibody of the present invention in changing the blood glucose level of a vertebrate, it is preferred to use an animal belonging to mammals, birds, reptiles, amphibia or fish, more preferably an animal belonging to mammals or birds, still more preferably human, monkey, rabbit, guinea pig, cow, pig, sheep, horse or dog. An animal engineered to express an IGF-I receptor of a species which has cross-reactivity with the antibody of the present invention can also be used as an animal for evaluating the effect of the antibody of the present invention in changing the blood glucose level. Invasive methods for measuring the blood glucose level include colorimetric method and electrode method. Examples of enzyme methods used for detection include glucose oxidase method (GOD method) and glucose dehydrogenase method (GDH method). Non-invasive methods include optical measurement methods. A person skilled in the art can also select any other method as appropriate. In the case of human, the normal range of fasting blood glucose level is from 100 mg/dL to 109 mg/dL. With regard to adverse events in the blood glucose level resulting from a drug administration (Common Terminology Criteria for Adverse Events v4.0), the blood glucose level of lower than the range of from 77 mg/dL to 55 mg/dL is defined as an indicative of low blood glucose, while a blood glucose level of higher than the range of from 109 mg/dL to 160 mg/dL is defined as an indicative of high blood glucose. A drug administration is considered as not affecting the blood glucose level when the blood glucose level after the drug administration is higher than 55 mg/dL and lower than 160 mg/dL, more preferably higher than 77 mg/dL and lower than 109 mg/dL. However, the normal value of blood glucose level and its range of fluctuation vary depending on the animal to which a drug is administered, and even a human subject may not always have a blood glucose level within a normal range at the time of the drug administration. Accordingly, in the context of the present invention, the antibody of the present invention should preferably be considered as not changing the blood glucose level of a vertebrate to which the antibody is administered when the change in the blood glucose level of the vertebrate is preferably 30% or less, more preferably 20% or less, still more preferably 10% or less.

[Process for Producing Anti-IGF-I Receptor Humanized Antibody]

The antibody of the present invention can be produced by humanization of a mouse monoclonal antibody IGF11-16 (a mouse IGF11-16 antibody, JP 2017-106529) to an IGF-I receptor. An example method of producing the humanized antibody is illustrated in Example 1 described later, and humanized antibodies produced by such a method include, but are not limited to, humanized antibodies (R11-16B, R11-16C, R11-16D, R11-16E or R11-16F) each having a VH amino acid sequence of SEQ ID NO: 7 and a VL amino acid sequence of SEQ ID NOs: 8, 9, 10, 11 or 12.

A nucleic acid molecule having a base sequence encoding the amino acid of the protein in the resultant anti-IGF-I receptor humanized antibody can be produced, and such a nucleic acid molecule is also genetically engineered to produce an antibody. The H chain, L chain, or their variable regions in gene information of the antibody can be modified to improve the avidity and specificity of the antibody with reference to information of, for example, CDR sequences.

In a method of producing the antibody of the present invention, for example, mammalian cells, insect cells, and *Escherichia coli* into which genes encoding the amino acids of proteins in target antibodies are introduced are cultured, and thereby the antibody can be produced through purification of the resultant culture supernatant by a conventional process. Any specific method is illustrated below.

A nucleic acid molecule encoding an H chain variable region is bound to a nucleic acid molecule encoding an H chain signal peptide and a nucleic acid molecule encoding an H chain constant region to produce the antibody of the present invention. A nucleic acid molecule encoding an L chain variable region is bound to a nucleic acid molecule encoding an L chain signal peptide and a nucleic acid molecule encoding an L chain constant region to produce the antibody of the present invention.

These H chain gene and L chain gene are incorporated into a vector, for example, a cloning vector or an expression vector, suitable for expression in a selected host cell. In this case, the H chain gene and the L chain gene may be incorporated into one vector or separate vectors such that both genes can be expressed.

The vector into which the H chain gene and the L chain gene are incorporated is then introduced into the host cell. Examples of host cells include eukaryotic cells, such as mammalian cells, insect cells, yeast cells or plant cells, and bacterial cells. A method of introducing the genes into the host cell may be appropriately selected from a chemical method such as calcium phosphate process or a lipofection process, a physical method such as an electroporation process or a particle gun process, and a method based on infection with a virus or a phage. The host cell into which the H chain gene and L chain gene are introduced can be used in culturing without any selection, selectively condensing of recombinant cells into which the genes are introduced using properties of, for example drug resistance and auxotrophy, or culturing of recombinant clone cells constructed from a single host cell into which the genes are introduced.

The host cell into which the H chain gene and L chain gene are introduced is cultured under an optimum medium and culturing condition. In this process, the products of the H chain gene and the L chain gene expressed in the host cell are usually secreted into the medium as antibody proteins, and the produced antibody proteins can be recovered by collecting the medium. However, through combining of the genes and the host cell, the antibody proteins accumulated in the cell can be recovered by destruction of the host cell as needed, or the antibody proteins can be recovered from a periplasm fraction in the case of a prokaryotic cell. Examples of methods generally used for purifying an antibody from a sample such as a medium containing the recovered antibody proteins include salt precipitation; enrichment or solvent exchange by dialysis and ultrafiltration; and affinity chromatography using a carrier that contains, for example, immobilized protein A, protein G, or antigen. Also available are ion exchange chromatography, hydrophobic chromatography, mixed mode chromatography, and size exclusion chromatography. A variety of techniques used in these methods is well known to those skilled in the art.

In this connection, a person skilled in the art can produce various antibodies such as antibody chimeric proteins, low molecule antibodies, and scaffold antibodies using known techniques, e.g., by making a genetic modification to a gene encoding a heavy chain and/or a light chain of an immunoglobulin for introducing a desired trait, or by using structure information of variable regions or CDR regions of a heavy chain and/or a light chain of an immunoglobulin. In addition, in order to improve the performance of the antibody or avoiding side effects, it is possible to introduce a modification into the structure of a constant region of an antibody or to introduce glycosylation sites of an antibody, using techniques well-known to persons skilled in the art as appropriate.

[Drug Containing the Anti-IGF-I Receptor Humanized Antibody]

The antibody of the present invention can be used as a therapeutic or prophylactic agent for a condition associated with IGF-I or a disease caused by any effect on an IGF-I receptor. Specifically, conditions associated with IGF-I or diseases that can be the target of therapy or prevention using the IGF-I receptor agonist antibody include: muscular atrophy disease (e.g., disuse muscle atrophy, sarcopenia and cachexia), dwarfism (e.g., Laron type dwarfism and growth hormone resistant dwarfism), hepatic cirrhosis, hepatic fibrosis, diabetic nephropathy, chronic renal failure, aging, intrauterine growth restriction (IUGR), cardiovascular protection, diabetes, insulin resistant, metabolic syndrome, osteoporosis, cystic fibrosis, myotonic dystrophy, AIDS-associated sarcopenia, HIV-associated fat redistribution syndrome, Crohn's disease, Werner's syndrome, X-linked combined immunodeficiency disease, hearing loss, anorexia nervosa and retinopathy of prematurity, Turner's syndrome, Prader-Willi syndrome, Silver-Russell syndrome, idiopathic dwarfism, obesity, multiple sclerosis, ulcerous colitis, low muscle mass, myocardial ischemia, and decreased bone density. Diseases that can be the target of therapy or prevention using the IGF-I receptor antagonist antibody include: neuroblastoma, striated muscle sarcoma, bone cancer, childhood cancer, acromegalia, ovary cancer, pancreas cancer, benignant prostatic hypertrophy, breast cancer, prostate cancer, bone cancer, lung cancer, colorectal cancer, cervix cancer, synovial sarcoma, urinary bladder cancer, stomach cancer, Wilms' tumor, diarrhea associated with metastatic carcinoid and vasoactive intestinal peptide secreting tumor, vipoma, Verner-Morrison syndrome, Beckwith-Wiedemann syndrome, kidney cancer, renal cell cancer, transitional cell cancer, Ewing's sarcoma, leukemia, acute lymphoblastic leukemia, brain tumor, glioblastoma, nonglioblastomatic brain tumor, meningioma, pituitary adenoma, vestibular schwannoma, primitive neuroectodermal tumor, medulloblastoma, astrocytoma, oligodendroglioma, ependymoma, choroid plexus papilloma, gigantism, psoriasis, atherosclerosis, vascular smooth muscle restenosis, inappropriate microvascular growth, diabetic retinopathy, Graves' disease, systemic lupus erythematosus, Hashimoto's thyroiditis, myasthenia gravis, autoimmune thyroiditis, and Behcet's disease. Particularly preferred uses of the antibody of the present invention include use as a therapeutic or prophylactic agent of muscular atrophy disease (e.g., disuse muscle atrophy, sarcopenia and cachexia) and/or dwarfism (e.g., Laron type dwarfism and growth hormone resistant dwarfism). The antibody of the present invention is advantageous in that it does not change the blood glucose level upon administration.

A drug containing the antibody of the present invention may be formulated in the form of a pharmaceutical composition which contains, in addition to the antibody of the present invention, a pharmaceutically acceptable carrier and/or any other excipient. Drug formulation using a pharmaceutically acceptable carrier and/or any other excipient can be carried out in accordance with, e.g., a method described in the University of the Sciences in Philadelphia, "Remington: The Science and Practice of Pharmacy, 20th EDITION", Lippincott Williams & Wilkins, 2000.

Such a therapeutic or prophylactic agent may be provided as a liquid formulation prepared by dissolving, suspending, or emulsifying the ingredients into sterile aqueous medium or oily medium, or as a lyophilized formulation thereof. A medium or solvent for preparing such a formulation may be an aqueous medium, examples of which include distilled water for injection and physiological saline solution, which may optionally be used with addition of an osmoregulating agent (e.g., D-glucose, D-sorbitol, D-mannitol, and sodium chloride), and/or in combination with a suitable dissolving aid such as an alcohol (e.g., ethanol), a polyalcohol (e.g., propylene glycol or polyethylene glycol), or a nonionic surfactant (e.g., polysorbate 80 or polyoxyethylene hydrogenated castor oil 50). Such a formulation can also be prepared with an oily medium or solvent, examples of which include sesame oil and soybean oil, which can optionally be used in combination with a dissolving aid such as benzyl benzoate and benzyl alcohol. Such liquid drugs may often be prepared using appropriate additives such as buffering agents (e.g., phosphate buffering agents and acetate buffering agents), soothing agents (e.g., benzalkonium chloride and procaine hydrochloride), stabilizers (e.g., human serum albumin and polyethylene glycol), preservatives (e.g., ascorbic acid, erythorbic acid, and their salts), coloring agents (e.g., copper chlorophyll β-carotene, Red #2 and Blue #1), antiseptic agents (e.g., paraoxybenzoic acid esters, phenol, benzethonium chloride and benzalkonium chloride), thickeners (e.g., hydroxypropyl cellulose, carboxymethyl cellulose, and their salts), stabilizers (e.g., human serum albumin mannitol and sorbitol), and odor correctives (e.g., menthol and citrus aromas).

Other alternative forms include therapeutic agents or prophylactic agent for application onto mucous membranes, such formulations often containing additives such as pressure-sensitive adhesives, pressure-sensitive enhancers, viscosity regulators, thickening agents and the like (e.g., mucin, agar, gelatin, pectin, carrageenan, sodium alginate, locust bean gum, xanthan gum, tragacanth gum, gum arabic, chitosan, pullulan, waxy starch, sucralfate, cellulose and its derivatives (such as hydroxypropyl methyl cellulose), polyglycerol fatty acid esters, acrylic acid-alkyl (meth) acrylate copolymers, or their salts and polyglycerol fatty acid esters), primarily for the purpose of imparting mucosal adsorption or retention properties. However, the form, solvent and additives for the therapeutic agent or prophylactic agent to be administered to the body are not limited to these, and appropriately selection may be made by a person skilled in the art.

A drug containing the antibody of the present invention may further contain, in addition to the antibody of the present invention, another known agent (active ingredient). A drug containing the anti-IGF-I receptor antibody of the present invention may be combined with another known agent in the form of a kit. Examples of active ingredients to be combined with the IGF-I receptor agonist antibody include: growth hormone or an analog thereof, insulin or an analog thereof, IGF-II or an analog thereof, an anti-myostatin antibody, myostatin antagonist, anti-activin type IIB receptor antibody, activin type IIB receptor antagonist, soluble activin type IIB receptor or an analog thereof, ghrelin or an analog thereof, follistatin or an analog thereof, a beta-2 agonist, and a selective androgen receptor modulator. Examples of active ingredients to be combined with the IGF-1 receptor antagonist antibody include: corticosteroid, antiemetic, ondansetron hydrochloride, granisetron hydrochloride, metoclopramide, domperidone, haloperidol, cyclizine, lorazepam, prochlorperazine, dexamethasone, levomepromazine, tropisetron, cancer vaccine, GM-CSF inhibitor, GM-CSF DNA vaccine, cell-based vaccine, dendritic cell vaccine, recombinant virus vaccine, heat shock protein (HSP) vaccine, homologous tumor vaccine, autologous tumor vaccine, analgesic, ibuprofen, naproxen, choline magnesium trisalicylate, oxycodone hydrochloride, anti-angiogenic, antithrombotic, anti-PD-1 antibody, nivolumab, pembrolizumab, anti-PD-L1 antibody, atezolizumab, anti-CTLA4 antibody, ipilimumab, anti-CD20 antibody, rituximab, anti-HER2 antibody, trastuzumab, anti-CCR4 antibody, mogamulizumab, anti-VEGFantibody, bevacizumab, anti-VEGF receptor antibody, soluble VEGF receptor fragment, anti-TWEAK antibody, anti-TWEAK receptor antibody, soluble TWEAK receptor fragment, AMG 706, AMG 386, antiproliferative, farnesyl protein transferase inhibitor, alpha v beta 3 inhibitor, alpha v beta 5 inhibitor, p53 inhibitor, Kit receptor inhibitor, ret receptor inhibitor, PDGFR inhibitor, growth hormone secretion inhibitor, angiopoietin inhibitor, tumor-infiltrating macrophage inhibitor, c-fms inhibitor, anti-c-fms antibody, CSF-1 inhibitor, anti-CSF-1 antibody, soluble c-fms fragment, pegvisomant, gemcitabine, panitumumab, irinotecan, and SN-38. The dosage of the other agent used in combination with the antibody may be within a dosage used for normal therapy, but can be increased or decreased depending on the situation.

The therapeutic or prophylactic agent according to the present invention can be parenterally administered for the purpose of improving symptoms. For parenteral administration, a transnasal agent may be prepared, and a liquid drug, suspension or solid formulation may be selected. An injection may be prepared as a different form of parenteral administration, the injection being selected as subcutaneous injection, intravenous injection, infusion, intramuscular injection, intracerebroventricular injection or intraperitoneal injection. Other formulations used for parenteral administration include suppositories, sublingual agents, percutaneous agents and transmucosal administration agents other than transnasal agents. In addition, intravascular local administration is possible by a mode of addition or coating onto a stent or intravascular obturator.

The dose for an agent for treatment or prevention according to the invention will differ depending on the patient age, gender, body weight and symptoms, the therapeutic effect, the method of administration, the treatment time, or the types of active ingredients in the medical composition, but normally it may be administered in the range of 0.1 mg to 1 g and preferably in the range of 0.5 mg to 300 mg of active compound per administration for adults, once every one to four weeks, or once every one to two months. However, since the administration dose and frequency will vary depending on a variety of conditions, lower administration dose and fewer administration frequency than those mentioned above may be sufficient, or administration dose and frequency exceeding these ranges may be necessary.

[Method for Culturing Cells Using the Anti-IGF-I Receptor Humanized Antibody]

IGF-I and its derivatives are widely used in cell culture techniques for maintaining, growing, and/or differentiating vertebrate-derived cells in vitro, and commercially marketed as cell culture reagents. However, since IGF-I can lose its effects during long-term culturing due to, e.g., its lack of enough stability, it is necessary to, e.g., keep adjusting the concentration thereof in order to carry out cell culturing stably. In addition, since IGF-I induces glucose uptake by cells, there is a possibility that the metabolism and characteristics of the cells may be changed due to an increase in the intracellular glucose concentration, and that the culture conditions may change due to a decrease in the glucose concentration of the culture medium. Compared to IGF-I, the antibody of the present invention is characterized in that it is more stable, can maintain its cell proliferation effect even after contact with cells, can exhibit an activity to induce cell proliferation even at a lower concentration, and does not induce intracellular glucose uptake. The anti-IGF-I receptor antibody of the present invention can be used for cell culturing, by adding an appropriate amount of the antibody to culture medium or by adsorbing or immobilizing an appropriate amount of the antibody to a solid phase of a culture vessel. Thus, the antibody of the present invention makes it possible to reduce the amount to be used, and effectively induce proliferation of cells adhering to the solid phase. The vertebrate-derived cells in the present disclosure are as described above. More specifically, examples of subjects that can be cultured using the antibody of the present invention also include an organ or a tissue of a vertebrate or a transgenic animal derived from such a vertebrate. The antibody of the present invention can be used for culturing cells for the purposes of cellular production of a substance or cell therapy and regeneration medicine using such cells.

EXAMPLES

The present invention will now be described in more detail by way of the following Examples. The present invention is not construed to be limited to these Examples, and may be implemented in any form without departing from the spirit of the present invention.

Example 1: Production of Humanized Antibody Gene of Mouse IGF11-16 Antibody

A template human antibody was selected from germ lines of human antibodies having amino acid sequences highly homologous to those of framework regions (FR) in the heavy chain variable region (VH) and light chain variable region (VL) of a mouse IGF11-16 antibody, where amino acids of the complementarity-determining region (CDR) in the VH and VL of a mouse monoclonal antibody IGF11-16 (a mouse IGF11-16 antibody disclosed in JP 2017-106529) to IGF-I receptors prepared by the hybridoma method of Kohler et al. (Nature, 256: 495-497, 1975) were to be transplanted into the template human antibody.

The required amino acid sequences from the VH and VL of the mouse IGF11-16 antibody were transplanted into the FR in the VH and VL of the template human antibodies to prepare humanized antibodies. In detail, the CDR amino acid sequence and several positions in FR amino acid sequence in the VH of the template human antibody were replaced with the corresponding amino acid sequences in the VH of the mouse IGF11-16 antibody to design an amino acid sequence of R11-16VH (SEQ ID NO: 7), which was the VH that the mouse IGF11-16 antibody was humanized, and to further design the base sequence of DNAs encoding these amino acids.

The CDR amino acid sequence and several positions in FR amino acid sequence in the VL of the template human antibody were replaced with the amino acid sequences in the VL of the mouse IGF11-16 antibody to design the amino acid sequence of R11-16VL, which was the VL that the mouse IGF11-16 antibody was humanized.

The amino acid at position 36 in R11-16VL was cysteine in the mouse IGF11-16 antibody. However, cysteine is rarely present at this position in normal human antibody. Since generation of a disulfide bond that does not originally generate probably results in aggregation, five amino acid sequences of R11-16VLs, i.e., R11-16VL-C36, R11-16VL-C36Y, R11-16VL-C36A, R11-16VL-C36S, and R11-16VL-C36F (SEQ ID NO: 12, SEQ ID NO: 8, SEQ ID NO: 9, SEQ ID NO: 10, SEQ ID NO: 11), each consisting of cysteine, tyrosine, alanine, serine, or phenylalanine at position 36 were designed, and the base sequences of DNAs encoding these amino acids were further designed. The structure of the humanized antibodies and their amino acid sequences are shown in Table 1.

[Table 1]

TABLE 1

Structures and amino acid sequences of produced humanized antibodies

| Name of antibody | Heavy chain variable region | Light chain variable region |
|---|---|---|
| R11-16B | R11-16VH SEQ ID NO: 7 | R11-16VL-C36Y SEQ ID NO: 8 |
| R11-16C | R11-16VH SEQ ID NO: 7 | R11-16VL-C36A SEQ ID NO: 9 |
| R11-16D | R11-16VH SEQ ID NO: 7 | R11-16VL-C36S SEQ ID NO: 10 |
| R11-16E | R11-16VH SEQ ID NO: 7 | R11-16VL-C36F SEQ ID NO: 11 |
| R11-16F | R11-16VH SEQ ID NO: 7 | R11-16VL-C36 SEQ ID NO: 12 |

Example 2: Preparation of Humanized Antibody

DNAs encoding the heavy chain variable region R11-16VH of the designed humanized antibody and DNAs encoding a human IgG4S228P variant that stabilized the human IgG4 subclass were synthesized, incorporated and ligated into a pCAGGS1 expression vector to form a plasmid expressing the heavy chain of humanized antibody.

Regarding the light chain variable region R11-16VL of the designed humanized antibody, DNAs encoding the light chain region of the humanized antibody ligated to a kappa chain constant region were synthesized and incorporated into a pCAGGS1 expression vector to form a plasmid expressing the light chain of humanized antibody.

The plasmid expressing the heavy chain and the plasmid expressing the light chain of the humanized antibody were mixed and introduced into cells using an Expi293™ Expression System (Thermo Fisher Scientific), and thereby various antibodies prepared by humanization of the mouse IGF11-16 antibody were expressed. These antibodies are named an R11-16B antibody, an R11-16C antibody, an R11-16D antibody, an R11-16E antibody, and an R11-16F antibody, respectively: the R11-16B antibody was a humanized antibody expressed by combination of a heavy chain expression plasmid incorporating R11-16VH and a light chain expression plasmid incorporating R11-16VL-C36Y; the R11-16C antibody was a humanized antibody expressed by combination of a heavy chain expression plasmid incorporating R11-16VH and a light chain expression plasmid incorporating R11-16VL-C36A; the R11-16D antibody was a humanized antibody expressed by combination of a heavy chain expression plasmid incorporating R11-16VH and a light chain expression plasmid incorporating R11-16VL-C36S; the R11-16E antibody was a humanized antibody expressed by combination of a heavy chain expression plasmid incorporating R11-16VH and a light chain expression plasmid incorporating R11-16VL-C36F; and the R11-16F antibody was a humanized antibody expressed by combination of a heavy chain expression plasmid incorporating R11-16VH and a light chain expression plasmid incorporating R11-16VL-C36. The humanized antibodies were yielded by affinity purification of the culture supernatant of the cell into which the plasmids expressing the heavy chain and the light chain of humanized antibody were introduced through a protein A column.

Example 3: Avidity to IGF-I Receptor (ELISA)

The avidities of the IGF-I receptor agonist antibodies to IGF-I receptors of human (SEQ ID NO: 14, NP_000866), guinea pig (SEQ ID NO: 16, XP_003475316), cynomolgus monkey (SEQ ID NO: 18, XP_005560575) and rat (SEQ ID NO: 20, NP_434694) were examined using cells in which the IGF-I receptors were expressed by a cell-based ELISA.

pEF1 expression vectors (Thermo fisher) into which IGF-I receptor genes of human (SEQ ID NO: 15), guinea pig (SEQ ID NO: 17), cynomolgus monkey (SEQ ID NO: 19) and rat (SEQ ID NO: 21) were incorporated were introduced into HEK293T cells by lipofection. The HEK293T cells cultured for at least one night after the lipofection were added to a 96-well plate (coated with poly-D-lysine) in $4 \times 10^4$ cells/well, and the plate further cultured for at least one night were used in the ELISA.

In the ELISA, 2 nM humanized antibody solutions in 1% BSA/1% FBS/PBS (100 µL) were added to respective wells and reacted for about one hour at 37° C. The wells were washed three times with a cleaning solution. An HRP conjugate solutions (100 µL) of an anti-human IgG antibody prepared at various concentrations with 1% BSA/1% FBS/PBS was added to the respective wells and reacted for about one hour at 37° C. Each well was washed three times with a cleaning solution. A TMB substrate (100 µL) was added to each well to initiate the reaction. Approximately 30 minutes later, 1 M sulfuric acid (100 µL) was added to each well to measure the absorbances at 450 nm and 650 nm and calculate the difference of the values between 450 nm and 650 nm. The avidity was calculated based on the difference between the absorbance at 450 nm and 650 nm for cells not containing the IGF-I receptor gene, which were HEK293T cells (i.e., control cells), as a standard value 1. The results are shown in Table 2.

[Table 2]

TABLE 2

Avidity* of humanized antibodies to various IGF-I receptors

| Humanized antibody | Human | Cynomolgus monkey | Guinea pig | Rat |
|---|---|---|---|---|
| R11-16B | 3.4 | 3.3 | 3.3 | 0.8 |
| R11-16C | 3.4 | 3.3 | 3.3 | 0.9 |
| R11-16D | 3.4 | 3.4 | 3.3 | 0.9 |
| R11-16E | 3.7 | 3.7 | 3.4 | 0.8 |
| R11-16F | 3.4 | 3.3 | 3.3 | 0.9 |

*The avidity was relative value to the standard value 1 of the control cells (HEK293T).

In the cells expressing IGF-I receptors of human, cynomolgus monkey and guinea pig, each humanized antibody exhibited an avidity that is three or more times that of the control cells (HEK293T). In contrast, the avidity to the cells expressing IGF-I receptor of rat was equivalent to that of the control cells. These results indicate that each humanized antibody bound to the IGF-I receptors of human, cynomolgus monkey, and guinea pig, but not to the IGF-I receptor of rat.

Example 4: Determination of Epitope in Humanized Antibody R11-16B

The humanized antibody R11-16B bound to the IGF-I receptors of human, cynomolgus monkey, and guinea pig, but not to the IGF-I receptor of rat. In addition, the mouse IGF11-16 antibody, which was the mouse antibody (JP 2017-106529) that served as the base for designing of R11-16B, bound to the CR domain in the human IGF-I receptor, but not to that in the rat IGF-I receptor. It is presumed from these results that the epitope of R11-16B has an amino acid sequence common to human, cynomolgus monkey and guinea pig, and an amino acid sequence different from rat among the amino acid sequences of the CR domains in the IGF-I receptors.

The avidity of the CR domain to various amino acid substitutes were measured by an ELISA to determine which position of the amino acid in the CR domain of the human IGF-I receptor the R11-16B bound to. A cell-based ELISA was performed using cells expressing IGF-I receptors in which the amino acid sequence expected to bind to the R11-16B in the CR domain was mutated.

Two amino acid substitutes in the CR domain were used as described below. A positive control used was a pEF1 expression vector (Thermo fisher) that incorporated a DNA encoding the amino acid sequence (SEQ ID NO: 22) in which a FLAG tag (AspTyrLysAspAspAspAspLys: SEQ ID NO: 29) was bound to the C-terminal of a wild-type human IGF-I receptor (SEQ ID NO: 14, NP_000866). Cells including the pEF1 expression vector alone were designated as Mock.

(Substitute 1 of CR Domain)

In the amino acid sequence of human IGF-I receptor (SEQ ID NO: 14, NP_000866), aspartic acid, alanine, and glutamic acid, respectively, at positions 245, 247 and 294 are replaced with asparagine, threonine and aspartic acid. A DNA (SEQ ID NO: 23) encoding an amino acid sequence in which a FLAG tag was bound to the C-terminal of the amino acid sequence of the substitute 1 receptor was incorporated into the pEF1 expression vector.

(Substitute 2 of CR Domain)

In the amino acid sequence of the human IGF-I receptor (SEQ ID NO: 14, NP_000866), glycine and serine, respectively, at positions 315 and 316 were replaced with serine and threonine. A DNA (SEQ ID NO: 24) encoding an amino acid sequence in which a FLAG tag was bound to the C-terminal of the amino acid sequence of the substitute 2 receptor was incorporated into the pEF1 expression vector.

293T cells were seeded in 10-cm dishes coated with poly-D-lysine in $6 \times 10^6$ cells. On the next day, each plasmid DNA was introduced into the cells by lipofection. Two days later, the 293T cells were released with 0.05% trypsin/EDTA and suspended in the culture medium. The 293T cells were added to a 96-well plate (coated with poly-D-lysine) in $2 \times 10^4$ cells/well and incubated overnight at 37° C. under 5% $CO_2$. The medium was removed from the 96-well plate. The plate was fixed with 10% buffered formalin (MILDFORM® 10NM, Wako), replaced by a blocking buffer (3% BSA/PBS/0.02% sodium azide), and used for the ELISA.

In the ELISA, a solution of 5 nM R11-16B in the blocking buffer (50 μL) was added to each well and reacted for about one hour at room temperature. Each well was washed two times with a cleaning solution. A 2500-fold diluted solution of an anti-human IgG antibody ALP conjugate solution (2087-04, Southern Biotech) in the blocking buffer (50 μL) was added to each well and reacted for about one hour at room temperature. Each well was washed three times with a cleaning solution. A pNPP substrate (100 μL) was added to each well to initiate the reaction. The absorbances at 405 nm and 550 nm were measured after about one hour. The value given by subtracting the value of the unadded group of R11-16B from the value of the added group of R11-16B was determined as the avidity. The results are shown in Table 3.

[Table 3]

TABLE 3

Avidity of R11-16B to human IGF-I receptor and amino acid substitutes thereof

|  | Mock | Human IGF-I receptor | Substitute 1 | Substitute 2 |
|---|---|---|---|---|
| Avidity | 0.328 | 0.835 | 0.885 | 0.308 |

The avidity of R11-16B to the human IGF-I receptor is two or more times that to Mock. The avidity to substitute 1 is equivalent to that to the human IGF-I receptor. In contrast, the avidity to substitute 2 is equivalent to that to Mock, indicating no enhancement in avidity. These results indicate that the amino acids at positions 315 and 316 of the IGF-I receptor are essential for the avidity of R11-16B to the human IGF-I receptor.

These results suggest that the binding position of R11-16B to the human IGF-I receptor lies in the vicinity of Gly (glycine) and Ser (serine) at positions 315 and 316, respectively. In general, based on the recognition sequence number of eight amino acid residues (mean value of six to ten residues) by the antibody and the cross-reactivity of R11-16B (having no avidity to the rat IGF-I receptor, and having avidity to IGF-I receptors of human and guinea pig), the sequence of human IGF-I receptor at binding positions to the R11-16B was believed to be ProSerGlyPheIleArgAsnGly*Ser*GlnSerMet (SEQ ID NO: 30) (Gly*Ser* indicates the amino acid sequence at positions 315 and 316).

Example 5: Cell Proliferation Activity on Human Myoblast Cells

Various agents were added to human myoblast cells, and the ATP content in the cells was measured after four days to examine the proliferation activity of an IGF-I receptor agonist antibody on the human myoblast cells.

Normal human skeletal muscle myoblast cells (HSMM, Lonza) were seeded onto a 96-well plate (Collagen type I coated) in 0.1 mL/well ($2 \times 10^3$ cells/well) using an SkBM-2 medium (CC-3246, Lonza) containing 1% BSA, and the plate was incubated at 37° C. under 5% $CO_2$. On the next day after seeding of the cells, various agents were added in 25 μL/well, and the plate was incubated for four days at 37° C. under 5% $CO_2$. The ATP content in the cells as an indicator of cell proliferation was measured by CellTiter-Glo® luminescent cell viability assay (Promega). The supernatant was removed from the 96-well plate incubated for four days such that the culture solution reached 50 μL/well, and the plate was left to stand for 30 minutes or more at room temperature. The CellTiter-Glo® reagent was added to the plate in 50 μL/well and reacted for ten minutes or more, and then the luminescence signal was measured with a luminometer (Berthold). The proliferation activity on human myoblast cells was calculated where the activity of the group to which a vehicle was added alone was defined to be 100%. The results are shown in Tables 4 to 6.

[Table 4]

TABLE 4

Proliferation activity on human myoblast cells in the case of addition of various agents in 0.5 nM

| Agent | Proliferation activity on human myoblast cells (%) |
|---|---|
| R11-16B | 135 |
| Mouse IGF11-16 antibody | 137 |
| IGF-I | 123 |

Addition of R11-16B in an amount of 0.0000005, 0.000005, 0.00005, 0.0005, 0.005, 0.05, 0.5, 5, or 50 nM enhanced the proliferation activity on human myoblast cells depending on the concentration. The $EC_{50}$ values of proliferation activity of R11-16B, mouse IGF11-16 antibody and IGF-I on human myoblast cells were 0.002, 0.002 and 0.95 nM, respectively. The activity of R11-16B was equivalent to that of a mouse IGF11-16 antibody and was 100 times or more higher than that of the IGF-I.

[Table 5]

TABLE 5

Proliferation activity on human myoblast cells in the case of addition of various agents in 0.5 nM and 0.005 nM

| Agent | Concentration (nM) | Proliferation activity on human myoblast cells (%) | |
|---|---|---|---|
|  |  | Experiment 1 | Experiment 2 |
| IGF-I | 0.005 | 108 | 110 |
| R11-16B |  | 147 | 148 |
| R11-16C |  | 150 | 143 |
| R11-16D |  | 144 | 149 |
| R11-16E |  | 150 | 143 |
| R11-16F |  | 146 | 148 |
| IGF-I | 0.5 | 133 | 125 |
| R11-16B |  | 164 | 164 |
| R11-16C |  | 178 | 172 |

TABLE 5-continued

Proliferation activity on human myoblast cells in the case of addition of various agents in 0.5 nM and 0.005 nM

| Agent | Concentration (nM) | Proliferation activity on human myoblast cells (%) | |
|---|---|---|---|
| | | Experiment 1 | Experiment 2 |
| R11-16D | | 160 | 169 |
| R11-16E | | 166 | 164 |
| R11-16F | | 161 | 156 |

Addition of R11-16B, R11-16C, R11-16D, R11-16E, R11-16F in an amount of 0.00005, 0.0005, 0.005, 0.05, 0.5, 5, or 50 nM enhanced the proliferation activity on human myoblast cells depending on the concentration. All the $EC_{50}$ values of proliferation activity of R11-16B, R11-16C, R11-16D, R11-16E and R11-16F on human myoblast cells were 0.002 nM. Each humanized antibody had high activity that was 100 times or more that of IGF-I.

[Table 6]

TABLE 6

Proliferation activity on human myoblast cells in the case of addition of various agents in 0.5 nM and 0.005 nM

| Agent | Concentartion (nM) | Experiment 1 Cell proliferation activity (%) | Experiment 2 Cell proliferation activity (%) |
|---|---|---|---|
| Control antibody (FLAG M2 antibody) | 0.005 | 99 | — |
| IGF-I | 0.005 | 102 | 103 |
| R11-16B | 0.005 | — | 127 |
| 16-13 | 0.005 | — | 102 |
| 26-3 | 0.005 | — | 108 |
| Vehicle control 1* (containing sodium azide) | — | — | 104 |
| Control antibody (FLAG M2 antibody) | 0.5 | 98 | — |
| IGF-I | 0.5 | 133 | 137 |
| R11-16B | 0.5 | — | 140 |
| 16-13 | 0.5 | — | 109 |
| 26-3 | 0.5 | — | 119 |
| Vehicle control 2* (containing sodium azide) | — | — | 112 |

*Vehicle controls 1 and 2, respectively, contain sodium azide in concenteration of 0.005 nM and 0.5 nM that are the same concentrations of 16-13 and 26-3 antibodies.

The IGF-I enhanced the proliferation activity compared to the control antibody (FLAG M2, Sigma-Aldrich).

16-13 antibody and 26-3 antibody described in Non-Patent Literature 35 (i.e., agonist antibodies that have an in vitro effect to enhance cellular DNA synthesis and glucose uptake) exhibited no significant cell proliferation activity compared to the vehicle control (containing sodium azide) and lower activity than that of R11-16B.

Example 6: In Vivo Efficacy (Increasing Effect in Muscle Mass in Guinea Pigs)

An in vivo efficacy of an IGF-I receptor agonist antibody was confirmed by comparison with the effect of continuous administration of IGF-I.

A single dose of R11-16B was administered to guinea pigs, and muscle mass was measured after two weeks. The increasing effect in muscle mass is certified by the effect that causes an increase in muscle weight of guinea pigs by 5% or more compared to the control group. A single dose of R11-16B (0.1 and 0.3 mg/kg) was intravenously administered in normal guinea pigs. A positive control was guinea pigs into which human recombinant IGF-I (mecasermin) was subcutaneously implanted using an osmotic pump (Alzet) and continuously administered in an amount of 0.3 and 1 mg/kg/day. Two weeks after administration, the guinea pigs were exsanguinated under anesthesia, and the weight of extensor digitorum longus muscle was measured. The results are shown in FIG. 2.

In the group (R11-16B) into which R11-16B were intravenously administered in an amount of 0.1 and 0.3 mg/kg, the muscle mass increased depending on the dosage and significantly increased compared to the control group (vehicle) into which a vehicle was added alone.

An increase in muscle mass in the single administration group of R11-16B in an amount of 0.3 mg/kg was mostly equivalent to that in the group (IGF-I) into which human recombinant IGF-I was continuously administered in an amount of 1 mg/kg/day. This result indicated that a single administration of R11-16B had the equivalent efficacy to a continuous administration of IGF-I. Since the clinical dose of IGF-I (mecasermin) was administered once or twice daily and, in contrast, in vivo administration of R11-16B once every two weeks had the equivalent effect to a continuous administration of IGF-I, the R11-16B exhibited superior persistence to the IGF-I.

Example 7: In Vivo Hypoglycemic Effect (Hypoglycemic Effect in Guinea Pigs)

A single dose of R11-16B was administered to guinea pigs, and blood glucose levels were measured with time and compared with the hypoglycemic effect in a single administration of IGF-I to verify the existence of in vivo hypoglycemic effect of an IGF-I receptor agonist antibody. The hypoglycemic effect is certified by the effect that lowers the blood glucose level to 50 mg/dL or less or causes hypoglycemic symptoms.

The hypoglycemic effect of IGF-I was examined. Guinea pigs were fasted for 12 hours and a single dose of the human recombinant IGF-I (mecasermin) was subcutaneously administered in an amount of 0.3, 1, 3, and 10 mg/kg. Guinea pigs were fasted until 24 hours after administration.

Blood samples were collected from awake guinea pigs before administration (0 hour) and at 1, 2, 4, 8, and 24 hours after administration, and blood glucose levels were measured with a Glutest sensor (Sanwa Kagaku Kenkyusho). The results are shown in Table 7.
[Table 7]

TABLE 7

Hypoglycemic effect of IGF-I in fasting guinea pigs

| Time | Vehicle control | IGF-I administration group (mg/kg) | | | |
|---|---|---|---|---|---|
| (Hours) | group | 0.3 | 1 | 3 | 10 |
| 0 | 114 | 93 | 108 | 92 | 94 |
| 1 | 116 | 77 | 35 | 30 | 20 |
| 2 | 115 | 31 | 20 | 20 | 20 |
| 4 | 105 | 48 | 20 | 20 | 20 |
| 8 | 99 | 94 | 35 | 24 | — |
| 24 | 95 | 85 | 95 | 101 | — |

The values in the Table indicate the mean blood glucose level (mg/dL).
Less than the lower measurable limit of blood glucose level (less than 20 mg/dL) was indicated as 20.
—: No data were available because all the individuals died.

IGF-I significantly lowered the blood glucose level in an amount of 0.3 mg/kg or more, hypoglycemic symptoms occurred in an amount of 1 mg/kg or more, and death cases were observed in an amount of 3 mg/kg or more.

The effects of R11-16B, R11-16C, R11-16D, R11-16E and R11-16F on blood glucose levels were examined. Guinea pigs were fasted for 12 hours and each humanized antibody was administered in an amount of 10 mg/kg in a single intravenous dose. Guinea pigs were fasted until 24 hours after administration. Blood samples were collected from awake guinea pigs before administration (0 hour) and at 1, 2, 4, 8, and 24 hours after administration, and blood glucose levels were measured with a Glutest sensor (Sanwa Kagaku Kenkyusho). The results are shown in Tables 8 to 10.
[Table 8]

TABLE 8

Effects of R11-16B on blood glucose levels* in fasting guinea pigs

| Time (Hours) | Vehicle control group | R11-16B administration group (10 mg/kg) |
|---|---|---|
| 0 | 90 | 81 |
| 1 | 81 | 82 |
| 2 | 79 | 78 |
| 4 | 81 | 68 |
| 8 | 87 | 74 |
| 24 | 79 | 70 |

*The values in the Table indicate the mean blood glucose levels (mg/dL).

[Table 9]

TABLE 9

Effects of R11-16C and R11-16D on blood glucose levels* in fasting guinea pigs

| Time (Hours) | Vehicle control group | R11-16C administration group (10 mg/kg) | R11-16D administration group (10 mg/kg) |
|---|---|---|---|
| 0 | 91 | 88 | 95 |
| 1 | 90 | 94 | 87 |
| 2 | 92 | 91 | 91 |
| 4 | 84 | 80 | 77 |
| 8 | 80 | 76 | 80 |
| 24 | 79 | 78 | 72 |

*The values in the Table indicate the mean blood glucose levels (mg/dL).

[Table 10]

TABLE 10

Effects of R11-16E and R11-16F on blood glucose levels* in fasting guinea pigs

| Time (Hours) | Vehicle control group | R11-16E administration group (10 mg/kg) | R11-16F administration group (10 mg/kg) |
|---|---|---|---|
| 0 | 103 | 103 | 101 |
| 1 | 92 | 102 | 102 |
| 2 | 91 | 96 | 103 |
| 4 | 91 | 94 | 95 |
| 8 | 94 | 100 | 106 |
| 24 | 92 | 94 | 87 |

*The values in the Table indicate the mean blood glucose levels (mg/dL).

Each humanized antibody had a blood glucose level of 50 mg/dL or more after administration that exhibited no significant difference to the vehicle control group to which the vehicle was administered alone. These results demonstrate that each humanized antibody had no significant hypoglycemic effect and no effect on the blood glucose level, unlike IGF-I, and thereby each humanized antibody exhibited high potential as an agent that can overcome hypoglycemia, which was a side effect in use of IGF-I.

Example 8: Blood Kinetics of IGF-I and R11-16B (Blood Kinetics in Guinea Pigs)

Blood Kinetics of IGF-I

Figure 3:
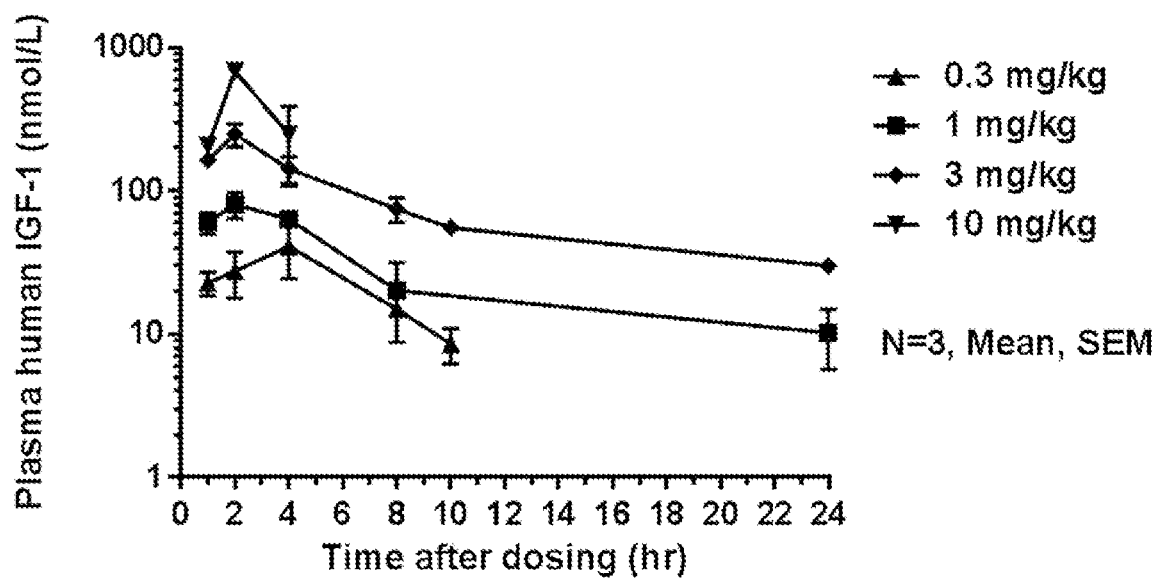
FIG. 3 is a graph indicating the blood kinetics of IGF-I in guinea pigs under fasting conditions after single-dose subcutaneous administration.

Guinea pigs were fasted for 12 hours and human recombinant IGF-I was subcutaneously administered in an amount of 0.3, 1, 3, and 10 mg/kg. Guinea pigs were fasted until 24 hours after administration. Blood samples were collected from awake guinea pigs before administration (0 hour) and at 1, 2, 4, 8, 10 and 24 hours after administration, and the concentration of human IGF-I in plasma was measured by an ELISA (DG100, R&D). The results are shown in FIG. 3.

The IGF-I concentration in plasma increased depending on the dosage, and the IGF-I concentration in plasma decreased to about 50% or less of the maximum peak at 24 hours after administration. The IGF-I concentration in the administration group in an amount of 0.3 mg/kg reached below the lower measurable limit at 24 hours after administration. In the administration group in an amount of 10 mg/kg, plasma could not be collected because the guinea pigs died due to hypoglycemia beyond four hours after administration.

Blood Kinetics of Humanized Antibody

Figure 4:
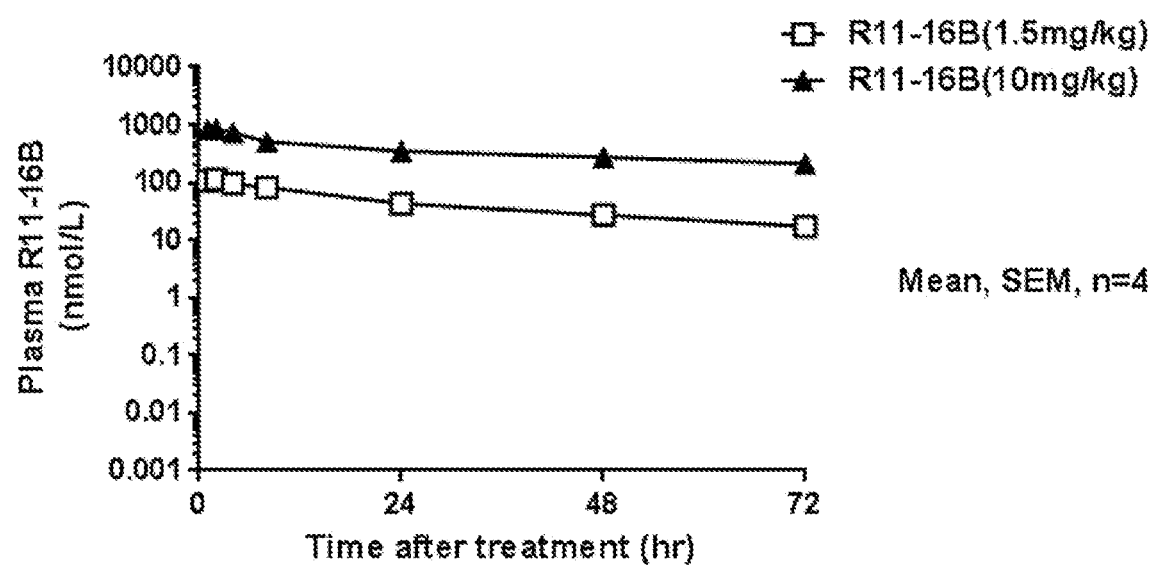
FIG. 4 is a graph indicating the blood kinetics of anti-IGF-I receptor humanized antibody R11-16B in guinea pigs under fasting conditions with time after single-dose intravenous administration.

Guinea pigs were fasted for 12 hours and humanized antibody R11-16B was administered in an amount of 1.5 and 10 mg/kg in a single intravenous dose. Guinea pigs were fasted until 24 hours after administration and then refed after fasting for 24 hours. Blood samples were collected from awake guinea pigs before administration (0 hour) and at 2, 4, 8, 24, 48 and 72 hours after administration, and the concentration of humanized antibody in plasma was measured by the ELISA. The results are shown in FIG. 4.

The concentration of humanized antibody in plasma increased depending on the dosage, and the concentration of humanized antibody in plasma was maintained at about 50% or more even at 48 hours or more after administration compared to that at 24 hours after administration. The blood kinetics of the humanized antibody exhibited superior persistence to that of IGF-I.

INDUSTRIAL APPLICABILITY

The present invention can provide an antibody which specifically binds to an IGF-I receptor of a vertebrate, and thereby increase the muscle mass via the IGF-I receptor, but does not lower the blood glucose level. Therefore, the present invention can be used for the treatment, prevention, or diagnosis of diseases associated with an anti-IGF-I receptor humanized antibody.

The invention claimed is:

1. An anti-IGF-I receptor humanized antibody or antigen-binding fragment thereof or a derivative thereof comprising:
a heavy-chain variable region comprising the amino acid sequence of SEQ ID NO:7; and
a light-chain variable region comprising an amino acid sequence selected from SEQ ID NOs:8, 9, 10, 11, and 12.

2. The anti-IGF-I receptor humanized antibody or an antigen-binding fragment thereof or a derivative thereof according to claim 1, comprising:
as heavy- and light-chain constant regions, the constant regions of a class of human immunogloblin.

3. The anti-IGF-I receptor humanized antibody or an antigen-binding fragment thereof or a derivative thereof according to claim 2, wherein the heavy-chain constant region is the heavy-chain constant region of human IgG class 4.

4. A pharmaceutical composition comprising, as an active ingredient, an anti-IGF-I receptor humanized antibody or an antigen-binding fragment thereof or a derivative thereof according to claim 1.

5. A method for treating disuse muscle atrophy, sarcopenia, cachexia or dwarfism, said method comprising administering, to a subject in need thereof, the composition of claim 4.

6. The method according to claim 5, wherein the dwarfism is Laron-type dwarfism or growth-hormone resistant dwarfism.

* * * * *

SEQUENCE LISTING

```
<160> NUMBER OF SEQ ID NOS: 30

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence, CDR-H1

<400> SEQUENCE: 1

Ser Tyr Trp Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic sequence, CDR-H2

<400> SEQUENCE: 2

Glu Thr Asn Pro Ser Asn Ser Val Thr Asn Tyr Asn Glu Lys Phe Lys
1               5                   10                  15

Ser

<210> SEQ ID NO 3
<211> LENGTH: 8
<212> TYPE: PRT
<213> ORGANISM: Artificial Sequence
<220> FEATURE:
<223> OTHER INFORMATION: Synthetic sequence, CDR-H3

<400> SEQUENCE: 3

Gly Arg Gly Arg Gly Phe Ala Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic sequence, CDR-L1

<400> SEQUENCE: 4

Arg Ala Ser Gln Asn Ile Asn Phe Trp Leu Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic sequence, CDR-L2
```

```
<400> SEQUENCE: 5

Lys Ala Ser Asn Leu His Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic sequence, CDR-L3

<400> SEQUENCE: 6

Leu Gln Gly Gln Ser Tyr Pro Tyr Thr
1               5

<210> SEQ ID NO 7
<211> LENGTH: 117
<212> TYPE: PRT
<213> ORGANISM: Artificial Sequence
<220> FEATURE:
<223> OTHER INFORMATION: Synthetic sequence, R11-16VH

<400> SEQUENCE: 7

Gln Val Gln Leu Val Gln Pro Gly Ala Glu Leu Val Lys Pro Gly Ala
1               5                   10                  15

Ser Val Lys Val Ser Cys Lys Ala Pro Gly Tyr Thr Phe Thr Ser Tyr
                20                  25                  30

Trp Met His Trp Val Arg Gln Ala Pro Gly Gln Gly Leu Glu Trp Ile
            35                  40                  45

Gly Glu Thr Asn Pro Ser Asn Ser Val Thr Asn Tyr Asn Glu Lys Phe
50                  55                  60

Lys Ser Lys Ala Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Ile Gly Arg Gly Arg Gly Phe Ala Tyr Trp Gly Gln Gly Thr Leu
                100                 105                 110

Val Thr Val Ser Ser
            115

<210> SEQ ID NO 8
<211> LENGTH: 107
<212> TYPE: PRT
<213> ORGANISM: Artificial Sequence
<220> FEATURE:
<223> OTHER INFORMATION: Synthetic sequence, R11-16VL-C36Y

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Phe Trp
                20                  25                  30

Leu Ser Trp Tyr Gln Gln Lys Pro Gly Lys Ala Pro Lys Leu Leu Ile
            35                  40                  45

Tyr Lys Ala Ser Asn Leu His Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Gly Gln Ser Tyr Pro Tyr
                85                  90                  95
```

Thr Phe Gly Gln Gly Thr Lys Leu Glu Ile Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: Synthetic sequence, R11-16VL-C36A

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Phe Trp
            20                  25                  30

Leu Ser Trp Ala Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Gly Gln Ser Tyr Pro Tyr
                85                  90                  95

Thr Phe Gly Gln Gly Thr Lys Leu Glu Ile Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: Synthetic sequence, R11-16VL-C36S

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Phe Trp
            20                  25                  30

Leu Ser Trp Ser Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Gly Gln Ser Tyr Pro Tyr
                85                  90                  95

Thr Phe Gly Gln Gly Thr Lys Leu Glu Ile Lys
            100                 105

<210> SEQ ID NO 11
<211> LENGTH: 107
<212> TYPE: PRT
<213> ORGANISM: Artificial Sequence
<220> FEATURE:
<223> OTHER INFORMATION: Synthetic sequence, R11-16VL-C36F

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Phe Trp
            20                  25                  30

Leu Ser Trp Phe Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Gly Gln Ser Tyr Pro Tyr
                85                  90                  95

Thr Phe Gly Gln Gly Thr Lys Leu Glu Ile Lys
            100                 105

<210> SEQ ID NO 12
<211> LENGTH: 107
<212> TYPE: PRT
<213> ORGANISM: Artificial Sequence
<220> FEATURE:
<223> OTHER INFORMATION: Synthetic sequence, R11-16VL-C36

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Phe Trp
            20                  25                  30

Leu Ser Trp Cys Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Gly Gln Ser Tyr Pro Tyr
                85                  90                  95

Thr Phe Gly Gln Gly Thr Lys Leu Glu Ile Lys
            100                 105

<210> SEQ ID NO 13
<211> LENGTH: 70
<212> TYPE: PRT
<213> ORGANISM: Homo sapiens

<400> SEQUENCE: 13

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 14
<211> LENGTH: 1367
<212> TYPE: PRT
<213> ORGANISM: Homo sapiens

<400> SEQUENCE: 14

```
Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
                100                 105                 110

Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
        130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
                180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Thr Cys Gly Lys Arg Ala Cys
        210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
                260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
        290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
        370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415
```

-continued

```
Asn Tyr Ser Phe Tyr Val Leu Asp Asn Gln Asn Leu Gln Gln Leu Trp
                420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
    450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Thr Trp His Arg Tyr
        500                 505                 510

Arg Pro Pro Asp Tyr Arg Asp Leu Ile Ser Phe Thr Val Tyr Tyr Lys
    515                 520                 525

Glu Ala Pro Phe Lys Asn Val Thr Glu Tyr Asp Gly Gln Asp Ala Cys
530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
                595                 600                 605

Ser Val Pro Ser Ile Pro Leu Asp Val Leu Ser Ala Ser Asn Ser Ser
        610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
        675                 680                 685

Thr Glu Val Cys Gly Gly Glu Lys Gly Pro Cys Cys Ala Cys Pro Lys
    690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
        755                 760                 765

Glu Glu Leu Glu Thr Glu Tyr Pro Phe Phe Glu Ser Arg Val Asp Asn
    770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
```

```
                835             840             845
Phe Leu Lys Trp Pro Glu Pro Glu Asn Pro Asn Gly Leu Ile Leu Met
    850             855             860
Tyr Glu Ile Lys Tyr Gly Ser Gln Val Glu Asp Gln Arg Glu Cys Val
865             870             875             880
Ser Arg Gln Glu Tyr Arg Lys Tyr Gly Ala Lys Leu Asn Arg Leu
                885             890             895
Asn Pro Gly Asn Tyr Thr Ala Arg Ile Gln Ala Thr Ser Leu Ser Gly
                900             905             910
Asn Gly Ser Trp Thr Asp Pro Val Phe Phe Tyr Val Gln Ala Lys Thr
                915             920             925
Gly Tyr Glu Asn Phe Ile His Leu Ile Ile Ala Leu Pro Val Ala Val
                930             935             940
Leu Leu Ile Val Gly Gly Leu Val Ile Met Leu Tyr Val Phe His Arg
945             950             955             960
Lys Arg Asn Asn Ser Arg Leu Gly Asn Gly Val Leu Tyr Ala Ser Val
                965             970             975
Asn Pro Glu Tyr Phe Ser Ala Ala Asp Val Tyr Val Pro Asp Glu Trp
                980             985             990
Glu Val Ala Arg Glu Lys Ile Thr  Met Ser Arg Glu Leu  Gly Gln Gly
                995             1000             1005
Ser Phe Gly Met Val Tyr Glu  Gly Val Ala Lys Gly  Val Val Lys
    1010             1015             1020
Asp Glu  Pro Glu Thr Arg Val  Ala Ile Lys Thr Val  Asn Glu Ala
    1025             1030             1035
Ala Ser  Met Arg Glu Arg Ile  Glu Phe Leu Asn Glu  Ala Ser Val
    1040             1045             1050
Met Lys  Glu Phe Asn Cys His  His Val Val Arg Leu  Leu Gly Val
    1055             1060             1065
Val Ser  Gln Gly Gln Pro Thr  Leu Val Ile Met Glu  Leu Met Thr
    1070             1075             1080
Arg Gly  Asp Leu Lys Ser Tyr  Leu Arg Ser Leu Arg  Pro Glu Met
    1085             1090             1095
Glu Asn  Asn Pro Val Leu Ala  Pro Pro Ser Leu Ser  Lys Met Ile
    1100             1105             1110
Gln Met  Ala Gly Glu Ile Ala  Asp Gly Met Ala Tyr  Leu Asn Ala
    1115             1120             1125
Asn Lys  Phe Val His Arg Asp  Leu Ala Ala Arg Asn  Cys Met Val
    1130             1135             1140
Ala Glu  Asp Phe Thr Val Lys  Ile Gly Asp Phe Gly  Met Thr Arg
    1145             1150             1155
Asp Ile  Tyr Glu Thr Asp Tyr  Tyr Arg Lys Gly Gly  Lys Gly Leu
    1160             1165             1170
Leu Pro  Val Arg Trp Met Ser  Pro Glu Ser Leu Lys  Asp Gly Val
    1175             1180             1185
Phe Thr  Thr Tyr Ser Asp Val  Trp Ser Phe Gly Val  Val Leu Trp
    1190             1195             1200
Glu Ile  Ala Thr Leu Ala Glu  Gln Pro Tyr Gln Gly  Leu Ser Asn
    1205             1210             1215
Glu Gln  Val Leu Arg Phe Val  Met Glu Gly Gly Leu  Leu Asp Lys
    1220             1225             1230
Pro Asp  Asn Cys Pro Asp Met  Leu Phe Glu Leu Met  Arg Met Cys
    1235             1240             1245
```

| | | | | | | | | | | |
|---|---|---|---|---|---|---|---|---|---|---|
| Trp | Gln | Tyr | Asn | Pro | Lys | Met | Arg | Pro | Ser | Phe | Leu | Glu | Ile | Ile |
| | 1250 | | | | 1255 | | | | 1260 | |

Trp Gln Tyr Asn Pro Lys Met Arg Pro Ser Phe Leu Glu Ile Ile
    1250                1255              1260

Ser Ser Ile Lys Glu Glu Met Glu Pro Gly Phe Arg Glu Val Ser
    1265                1270              1275

Phe Tyr Tyr Ser Glu Glu Asn Lys Leu Pro Glu Pro Glu Glu Leu
    1280                1285              1290

Asp Leu Glu Pro Glu Asn Met Glu Ser Val Pro Leu Asp Pro Ser
    1295                1300              1305

Ala Ser Ser Ser Leu Pro Leu Pro Asp Arg His Ser Gly His
    1310                1315              1320

Lys Ala Glu Asn Gly Pro Gly Pro Gly Val Leu Val Leu Arg Ala
    1325                1330              1335

Ser Phe Asp Glu Arg Gln Pro Tyr Ala His Met Asn Gly Gly Arg
    1340                1345              1350

Lys Asn Glu Arg Ala Leu Pro Leu Pro Gln Ser Ser Thr Cys
    1355                1360              1365

<210> SEQ ID NO 15
<211> LENGTH: 4128
<212> TYPE: DNA
<213> ORGANISM: Homo sapiens

<400> SEQUENCE: 15

```
atgaagtctg gctccggagg agggtccccg acctcgctgt gggggctcct gtttctctcc      60
gccgcgctct cgctctggcc gacgagtgga gaaatctgcg gccaggcat cgacatccgc     120 aacgactatc agcagctgaa gcgcctggag aactgcacgg tgatcgaggg ctacctccac     180
atcctgctca tctccaaggc cgaggactac cgcagctacc gcttccccaa gctcacggtc     240
attaccgagt acttgctgct gttccgagtg gctggcctcg agagcctcgg agacctcttc     300
cccaacctca cggtcatccg cggctggaaa ctcttctaca actacgccct ggtcatcttc     360
gagatgacca atctcaagga tattgggctt acaacctga ggaacattac tcgggggggcc     420 atcaggattg agaaaaatgc tgacctctgt tacctctcca ctgtggactg gtccctgatc     480
ctggatgcgg tgtccaataa ctacattgtg gggaataagc ccccaaagga atgtgggggac     540 ctgtgtccag ggaccatgga ggagaagccg atgtgtgaga agaccaccat caacaatgag     600
tacaactacc gctgctggac cacaaaccgc tgccagaaaa tgtgcccaag cacgtgtggg     660
aagcgggcgt gcaccgagaa caatgagtgc tgccacccg agtgcctggg cagctgcagc     720
gcgcctgaca cgacacggc ctgtgtagct tgccgccact actactatgc cggtgtctgt     780
gtgcctgcct gcccgcccaa cacctacagg tttgagggct ggcgctgtgt ggaccgtgac     840
ttctgcgcca catcctcag cgccgagagc agcgactccg aggggtttgt gatccacgac     900
ggcgagtgca tgcaggagtg cccctcgggc ttcatccgca acggcagcca gagcatgtac     960 tgcatcccctt gtgaaggtcc ttgcccgaag gtctgtgagg aagaaaagaa aacaaagacc    1020
attgattctg ttacttctgc tcagatgctc caaggatgca ccatcttcaa gggcaatttg    1080
ctcattaaca tccgacgggg gaataacatt gcttcagagc tggagaactt catggggctc    1140
atcgaggtgg tgacgggcta cgtgaagatc cgccattctc atgccttggt ctccttgtcc    1200
ttcctaaaaa accttcgcct catcctagga gaggagcagc tagaaggggaa ttactccttc    1260 tacgtcctcg acaaccagaa cttgcagcaa ctgtgggact gggaccaccg caacctgacc    1320
atcaaagcag ggaaaatgta ctttgctttc aatcccaaat tatgtgtttc cgaaatttac    1380
```

-continued

```
cgcatggagg aagtgacggg gactaaaggg cgccaaagca aaggggacat aaacaccagg    1440
aacaacgggg agagagcctc ctgtgaaagt gacgtcctgc atttcacctc caccaccacg    1500
tcgaagaatc gcatcatcat aacctggcac cggtaccggc cccctgacta cagggatctc    1560
atcagcttca ccgtttacta caaggaagca ccctttaaga atgtcacaga gtatgatggg    1620
caggatgcct gcggctccaa cagctggaac atggtggacg tggacctccc gcccaacaag    1680
gacgtggagc ccggcatctt actacatggg ctgaagccct ggactcagta cgccgtttac    1740
gtcaaggctg tgaccctcac catggtggag aacgaccata tccgtggggc aagagtgag    1800 atcttgtaca ttcgcaccaa tgcttcagtt ccttccattc ccttggacgt tctttcagca    1860
tcgaactcct cttctcagtt aatcgtgaag tggaaccctc cctctctgcc caacggcaac    1920
ctgagttact acattgtgcg ctggcagcgg cagcctcagg acggctacct ttaccggcac    1980
aattactgct ccaaagacaa aatccccatc aggaagtatg ccgacggcac catcgacatt    2040
gaggaggtca cagagaaccc caagactgag gtgtgtggtg gggagaaagg gccttgctgc    2100
gcctgcccca aaactgaagc cgagaagcag gccgagaagg aggaggctga ataccgcaaa    2160
gtctttgaga atttcctgca caactccatc ttcgtgccca gacctgaaag gaagcggaga    2220
gatgtcatgc aagtggccaa caccaccatg tccagccgaa gcaggaacac cacggccgca    2280
gacacctaca acatcaccga cccggaagag ctggagacag agtacccttt ctttgagagc    2340
agagtggata caaggagag aactgtcatt tctaaccttc ggcctttcac attgtaccgc    2400
atcgatatcc acagctgcaa ccacgaggct gagaagctgg gctgcagcgc ctccaacttc    2460
gtctttgcaa ggactatgcc cgcagaagga gcagatgaca ttcctgggcc agtgacctgg    2520
gagccaaggc ctgaaaactc catcttttta aagtggccgg aacctgagaa tcccaatgga    2580
ttgattctaa tgtatgaaat aaaatacgga tcacaagttg aggatcagcg agaatgtgtg    2640
tccagacagg aatacaggaa gtatggaggg gccaagctaa accggctaaa cccggggaac    2700
tacacagccc ggattcaggc cacatctctc tctgggaatg ggtcgtggac agatcctgtg    2760
ttcttctatg tccaggccaa aacaggatat gaaaacttca tccatctgat catcgctctg    2820
cccgtcgctg tcctgttgat cgtgggaggg ttggtgatta tgctgtacgt cttccataga    2880
aagagaaata acagcaggct ggggaatgga gtgctgtatg cctctgtgaa cccggagtac    2940
ttcagcgctg ctgatgtgta cgttcctgat gagtgggagg tggctcggga aagatcacc    3000 atgagccggg aacttgggca ggggtcgttt gggatggtct atgaaggagt tgccaagggt    3060
gtggtgaaag atgaacctga aaccagagtg gccattaaaa cagtgaacga ggccgcaagc    3120
atgcgtgaaa ggattgagtt tctcaacgaa gcttctgtga tgaaggagtt caattgtcac    3180
catgtggtgc gattgctggg tgtggtgtcc caaggccagc caacactggt catcatggaa    3240
ctgatgacac ggggcgatct caaaagttat ctccggtctc tgaggccaga aatggagaat    3300
aatccagtcc tagcacctcc aagcctgagc aagatgattc agatggccgg agagattgca    3360
gacggcatgg catacctcaa cgccaataag ttcgtccaca gagaccttgc tgcccggaat    3420
tgcatggtag ccgaagattt cacagtcaaa atcggagatt ttggtatgac gcgagatatc    3480
tatgagacag actattaccg gaaggagggg aaagggctgc tgcccgtgcg ctggatgtct    3540
cctgagtccc tcaaggatgg agtcttcacc acttactcgg acgtctggtc cttcggggtc    3600
gtcctctggg agatcgccac actggccgag cagccctacc agggcttgtc caacgagcaa    3660
gtccttcgct tcgtcatgga gggcggcctt ctggacaagc cagacaactg tcctgacatg    3720
ctgtttgaac tgatgcgcat gtgctggcag tataacccca gatgaggcc ttccttcctg    3780
```

-continued

```
gagatcatca gcagcatcaa agaggagatg gagcctggct tccgggaggt ctccttctac    3840
tacagcgagg agaacaagct gcccgagccg gaggagctgg acctggagcc agagaacatg    3900
gagagcgtcc ccctggaccc ctcggcctcc tcgtcctccc tgccactgcc cgacagacac    3960
tcaggacaca aggccgagaa cggccccggc cctggggtgc tggtcctccg cgccagcttc    4020
gacgagagac agccttacgc ccacatgaac ggggccgca agaacgagcg ggccttgccg      4080
ctgccccagt cttcgacctg cgattataag gatgacgatg acaagtag                  4128
```

<210> SEQ ID NO 16
<211> LENGTH: 1367
<212> TYPE: PRT
<213> ORGANISM: Cavia porcellus

<400> SEQUENCE: 16

```
Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Ser Pro Lys
                165                 170                 175

Glu Cys Gly Asp Leu Cys Pro Gly Thr Met Glu Glu Lys Pro Leu Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Ala Cys Gly Lys Arg Ala Cys
    210                 215                 220

Thr Glu Tyr Gln Glu Cys Cys His Pro Glu Cys Leu Gly Ser Cys His
225                 230                 235                 240

Ala Pro Asp Asp Thr Ala Cys Val Ala Cys Arg His Phe Tyr Tyr
                245                 250                 255

Ala Gly Ile Cys Val Pro Ala Cys Pro Pro Gly Thr Tyr Arg Phe Glu
            260                 265                 270

Gly Trp Arg Cys Val His Arg Asp Phe Cys Ala Asn Ile Pro Asn Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
```

```
                305                 310                 315                 320
Cys Ile Pro Cys Glu Gly Pro Cys Pro Lys Val Cys Glu Glu Glu Lys
                    325                 330                 335

Lys Thr Lys Thr Ile Asp Ser Val Thr Ser Ala Gln Met Leu Gln Gly
                    340                 345             350

Cys Thr Ile Phe Lys Gly Asn Leu Leu Ile Asn Ile Arg Arg Gly Asn
                    355                 360                 365

Asn Ile Ala Ser Glu Leu Glu Asn Phe Met Gly Leu Ile Glu Val Val
            370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                    405                 410                 415

Asn Tyr Ser Phe Tyr Val Leu Asp Asn Gln Asn Leu Gln Gln Leu Trp
                420                 425                 430

Asp Trp Asp His Arg Asn Leu Thr Ile Lys Ser Gly Lys Met Tyr Phe
                435                 440                 445

Ala Phe Asn Pro Lys Leu Cys Val Ser Glu Ile Tyr Arg Met Glu Glu
            450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu Arg Phe Thr
                    485                 490                 495

Ser Thr Thr Thr Ser Lys Asn Arg Ile Ile Ile Thr Trp His Arg Tyr
                500                 505                 510

Arg Pro Pro Asp Tyr Arg Asp Leu Ile Ser Phe Thr Val Tyr Tyr Lys
                515                 520                 525

Glu Ala Pro Phe Lys Asn Val Thr Glu Tyr Asp Gly Gln Asp Ala Cys
            530                 535                 540

Gly Ser Asn Ser Trp Asn Met Val Asp Val Asp Leu Pro Pro Asn Lys
545                 550                 555                 560

Asp Ala Glu Pro Gly Ile Leu Leu His Gly Leu Lys Pro Trp Thr Gln
                    565                 570                 575

Tyr Ala Val Tyr Val Lys Ala Val Thr Leu Thr Met Val Glu Asn Asp
                580                 585                 590

His Ile Arg Gly Ala Lys Ser Glu Ile Leu Tyr Ile Arg Thr Asn Ala
                595                 600                 605

Ser Val Pro Ser Ile Pro Leu Asp Val Leu Ser Ala Ser Asn Ser Ser
            610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Ser Tyr
                    645                 650                 655

Leu Tyr Arg His Asn Tyr Cys Ser Lys Asp Lys Ile Pro Ile Arg Lys
                660                 665                 670

Tyr Ala Asp Gly Thr Ile Asp Val Glu Glu Val Thr Glu Asn Pro Lys
            675                 680                 685

Thr Glu Val Cys Gly Gly Glu Lys Gly Pro Cys Cys Ala Cys Pro Lys
690                 695                 700

Thr Glu Ala Glu Lys Gln Ala Glu Lys Glu Glu Ala Glu Tyr Arg Lys
                    705                 710                 715                 720

Val Phe Glu Asn Phe Leu His Asn Ser Ile Phe Val Pro Arg Pro Glu
                    725                 730                 735
```

```
Arg Arg Arg Arg Asp Val Ala Gln Met Ala Asn Thr Thr Met Ser Ser
            740                 745                 750

Arg Ser Arg Asn Thr Thr Val Ala Asp Thr Tyr Asn Ala Thr Asp Pro
            755                 760                 765

Glu Glu Leu Glu Thr Gly Tyr Pro Phe Phe Gly Ser Arg Val Asp Asn
        770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Ala Arg Pro Glu Asn Ser Ile
        835                 840                 845

Phe Leu Lys Trp Pro Glu Pro Glu Asn Pro Asn Gly Leu Ile Leu Met
    850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Ser Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Pro Ala Lys Thr
        915                 920                 925

Thr Tyr Glu Asn Phe Ile His Leu Ile Ile Ala Leu Pro Val Ala Ile
    930                 935                 940

Leu Leu Ile Val Ala Gly Leu Ala Ile Met Leu Tyr Val Phe His Arg
945                 950                 955                 960

Lys Arg Asn Ser Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
            995                 1000                1005

Ser Phe Gly Met Val Tyr Glu Gly Val Ala Lys Gly Val Val Lys
    1010                1015                1020

Asp Glu Pro Glu Thr Arg Val Ala Ile Lys Thr Val Asn Glu Ala
    1025                1030                1035

Ala Ser Met Arg Glu Arg Ile Glu Phe Leu Asn Glu Ala Ser Val
    1040                1045                1050

Met Lys Glu Phe Asn Cys His His Val Val Arg Leu Leu Gly Val
    1055                1060                1065

Val Ser Gln Gly Gln Pro Thr Leu Val Ile Met Glu Leu Met Thr
    1070                1075                1080

Arg Gly Asp Leu Lys Ser Tyr Leu Arg Ser Leu Arg Pro Glu Val
    1085                1090                1095

Glu Asn Ser Pro Ile Leu Ala Pro Pro Ser Leu Ser Lys Met Ile
    1100                1105                1110

Gln Met Ala Gly Glu Ile Ala Asp Gly Met Ala Tyr Leu Asn Ala
    1115                1120                1125

Asn Lys Phe Val His Arg Asp Leu Ala Ala Arg Asn Cys Met Val
    1130                1135                1140
```

| | | | | | | | | | | | |
|---|---|---|---|---|---|---|---|---|---|---|---|
| Ala | Glu | Asp | Phe | Thr | Val | Lys | Ile | Gly | Asp | Phe | Gly |
| | 1145 | | | | 1150 | | | | 1155 | | |
| Met | Thr | Arg | | | | | | | | | |

Asp Ile Tyr Glu Thr Asp Tyr Tyr Arg Lys Gly Gly Lys Gly Leu
    1160                1165                1170

Leu Pro Val Arg Trp Met Ser Pro Glu Ser Leu Lys Asp Gly Val
    1175                1180                1185

Phe Thr Thr His Ser Asp Val Trp Ser Phe Gly Val Val Leu Trp
    1190                1195                1200

Glu Ile Ala Thr Leu Ala Glu Gln Pro Tyr Gln Gly Leu Ser Asn
    1205                1210                1215

Glu Gln Val Leu Arg Phe Val Met Glu Gly Gly Leu Leu Asp Lys
    1220                1225                1230

Pro Asp Asn Cys Pro Asp Met Leu Phe Glu Leu Met Arg Met Cys
    1235                1240                1245

Trp Gln Tyr Asn Pro Lys Met Arg Pro Ser Phe Leu Glu Ile Ile
    1250                1255                1260

Ser Ser Val Lys Asp Glu Leu Glu Ala Gly Phe Arg Glu Val Ser
    1265                1270                1275

Phe Tyr Tyr Ser Glu Glu Asn Lys Pro Pro Glu Pro Glu Glu Leu
    1280                1285                1290

Asp Leu Glu Pro Glu Asn Met Glu Ser Val Pro Leu Asp Pro Ser
    1295                1300                1305

Ala Ser Ser Ser Ser Leu Pro Pro Pro Asp Arg His Ser Gly His
    1310                1315                1320

Lys Gly Glu Asn Gly Pro Gly Pro Gly Val Leu Val Leu Arg Ala
    1325                1330                1335

Ser Phe Asp Glu Arg Gln Pro Tyr Ala His Met Asn Gly Gly Arg
    1340                1345                1350

Thr Asn Glu Arg Ala Leu Pro Leu Pro Gln Ser Ser Thr Cys
    1355                1360                1365

<210> SEQ ID NO 17
<211> LENGTH: 4128
<212> TYPE: DNA
<213> ORGANISM: Cavia porcellus

<400> SEQUENCE: 17

```
atgaagtctg gctccggagg agggtccccg acctcgctgt gggggctcct gtttctctct      60
gctgcgctct cgctctggcc gacgagtgga gaaatctgtg gccgggcat cgacatccgc     120
aatgactatc agcagctaaa acgcctggag aactgcacgg tgatcgaggg ctacctccac     180
atcctgctca tctccaaggc cgaggactac cgcagctacc gcttccccaa gctcaccgtc     240
atcaccgagt acttgctgct gttccgggtc gctggcctcg agagcctcgg agacctcttc     300
ccgaacctca ccgtcatccg cggctggaaa ctcttctata actacgccct ggtcatcttc     360
gagatgacca acctgaagga tattgggctt tacaacctga ggaacattac tcggggggcc     420
atcaggattg agaagaatgc tgacctgtgc tacctctcca cagtggactg gtcgctgatc     480
ctggatgcgg tgtccaataa ctacattgtg gggaacaagt ccccaaagga atgtggagac     540
ctgtgtccag ggaccatgga ggagaaacca ttgtgcgaga agaccaccat caacaatgag     600
tacaactacc gctgctggac cacaaatcgc tgccagaaaa tgtgcccaag tgcctgcggg     660
aagcgtgcgt gcaccgagta ccaggagtgc tgccatcctg agtgcctggg cagctgccat     720
gcacccgacg acgacacggc ctgtgtggcc tgcagacact tctactatgc tggcatctgc     780
```

```
gtgcccgcct gtccacccgg cacctaccgc ttcgagggct ggcgctgtgt gcaccgagac    840
ttctgcgcca acatcccaa tgctgagagc agtgactccg agggcttcgt catccatgac     900
ggggagtgca tgcaggagtg tccctcgggc ttcatccgca acggcagcca gagcatgtac    960
tgcatccctt gtgaaggtcc ttgccccaag gtctgcgagg aagaaaagaa gacgaaaacc   1020
attgactctg tgacttctgc tcagatgctc caagggtgca ccatcttcaa gggcaacctg   1080
ctcattaata tccgacgggg caataacatt gcgtcggaac tggagaactt catgggctc    1140 attgaggtgg tgactggcta cgtgaagatc cgccattccc atgccttggt ctccttgtcc   1200
ttcctgaaaa accttcgcct gatcctgggg gaggagcagc tggaagggaa ctactccttc   1260
tacgtcctgg acaaccagaa cctgcagcag ctgtgggatt gggaccaccg caacctcacc   1320
atcaaatctg ggaagatgta ctttgctttc aatcccaaac tgtgtgtctc tgaaatttac   1380
cgcatggaag aagtgacggg gacgaaaggg cgccagagca aggggacat aaacaccagg    1440 aacaacgggg aacagccctc ctgtgaaagt gacgtattgc gtttcacctc caccaccaca   1500
tcgaagaacc gcattatcat cacctggcac cggtaccggc ccccagacta cagggatctc   1560
atcagcttca ctgtttacta caaggaggca ccgtttaaaa atgtcaccga gtatgatggg   1620
caggatgctt gtggctccaa cagttggaac atggtggacg tggacctgcc tcctaacaag   1680
gacgcggagc ctggcatcct actgcatggg ctgaagccct ggacacagta cgcggtctat   1740
gtcaaggccg tgaccctcac catggtagag aacgaccaca tccgtggggc caagagtgaa   1800
atcttgtaca ttcgcaccaa tgcttcagtt ccttccattc ccctggatgt cctttcggca   1860
tccaactcct cttctcagct catcgtcaag tggaacccc catctctgcc aacggaaac    1920 ctgagttatt atatcgtgcg gtggcagcgg cagcctcagg acagctacct ataccggcac   1980
aattactgct ccaaagacaa aatccccatc agaaagtatg cggatggcac catcgatgtc   2040
gaagaggtca ccgagaaccc caagactgaa gtatgtggtg gcgagaaagg gccttgctgc   2100
gcttgcccca aaaccgaagc cgagaagcag gccgagaagg aggaggccga gtaccggaaa   2160
gtgtttgaga atttcctgca caactccatc ttcgtgccga ggcctgaaag gaggcggcga   2220
gatgttgcgc agatgccaa caccaccatg tccagccgca gcaggaacac cacggtggct   2280
gatacctaca tgccacaga tccagaggag ctagagaccg aatacccttt ctttgagagc   2340
agagtggata caaggaaag aactgtaatt caaaacctcc ggccttttac cttgtaccgc   2400
attgacatcc acagctgtaa ccatgaggct gagaagctgg gctgcagcgc ttctaacttt   2460 gttttttgcaa gaaccatgcc cgcagaagga gcagatgaca ttcctggccc ggtgacgtgg   2520
gaagcaaggc ctgaaaactc catcttttta aagtggccag agcctgagaa tcctaatgga   2580
ttgattctaa tgtacgaaat aaaatacgga tcacaagttg aggatcagcg agaatgtgtg   2640
tccagacagg aatacaggaa atacggaggg gccaagctta gccggctaaa cccagggaac   2700
tatacagccc ggattcaagc tacctcgctc tctgggaatg ggtcgtggac agatcctgtg   2760 ttttttctatg tcccagccaa acaacgtat gaaaacttca tccatctgat catcgctctg   2820
ccagtcgcca tcctgttgat tgtggcaggc ttggcgataa tgctgtacgt cttccatagg   2880
aagagaaaca gcagcaggct ggggaatgga gtgttgtacg cctctgtgaa cccggagtac   2940
ttcagtgctg cggatgtgta cgttcctgat gagtgggagg tagcgcgaga aagatcacc    3000 atgagccggg agctggggca aggtccctt gggatggtct acgaaggagt ggctaaaggt   3060
gtggtgaaaa acgagcctga tacccgggta gccatcaaga cagtgaacga ggccgcaagc   3120
atgcgtgaaa ggatcgagtt tctcaatgag gcctctgtga tgaaggagtt caactgtcat   3180
```

-continued

```
catgtggtgc gactgctagg cgtggtgtcc cagggccagc ccacactggt catcatggag    3240
ctgatgacgc gggggggatct caagagctat ctcaggtctt tgaggccgga agtagagaat    3300
agccccatcc tggcacctcc aagcctcagc aagatgatcc agatggccgg agagattgca    3360
gatggcatgg catacctcaa cgccaacaag tttgtccaca gagaccttgc tgcccgcaat    3420
tgcatggtag ctgaagattt cacagtcaaa attggagatt tgggatgac gcgagatatt    3480
tacgagacag actactaccg gaaaggaggg aaagggctgc tgcctgtgcg ctggatgtct    3540
cctgagtccc tcaaggatgg agtcttcacc actcattcgg acgtctggtc cttcggggtc    3600
gtcctctggg agatcgccac gctggctgag cagccatacc agggcttgtc caacgagcaa    3660
gtccttcgct tcgtcatgga gggtggcctc ctggacaaac ccgacaactg cccagacatg    3720
ctgtttgagc tgatgcgcat gtgctggcag tacaacccca agatgaggcc ttccttcctg    3780
gagatcatca gcagcgtcaa agacgagctg gaggccggct tccgggaggt ctccttctac    3840
tacagcgagg agaacaagcc gcccgagccg gaggagctgg acctggagcc cgagaacatg    3900
gagagcgtcc cgctggaccc atcagcctcc tcgtcctccc tgccgccgcc cgacagacac    3960
tcaggacaca agggcgagaa cggcccgggc cccggcgtgc tggtgctccg cgccagcttc    4020
gacgagagac agccttacgc gcacatgaac ggaggccgca cgaacgagag ggccttgccg    4080
ctgccccagt cgtcaacctg cgattataag gatgacgatg acaagtga              4128
```

<210> SEQ ID NO 18
<211> LENGTH: 1367
<212> TYPE: PRT
<213> ORGANISM: Macaca fascicularis

<400> SEQUENCE: 18

```
Met Lys Ser Gly Ser Gly Glu Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205
```

-continued

```
Asn Arg Cys Gln Lys Met Cys Pro Ser Ala Cys Gly Lys Arg Ala Cys
210                 215                 220
Thr Glu Asn Asn Glu Cys Cys His Pro Glu Cys Leu Gly Ser Cys Ser
225                 230                 235                 240
Ala Pro Asp Asn Asp Thr Ala Cys Val Ala Cys Arg His Tyr Tyr Tyr
                245                 250                 255
Ala Gly Val Cys Val Pro Ala Cys Pro Pro Asn Thr Tyr Arg Phe Glu
            260                 265                 270
Gly Trp Arg Cys Val Asp Arg Asp Phe Cys Ala Asn Ile Leu Ser Ala
        275                 280                 285
Glu Ser Ser Asp Ser Glu Gly Phe Val Ile His Asp Gly Glu Cys Met
290                 295                 300
Gln Glu Cys Pro Ser Gly Phe Ile Arg Asn Gly Ser Gln Ser Met Tyr
305                 310                 315                 320
Cys Ile Pro Cys Glu Gly Pro Cys Pro Lys Val Cys Glu Glu Lys
                325                 330                 335
Lys Thr Lys Thr Ile Asp Ser Val Thr Ser Ala Gln Met Leu Gln Gly
                340                 345                 350
Cys Thr Ile Phe Lys Gly Asn Leu Leu Ile Asn Ile Arg Arg Gly Asn
            355                 360                 365
Asn Ile Ala Ser Glu Leu Glu Asn Phe Met Gly Leu Ile Glu Val Val
370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Glu Gln Leu Glu Gly
                405                 410                 415
Asn Tyr Ser Phe Tyr Val Leu Asp Asn Gln Asn Leu Gln Gln Leu Trp
            420                 425                 430
Asp Trp Asp His Arg Asn Leu Thr Ile Lys Ala Gly Lys Met Tyr Phe
        435                 440                 445
Ala Phe Asn Pro Lys Leu Cys Val Ser Glu Ile Tyr Arg Met Glu Glu
450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
                485                 490                 495
Ser Thr Thr Thr Trp Lys Asn Arg Ile Ile Ile Thr Trp His Arg Tyr
            500                 505                 510
Arg Pro Pro Asp Tyr Arg Asp Leu Ile Ser Phe Thr Val Tyr Tyr Lys
        515                 520                 525
Glu Ala Pro Phe Lys Asn Val Thr Glu Tyr Asp Gly Gln Asp Ala Cys
530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
                565                 570                 575
Tyr Ala Val Tyr Val Lys Ala Val Thr Leu Thr Met Val Glu Asn Asp
            580                 585                 590
His Ile Arg Gly Ala Lys Ser Glu Ile Leu Tyr Ile Arg Thr Asn Ala
        595                 600                 605
Ser Val Pro Ser Ile Pro Leu Asp Val Leu Ser Ala Ser Asn Ser Ser
610                 615                 620
```

```
Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
            645                 650                 655

Leu Tyr Arg His Asn Tyr Cys Ser Lys Asp Lys Ile Pro Ile Arg Lys
        660                 665                 670

Tyr Ala Asp Gly Thr Ile Asp Ile Glu Glu Val Thr Glu Asn Pro Lys
    675                 680                 685

Thr Glu Val Cys Gly Gly Glu Lys Gly Pro Cys Cys Ala Cys Pro Lys
690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Val Ala Asp Thr Tyr Asn Ile Thr Asp Leu
        755                 760                 765

Glu Glu Leu Glu Thr Glu Tyr Pro Phe Phe Glu Ser Arg Val Asp Asn
770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn Phe Ile His Leu Ile Ile Ala Leu Pro Val Ala Val
930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
        995                 1000                1005

Ser Phe Gly Met Val Tyr Glu Gly Val Ala Lys Gly Val Val Lys
    1010                1015                1020

Asp Glu Pro Glu Thr Arg Val Ala Ile Lys Thr Val Asn Glu Ala
    1025                1030                1035

Ala Ser Met Arg Glu Arg Ile Glu Phe Leu Asn Glu Ala Ser Val
```

|   |   |   |   |   |   |   |   |   |   |
|---|---|---|---|---|---|---|---|---|---|
|   |   |   | 1040 |   |   | 1045 |   |   | 1050 |
| Met | Lys | Glu | Phe | Asn | Cys | His | His | Val | Val | Arg | Leu | Leu | Gly | Val |
|   |   | 1055 |   |   | 1060 |   |   | 1065 |   |

Met Lys Glu Phe Asn Cys His His Val Val Arg Leu Leu Gly Val
     1055     1060     1065

Val Ser Gln Gly Gln Pro Thr Leu Val Ile Met Glu Leu Met Thr
   1070     1075     1080

Arg Gly Asp Leu Lys Ser Tyr Leu Arg Ser Leu Arg Pro Glu Met
   1085     1090     1095

Glu Asn Asn Pro Val Leu Ala Pro Pro Ser Leu Ser Lys Met Ile
   1100     1105     1110

Gln Met Ala Gly Glu Ile Ala Asp Gly Met Ala Tyr Leu Asn Ala
   1115     1120     1125

Asn Lys Phe Val His Arg Asp Leu Ala Ala Arg Asn Cys Met Val
   1130     1135     1140

Ala Glu Asp Phe Thr Val Lys Ile Gly Asp Phe Gly Met Thr Arg
   1145     1150     1155

Asp Ile Tyr Glu Thr Asp Tyr Tyr Arg Lys Gly Gly Lys Gly Leu
   1160     1165     1170

Leu Pro Val Arg Trp Met Ser Pro Glu Ser Leu Lys Asp Gly Val
   1175     1180     1185

Phe Thr Thr Tyr Ser Asp Val Trp Ser Phe Gly Val Val Leu Trp
   1190     1195     1200

Glu Ile Ala Thr Leu Ala Glu Gln Pro Tyr Gln Gly Leu Ser Asn
   1205     1210     1215

Glu Gln Val Leu Arg Phe Val Met Glu Gly Gly Leu Leu Asp Lys
   1220     1225     1230

Pro Asp Asn Cys Pro Asp Met Leu Phe Glu Leu Met Arg Met Cys
   1235     1240     1245

Trp Gln Tyr Asn Pro Lys Met Arg Pro Ser Phe Leu Glu Ile Ile
   1250     1255     1260

Ser Ser Ile Lys Asp Glu Met Glu Pro Gly Phe Arg Glu Val Ser
   1265     1270     1275

Phe Tyr Tyr Ser Glu Glu Asn Lys Leu Pro Glu Pro Glu Glu Leu
   1280     1285     1290

Asp Leu Glu Pro Glu Asn Met Glu Ser Val Pro Leu Asp Pro Ser
   1295     1300     1305

Ala Ser Ser Ser Ser Leu Pro Leu Pro Asp Arg His Ser Gly His
   1310     1315     1320

Lys Ala Glu Asn Gly Pro Gly Pro Gly Val Leu Val Leu Arg Ala
   1325     1330     1335

Ser Phe Asp Glu Arg Gln Pro Tyr Ala His Met Asn Gly Gly Arg
   1340     1345     1350

Lys Asn Glu Arg Ala Leu Pro Leu Pro Gln Ser Ser Thr Cys
   1355     1360     1365

<210> SEQ ID NO 19
<211> LENGTH: 4128
<212> TYPE: DNA
<213> ORGANISM: Macaca fascicularis

<400> SEQUENCE: 19
atgaagtctg gctctggaga agggtccccg acctcgctgt gggggctcct gtttctctcc   60
gccgcgctct cgctctggcc gacgagtgga gaaatctgtg gcccgggcat cgacatccgc  120
aacgactatc agcagctgaa gcgcctggag aactgcacgg tgatcgaggg ctacctccac  180

```
atcctgctca tctccaaggc cgaggactac cgcagctacc gcttccccaa gctcacggtc    240
atcaccgagt acttgctgtt gttccgagtg gctggcctag agagcctcgg agacctgttc    300
cccaacctca cggtaatccg cggctggaaa ctcttctaca actacgccct ggtcatcttt    360
gagatgacca atctcaagga tattgggctt tacaacctga ggaacattac tcgggggggcc    420 atcaggattg agaaaaatgc tgacctctgt tacctctcca ctgtggactg gtccctgatc    480
ctggatgcag tgtccaataa ctacattgtg gggaataagc ccccaaagga atgcggggac    540
ctgtgtccgg ggaccatgga ggagaagccg atgtgcgaga agaccaccat caacaatgag    600
tacaactacc gctgctggac cacaaaccgc tgccagaaaa tgtgcccgag tgcctgtggg    660
aagagggcat gcaccgagaa caacgagtgc tgccaccccg agtgcctggg cagctgcagc    720
gcgcctgaca cgacacggc ctgtgtagct tgccgccact actactacgc cggtgtctgc    780
gtgcctgcct gcccgcccaa cacctacagg tttgagggct ggcgctgtgt ggaccgtgac    840
ttctgcgcca acatcctcag tgccgagagc agcgactccg agggtttcgt gatccacgac    900
ggcgagtgca tgcaggagtg cccctcaggc ttcatccgca acggcagcca gagcatgtac    960
tgcatccctt gtgaaggtcc ttgccccaag gtctgtgagg aagaaaagaa aacaaagacc    1020
attgattctg ttacttctgc tcagatgctt caaggatgca ccatcttcaa gggcaatttg    1080
ctcattaaca tccgacgggg gaataacatt gcttcagaac tggagaactt catgggggctc    1140 atcgaggtgg tgacgggcta cgtgaagatc cgccattccc atgccttggt ctccttgtcc    1200
ttcctaaaaa accttcgcct catcttagga gaggagcagc tagaagggaa ttactccttc    1260
tacgtcctcg acaaccagaa cttgcagcaa ctatgggact gggaccaccg caacctgacc    1320
atcaaagcag ggaaaatgta ctttgctttc aatcccaaat tgtgtgtttc ggaaatttac    1380
cgcatggagg aagtgacggg gactaaaggg cgccaaagca aggggacat aaacaccagg    1440 aacaacgggg aaagagcctc ctgtgaaagt gacgtcctgc atttcacctc caccaccacg    1500
tggaagaatc gcatcatcat aacctggcac cggtaccggc ccctgactac agggatctc    1560 atcagcttca ccgtttacta caaggaagca ccttttaaga atgtcacgga gtatgatggg    1620
caggatgcct gcggctccaa cagctggaac atggtggacg tggacctccc gcccaacaag    1680
gacgtggagc ccggcatctt actgcatggg ctgaagccct ggactcagta cgccgtttac    1740
gtcaaggctg tgaccctcac catggtggag aacgaccata tccgtggggc caagagtgag    1800
atcttgtaca ttcgcaccaa tgcttcagtt ccttccattc ccttggacgt tctttcagca    1860
tcgaactcct cttctcagtt aatcgtgaag tggaaccctc cctctctgcc caacggcaac    1920
ctgagttact acattgtgcg ctggcagcgg cagcctcagg acggctacct ttaccggcac    1980
aattactgct ccaaagacaa aatccccatc aggaagtatg ccgacggcac cattgacatt    2040
gaggaggtca cagagaaccc gaagactgag gtgtgtggtg gagagaaagg gccttgctgc    2100
gcctgcccca aaactgaagc tgagaagcag gccgagaagg aggaggctga gtaccgcaaa    2160
gtctttgaga atttcctgca caactccatc tttgtgccca gacctgaaag gaagcggaga    2220
gatgtcatgc aagtggccaa caccaccatg tccagccgaa gcaggaacac cacggtggca    2280
gacacctaca acatcacaga tctggaagag ctagagacaa gtaccccttt ctttgagagc    2340
agagtggata taaggagag aactgtcatt tctaaccttc ggccttttca cattgtaccgc    2400 attgatatcc acagctgcaa ccacgaggct gagaaactgg gctgcagcgc ctccaacttt    2460
gtctttgcaa ggactatgcc tgcagaagga gcagatgaca ttcctgggcc agtgacctgg    2520
gagccaaggc ctgaaaactc catctttttta aagtggccag aacctgagaa tcccaatgga    2580
```

```
ttgattctaa tgtatgaaat aaaatacgga tcacaagttg aggatcagcg agaatgtgtg      2640
tccagacagg aatacaggaa gtatggaggg gccaagctaa accggctaaa cccggggaac      2700
tacacagccc ggattcaggc tacatctctc tctgggaatg ggtcgtggac agatcctgtg      2760
ttcttctatg tccaggccaa aacaggatac gaaaacttca tccatctgat catcgctctg      2820
cccgtcgctg tcctgttgat cgtgggaggg ttggtgatca tgctgtacgt cttccatada      2880
aagagaaata acagcaggct ggggaatgga gtgctgtacg cgtctgtgaa cccggagtac      2940
ttcagcgctg cggatgtgta cgttcctgat gagtgggagg tggctcggga agatcacc       3000 atgagccggg aacttgggca ggggtcgttt gggatggtct atgaaggagt tgccaagggt      3060
gtggtgaaag acgaacctga aaccagagtg gccattaaaa cagtgaacga ggccgcgagc      3120
atgcgtgaaa ggatcgagtt tctcaacgag gcttctgtga tgaaggagtt caattgtcac      3180
catgtggtgc ggttgctggg tgtggtgtcc cagggccagc caacgctggt catcatggaa      3240
ctgatgacgc ggggcgatct caaaagttat ctccggtctc tgaggccaga aatggagaat      3300
aatccagtcc tagcacctcc aagcctaagc aagatgattc agatggctgg agagattgca      3360
gacggcatgg cataccctca acgccaacaag ttcgtccaca gagaccttgc tgcccggaat      3420
tgcatggtag ccgaggattt cacagtcaaa attggagatt ttgggatgac gcgagatatc      3480
tatgagacag actattaccg gaaaggaggg aaagggctgt tgcccgtgcg ctggatgtct      3540
cccgagtccc tcaaggatgg agtcttcacc acttactcgg acgtctggtc cttcggggtt      3600
gtcctctggg agatcgccac actggccgag cagccctacc agggcttgtc caacgagcaa      3660
gtccttcgct tcgtcatgga gggcggcctt ctggacaagc cagacaactg ccccgacatg      3720
ctgtttgaat tgatgcgcat gtgctggcag tacaacccca agatgaggcc ttccttcctg      3780
gagatcatca gcagcatcaa agacgagatg gagcctggct ccgggaggt ctccttctac       3840 tacagtgagg agaacaagct gccccgagccg gaggagctgg acctggagcc agagaacatg      3900
gagagcgtcc ccctggaccc ctcggcctcc tcgtcctccc tgccactgcc cgacagacac      3960
tcaggacaca aggccgagaa cggcccccggc cctggagtgc tggtgctccg cgccagcttc      4020
gatgagagac agccttacgc acacatgaac ggtggccgca agaacgagcg ggccttgccg      4080
ctgccccagt cttcgacctg cgattataag gatgacgatg acaagtga                   4128
```

<210> SEQ ID NO 20
<211> LENGTH: 1370
<212> TYPE: PRT
<213> ORGANISM: Rattus norvegicus

<400> SEQUENCE: 20

```
Met Lys Ser Gly Ser Gly Gly Ser Pro Thr Ser Leu Trp Gly Leu
1               5                   10                  15

Val Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Phe Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95
```

-continued

Gly Asp Leu Phe Pro Asn Leu Thr Val Ile Arg Gly Trp Lys Leu Phe
              100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Ile Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Leu Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Val Cys Gly Lys Arg Ala Cys
    210                 215                 220

Thr Glu Asn Asn Glu Cys Cys His Pro Glu Cys Leu Gly Ser Cys His
225                 230                 235                 240

Thr Pro Asp Asp Asn Thr Thr Cys Val Ala Cys Arg His Tyr Tyr Tyr
                245                 250                 255

Lys Gly Val Cys Val Pro Ala Cys Pro Pro Gly Thr Tyr Arg Phe Glu
            260                 265                 270

Gly Trp Arg Cys Val Asp Arg Asp Phe Cys Ala Asn Ile Pro Asn Ala
        275                 280                 285

Glu Ser Ser Asp Ser Asp Gly Phe Val Ile His Asp Gly Glu Cys Met
    290                 295                 300

Gln Glu Cys Pro Ser Gly Phe Ile Arg Asn Ser Thr Gln Ser Met Tyr
305                 310                 315                 320

Cys Ile Pro Cys Glu Gly Pro Cys Pro Lys Val Cys Gly Asp Glu Glu
                325                 330                 335

Lys Lys Thr Lys Thr Ile Asp Ser Val Thr Ser Ala Gln Met Leu Gln
            340                 345                 350

Gly Cys Thr Ile Leu Lys Gly Asn Leu Leu Ile Asn Ile Arg Arg Gly
        355                 360                 365

Asn Asn Ile Ala Ser Glu Leu Glu Asn Phe Met Gly Leu Ile Glu Val
    370                 375                 380

Val Thr Gly Tyr Val Lys Ile Arg His Ser His Ala Leu Val Ser Leu
385                 390                 395                 400

Ser Phe Leu Lys Asn Leu Arg Leu Ile Leu Gly Glu Glu Gln Leu Glu
                405                 410                 415

Gly Asn Tyr Ser Phe Tyr Val Leu Asp Asn Gln Asn Leu Gln Gln Leu
            420                 425                 430

Trp Asp Trp Asn His Arg Asn Leu Thr Val Arg Ser Gly Lys Met Tyr
        435                 440                 445

Phe Ala Phe Asn Pro Lys Leu Cys Val Ser Glu Ile Tyr Arg Met Glu
    450                 455                 460

Glu Val Thr Gly Thr Lys Gly Arg Gln Ser Lys Gly Asp Ile Asn Thr
465                 470                 475                 480

Arg Asn Asn Gly Glu Arg Ala Ser Cys Glu Ser Asp Val Leu Arg Phe
                485                 490                 495

Thr Ser Thr Thr Thr Trp Lys Asn Arg Ile Ile Ile Thr Trp His Arg
            500                 505                 510

Tyr Arg Pro Pro Asp Tyr Arg Asp Leu Ile Ser Phe Thr Val Tyr Tyr

```
              515                 520                 525
Lys Glu Ala Pro Phe Lys Asn Val Thr Glu Tyr Asp Gly Gln Asp Ala
            530                 535                 540

Cys Gly Ser Asn Ser Trp Asn Met Val Asp Val Asp Leu Pro Pro Asn
545                 550                 555                 560

Lys Glu Gly Glu Pro Gly Ile Leu Leu His Gly Leu Lys Pro Trp Thr
                565                 570                 575

Gln Tyr Ala Val Tyr Val Lys Ala Val Thr Leu Thr Met Val Glu Asn
            580                 585                 590

Asp His Ile Arg Gly Ala Lys Ser Glu Ile Leu Tyr Ile Arg Thr Asn
            595                 600                 605

Ala Ser Val Pro Ser Ile Pro Leu Asp Val Leu Ser Ala Ser Asn Ser
        610                 615                 620

Ser Ser Gln Leu Ile Val Lys Trp Asn Pro Pro Thr Leu Pro Asn Gly
625                 630                 635                 640

Asn Leu Ser Tyr Tyr Ile Val Arg Trp Gln Arg Gln Pro Gln Asp Gly
                645                 650                 655

Tyr Leu Phe Arg His Asn Tyr Cys Ser Lys Asp Lys Ile Pro Ile Arg
            660                 665                 670

Lys Tyr Ala Asp Gly Thr Ile Asp Val Glu Glu Val Thr Glu Asn Pro
            675                 680                 685

Lys Thr Glu Val Cys Gly Gly Asp Lys Gly Pro Cys Cys Ala Cys Pro
            690                 695                 700

Lys Thr Glu Ala Glu Lys Gln Ala Glu Lys Glu Glu Ala Glu Tyr Arg
705                 710                 715                 720

Lys Val Phe Glu Asn Phe Leu His Asn Ser Ile Phe Val Pro Arg Pro
                725                 730                 735

Glu Arg Arg Arg Arg Asp Val Leu Gln Val Ala Asn Thr Thr Met Ser
            740                 745                 750

Ser Arg Ser Arg Asn Thr Thr Val Ala Asp Thr Tyr Asn Ile Thr Asp
            755                 760                 765

Pro Glu Glu Phe Glu Thr Glu Tyr Pro Phe Phe Glu Ser Arg Val Asp
            770                 775                 780

Asn Lys Glu Arg Thr Val Ile Ser Asn Leu Arg Pro Phe Thr Leu Tyr
785                 790                 795                 800

Arg Ile Asp Ile His Ser Cys Asn His Glu Ala Glu Lys Leu Gly Cys
                805                 810                 815

Ser Ala Ser Asn Phe Val Phe Ala Arg Thr Met Pro Ala Glu Gly Ala
            820                 825                 830

Asp Asp Ile Pro Gly Pro Val Thr Trp Glu Pro Arg Pro Glu Asn Ser
            835                 840                 845

Ile Phe Leu Lys Trp Pro Pro Glu Asn Pro Asn Gly Leu Ile Leu
            850                 855                 860

Met Tyr Glu Ile Lys Tyr Gly Ser Gln Val Glu Asp Gln Arg Glu Cys
865                 870                 875                 880

Val Ser Arg Gln Glu Tyr Arg Lys Tyr Gly Gly Ala Lys Leu Asn Arg
                885                 890                 895

Leu Asn Pro Gly Asn Tyr Thr Ala Arg Ile Gln Ala Thr Ser Leu Ser
            900                 905                 910

Gly Asn Gly Ser Trp Thr Asp Pro Val Phe Phe Tyr Val Pro Ala Lys
            915                 920                 925

Thr Thr Tyr Glu Asn Phe Met His Leu Ile Ile Ala Leu Pro Val Ala
            930                 935                 940
```

```
Ile Leu Leu Ile Val Gly Gly Leu Val Ile Met Leu Tyr Val Phe His
945                 950                 955                 960

Arg Lys Arg Asn Asn Ser Arg Leu Gly Asn Gly Val Leu Tyr Ala Ser
                965                 970                 975

Val Asn Pro Glu Tyr Phe Ser Ala Ala Asp Val Tyr Val Pro Asp Glu
            980                 985                 990

Trp Glu Val Ala Arg Glu Lys Ile Thr Met Asn Arg Glu Leu Gly Gln
        995                 1000                1005

Gly Ser Phe Gly Met Val Tyr Glu Gly Val Ala Lys Gly Val Val
    1010                1015                1020

Lys Asp Glu Pro Glu Thr Arg Val Ala Ile Lys Thr Val Asn Glu
    1025                1030                1035

Ala Ala Ser Met Arg Glu Arg Ile Glu Phe Leu Asn Glu Ala Ser
    1040                1045                1050

Val Met Lys Glu Phe Asn Cys His His Val Val Arg Leu Leu Gly
    1055                1060                1065

Val Val Ser Gln Gly Gln Pro Thr Leu Val Ile Met Glu Leu Met
    1070                1075                1080

Thr Arg Gly Asp Leu Lys Ser Tyr Leu Arg Ser Leu Arg Pro Glu
    1085                1090                1095

Val Glu Asn Asn Leu Val Leu Ile Pro Pro Ser Leu Ser Lys Met
    1100                1105                1110

Ile Gln Met Ala Gly Glu Ile Ala Asp Gly Met Ala Tyr Leu Asn
    1115                1120                1125

Ala Asn Lys Phe Val His Arg Asp Leu Ala Ala Arg Asn Cys Met
    1130                1135                1140

Val Ala Glu Asp Phe Thr Val Lys Ile Gly Asp Phe Gly Met Thr
    1145                1150                1155

Arg Asp Ile Tyr Glu Thr Asp Tyr Tyr Arg Lys Gly Gly Lys Gly
    1160                1165                1170

Leu Leu Pro Val Arg Trp Met Ser Pro Glu Ser Leu Lys Asp Gly
    1175                1180                1185

Val Phe Thr Thr His Ser Asp Val Trp Ser Phe Gly Val Val Leu
    1190                1195                1200

Trp Glu Ile Ala Thr Leu Ala Glu Gln Pro Tyr Gln Gly Leu Ser
    1205                1210                1215

Asn Glu Gln Val Leu Arg Phe Val Met Glu Gly Gly Leu Leu Asp
    1220                1225                1230

Lys Pro Asp Asn Cys Pro Asp Met Leu Phe Glu Leu Met Arg Met
    1235                1240                1245

Cys Trp Gln Tyr Asn Pro Lys Met Arg Pro Ser Phe Leu Glu Ile
    1250                1255                1260

Ile Gly Ser Ile Lys Asp Glu Met Glu Pro Ser Phe Gln Glu Val
    1265                1270                1275

Ser Phe Tyr Tyr Ser Glu Glu Asn Lys Pro Pro Glu Pro Glu Glu
    1280                1285                1290

Leu Glu Met Glu Leu Glu Leu Glu Pro Glu Asn Met Glu Ser Val
    1295                1300                1305

Pro Leu Asp Pro Ser Ala Ser Ser Ala Ser Leu Pro Leu Pro Glu
    1310                1315                1320

Arg His Ser Gly His Lys Ala Glu Asn Gly Pro Gly Val Leu Val
    1325                1330                1335
```

```
Leu Arg Ala Ser Phe Asp Glu Arg Gln Pro Tyr Ala His Met Asn
    1340                1345                1350

Gly Gly Arg Ala Asn Glu Arg Ala Leu Pro Leu Pro Gln Ser Ser
    1355                1360                1365

Thr Cys
    1370

<210> SEQ ID NO 21
<211> LENGTH: 4140
<212> TYPE: DNA
<213> ORGANISM: Rattus norvegicus

<400> SEQUENCE: 21
```

| | | | | | |
|---|---|---|---|---|---|
| atgaagtctg | gctccggagg | agggtccccg | acctcgctgt | gggggctcgt | gtttctctcc | 60 |
| gccgcgctct | cgctctggcc | gacgagtgga | gaaatttgtg | ggcccggcat | tgacatccgc | 120 |
| aacgactatc | agcagctgaa | gcgcctggaa | aactgcacgg | tgatcgaggg | cttcctccac | 180 |
| atcctgctca | tctccaaggc | cgaggactac | cgaagctacc | gcttccccaa | gctcacagtc | 240 |
| atcaccgagt | acttgctgct | gtttcgagtg | gccggcctcg | agagcctggg | agacctcttc | 300 |
| ccgaacctca | cagtcatccg | tggctggaaa | ctcttctaca | attacgcact | ggtcatcttc | 360 |
| gagatgacca | atctcaagga | tattgggctt | tataatctga | ggaacattac | tcgggggggcc | 420 |
| atcaggattg | agaaaaacgc | tgacctctgt | tacctctcca | ccatagactg | gtctctcatc | 480 |
| ttggatgcgg | tgtccaataa | ctacattgtg | gggaacaagc | ccccaaagga | atgtggggac | 540 |
| ctgtgtccag | ggaccttgga | ggagaagccc | atgtgtgaga | agaccaccat | caacaatgag | 600 |
| tacaactacc | gctgctggac | cacaaatcgc | tgccagaaaa | tgtgcccaag | tgtgtgtggg | 660 |
| aagcgagcct | gcaccgagaa | caatgagtgc | tgccacccgg | agtgcctagg | cagctgccac | 720 |
| acaccggacg | acaacacaac | ctgcgtggcc | tgccgacact | actactacaa | aggcgtgtgc | 780 |
| gtgcctgcct | gcccgcctgg | cacctacagg | ttcgagggct | ggcgctgtgt | ggaccgggat | 840 |
| ttctgcgcca | acatccccaa | cgccgagagc | agtgactcag | atggcttcgt | catccacgat | 900 |
| ggcgagtgca | tgcaggagtg | tccatcaggc | ttcatccgca | acagcaccca | gagcatgtac | 960 |
| tgtatcccct | gtgaaggccc | ctgccccaag | gtctgcggcg | atgaagaaaa | gaaaacgaaa | 1020 |
| accatcgatt | ctgtgacgtc | tgcccagatg | ctccaagggt | gcaccatttt | gaagggcaat | 1080 |
| ctgcttatta | acatccggcg | aggcaataac | attgcctcgg | aattggagaa | cttcatgggg | 1140 |
| ctcatcgagg | tggtgactgg | ctacgtgaag | atccgccatt | cccatgcctt | ggtctccttg | 1200 |
| tccttcctga | agaaccttcg | tctcatctta | ggagaggagc | agctagaagg | aaactactcc | 1260 |
| ttctatgtcc | tggacaacca | gaacttgcag | cagctgtggg | actggaacca | ccggaacctg | 1320 |
| accgtcaggt | cagggaaaat | gtacttcgct | ttcaatccca | agctgtgtgt | ctctgaaatt | 1380 |
| taccgaatgg | aggaggtgac | aggaacaaag | ggacggcaga | gcaaggagac | ataaacacc | 1440 |
| aggaacaacg | gagagcgagc | ttcctgtgaa | agtgatgttc | tccgtttcac | ctccaccacc | 1500 |
| acctggaaga | accgcatcat | cataacgtgg | caccggtacc | ggccgccgga | ctaccgggat | 1560 |
| ctcatcagtt | tcacagtcta | ctacaaggag | gcacccttta | aaaacgtcac | ggaatacgac | 1620 |
| gggcaggatg | cctgtggctc | caacagctgg | aacatggtgg | acgtggacct | gcctccgaac | 1680 |
| aaggaggggg | agcctggcat | tttgctgcat | gggctgaagc | cctggaccca | gtatgcagtc | 1740 |
| tatgtcaagg | ctgtgacccc | taccatggtg | gaaaacgacc | acatccgtgg | ggccaaaagt | 1800 |
| gaaatcttgt | acattcgcac | caacgcttca | gttccttcca | ttcctctaga | tgtcctctcg | 1860 |

-continued

```
gcatcaaact cctcctctca gctgatcgtg aagtggaacc ccccaactct gcccaatggt   1920
aacttgagtt actacattgt gaggtggcag cggcagccgc aggatggcta tctgttccgg   1980
cacaactact gctccaaaga caaaataccc atcagaaagt acgccgatgg taccatcgat   2040
gtggaggagg tgacagaaaa tcccaagaca gaagtgtgcg gtggtgataa agggccgtgc   2100
tgtgcctgtc ctaaaaccga agctgagaag caggctgaga aggaggaggc tgagtaccgt   2160
aaagtctttg agaatttcct tcacaactcc atctttgtgc ccagacctga gaggaggcgg   2220
agagatgtcc tgcaggtggc taacaccacc atgtccagcc gaagcaggaa caccacggta   2280
gctgacacct acaatatcac agacccggaa gagttcgaga cagaataccc tttctttgag   2340
agcagagtgg ataacaagga gaggactgtc atttccaacc tccggccttt cactctgtac   2400
cgtatcgata tccacagctg caaccacgag gctgagaagc tgggctgcag cgcctccaac   2460
tttgtctttg caagaaccat gccagcagaa ggagcagatg acattcctgg cccagtgacc   2520
tgggagccaa gacctgaaaa ctccatcttt ttaaagtggc cagaaccaga gaaccccaac   2580
ggattgattc taatgtatga aataaaatac ggatcgcaag tcgaggatca gcgggaatgt   2640
gtgtccagac aggagtacag gaagtatgga ggggccaaac ttaaccgtct aaacccaggg   2700
aactatacgg cccggattca ggctacctcc ctctctggga tgggtcgtg acagatcct   2760
gtgttcttct atgtcccagc caaaacaacg tatgagaatt tcatgcatct gatcattgct   2820
ctgccggttg ccatcctgct gattgtgggg ggcctggtaa tcatgctgta tgtcttccat   2880
agaaagagga ataacagcag attgggcaac ggggtgctgt acgcctctgt gaaccccgag   2940
tatttcagcg cagctgatgt gtacgtgcct gatgaatggg aggtagctcg ggagaagatc   3000
accatgaacc gggagctcgg acaagggtcc ttcgggatgg tctatgaagg agtggccaag   3060
ggcgtggtca aggacgagcc tgaaaccaga gtggccatca agacagtgaa tgaggctgca   3120
agtatgcgtg agagaattga gtttctcaac gaggcctcag tgatgaagga gttcaactgt   3180
caccatgtgt tccggttgct gggtgtagta tcccaaggcc agcccaccct ggtcatcatg   3240
gaactaatga cacgtggcga tctcaaaagt tatctccggt ctctaaggcc agaggtggag   3300
cagaataatc tagtcctgat tcctccgagc ttaagcaaga tgatccagat ggctggagag   3360
attgcagatg gcatggccta cctcaatgcc aacaagttcg tccacagaga cctggctgct   3420
cggaactgca tggtagctga agattttcaca gtcaaaattg gagattttgg tatgacacga   3480
gacatctacg agacggacta ctaccggaaa ggcgggaagg gcttgctgcc tgtgcgctgg   3540
atgtctcccg agtccctcaa ggatggcgtc ttcaccactc attccgatgt ctggtccttt   3600
ggggtcgtcc tctgggagat cgccactctg gctgagcagc cgtaccaggg cctgtccaac   3660
gagcaagttc ttcgtttcgt catggaggc ggccttctgg acaagccgga taactgcccc   3720
gatatgctgt ttgaacttat gcgcatgtgc tggcagtaca accccaagat gcggccctcc   3780
ttcctggaga tcatcggaag catcaaggat gagatggagc ccagtttcca ggaggtctcc   3840
ttctactaca gcgaggagaa caagcctcca gagccggagg agctggagat ggagctggag   3900
ctggagcccg agaacatgga gagcgtcccg ctggacccct tcggcctcctc agcctccctg   3960
cctctgcctag aaagacactc aggacacaag gctgagaacg ccctggcgt gctggttctc   4020
cgtgccagtt ttgatgagag acagccttac gctcacatga atgggggacg cgccaacgag   4080
agggccttgc ctctgcccca gtcctcaacc tgcgattata aggatgacga tgacaagtga   4140
```

<210> SEQ ID NO 22
<211> LENGTH: 4142

```
<212> TYPE: DNA
<213> ORGANISM: Artificial Sequence
<220> FEATURE:
<223> OTHER INFORMATION: Synthetic sequence, hIGF-1R_FLAG

<400> SEQUENCE: 22
gaattcatga agtctggctc cggaggaggg tccccgacct cgctgtgggg gctcctgttt      60
ctctccgccg cgctctcgct ctggccgacg agtggagaaa tctgcgggcc aggcatcgac     120
atccgcaacg actatcagca gctgaagcgc ctggagaact gcacggtgat cgagggctac     180
ctccacatcc tgctcatctc caaggccgag gactaccgca gctaccgctt ccccaagctc     240
acggtcatta ccgagtactt gctgctgttc cgagtggctg cctcgagag cctcggagac     300
ctcttcccca acctcacggt catccgcggc tggaaactct tctacaacta cgccctggtc     360
atcttcgaga tgaccaatct caaggatatt gggctttaca acctgaggaa cattactcgg     420
ggggccatca ggattgagaa aaatgctgac ctctgttacc tctccactgt ggactggtcc     480
ctgatcctgg atgcggtgtc caataactac attgtgggga ataagccccc aaaggaatgt     540
ggggacctgt gtccagggac catggaggag aagccgatgt gtgagaagac caccatcaac     600
aatgagtaca actaccgctg ctggaccaca aaccgctgcc agaaaatgtg cccaagcacg     660
tgtgggaagc gggcgtgcac cgagaacaat gagtgctgcc accccgagtg cctgggcagc     720
tgcagcgcgc tgacaacga cacggcctgt gtagcttgcc gccactacta ctatgccggt     780
gtctgtgtgc ctgcctgccc gcccaacacc tacaggtttg agggctggcg ctgtgtggac     840
cgtgacttct cgccaacat cctcagcgcc gagagcagcg actccgaggg gtttgtgatc     900
cacgacggcg agtgcatgca ggagtgcccc tcgggcttca tccgcaacgg cagccagagc     960
atgtactgca tcccttgtga aggtccttgc ccgaaggtct gtgaggaaga aaagaaaaca    1020
aagaccattg attctgttac ttctgctcag atgctccaag gatgcaccat cttcaagggc    1080
aatttgctca ttaacatccg acgggggaat aacattgctt cagagctgga aacttcatg    1140
gggctcatcg aggtggtgac gggctacgtg aagatccgcc attctcatgc cttggtctcc    1200
ttgtccttcc taaaaaacct tcgcctcatc ctaggagagg agcagctaga agggaattac    1260
tccttctacg tcctcgacaa ccagaacttg cagcaactgt gggactggga ccaccgcaac    1320
ctgaccatca agcagggaa aatgtacttt gctttcaatc ccaaattatg tgtttccgaa    1380
atttaccgca tggaggaagt gacggggact aaagggcgcc aaagcaaagg ggacataaac    1440
accaggaaca cggggagag agcctcctgt gaaagtgacg tcctgcattt cacctccacc    1500
accacgtcga gaatcgcat catcataacc tggaccggt accggccccc tgactacagg    1560
gatctcatca gcttcaccgt ttactacaag gaagcaccct ttaagaatgt cacagagtat    1620
gatgggcagg atgcctgcgg ctccaacagc tggaacatgg tggacgtgga cctcccgccc    1680
aacaaggacg tggagcccgg catcttacta catgggctga gccctggac tcagtacgcc    1740
gtttacgtca aggctgtgac cctcaccatg gtggagaacg accatatccg tgggccaag    1800
agtgagatct tgtacattcg caccaatgct tcagttcctt ccattcctt ggacgttctt    1860
tcagcatcga actcctcttc tcagttaatc gtgaagtgga accctccctc tctgcccaac    1920
ggcaacctga gttactacat tgtgcgctgg cagcggcagc ctcaggacgg ctacctttac    1980
cggcacaatt actgctccaa agacaaaatc cccatcagga gtatgccga cggcaccatc    2040
gacattgagg aggtcacaga gaaccccaag actgaggtgt gtggtgggga aaagggcct    2100
tgctgcgcct gccccaaaac tgaagccgag aagcaggccg agaaggagga ggctgaatac    2160
```

```
cgcaaagtct ttgagaattt cctgcacaac tccatcttcg tgcccagacc tgaaaggaag    2220
cggagagatg tcatgcaagt ggccaacacc accatgtcca gccgaagcag aacaccacg     2280 gccgcagaca cctacaacat caccgacccg aagagctgg agacagagta cccttctt      2340 gagagcagag tggataacaa ggagagaact gtcatttcta accttcggcc tttcacattg    2400
taccgcatcg atatccacag ctgcaaccac gaggctgaga agctgggctg cagcgcctcc    2460
aacttcgtct ttgcaaggac tatgcccgca aaggagcag atgacattcc tgggccagtg     2520
acctgggagc caaggcctga aaactccatc ttttttaaagt ggccggaacc tgagaatccc   2580
aatggattga ttctaatgta tgaaataaaa tacggatcac aagttgagga tcagcgagaa    2640
tgtgtgtcca gacaggaata caggaagtat ggaggggcca agctaaaccg gctaaacccg    2700
gggaactaca cagcccggat tcaggccaca tctctctctg gaatgggtc gtggacagat     2760 cctgtgttct tctatgtcca ggccaaaaca ggatatgaaa acttcatcca tctgatcatc    2820
gctctgcccg tcgctgtcct gttgatcgtg ggagggttgg tgattatgct gtacgtcttc    2880
catagaaaga gaaataacag caggctgggg aatgagtgc tgtatgcctc tgtgaacccg     2940
gagtacttca cgcgctgctga tgtgtacgtt cctgatgagt gggaggtggc tcgggagaag   3000
atcaccatga gccgggaact tgggcagggg tcgtttggga tggtctatga aggagttgcc    3060
aagggtgtgg tgaaagatga acctgaaacc agagtggcca ttaaaacagt gaacgaggcc    3120
gcaagcatgc gtgagaggat tgagtttctc aacgaagctt ctgtgatgaa ggagttcaat    3180
tgtcaccatg tggtgcgatt gctgggtgtg gtgtcccaag gccagccaac actggtcatc    3240
atggaactga tgacacgggg cgatctcaaa agttatctcc ggtctctgag gccagaaatg    3300
gagaataatc cagtcctagc acctccaagc ctgagcaaga tgattcagat ggccggagag    3360
attgcagacg gcatggcata cctcaacgcc aataagttcg tccacagaga ccttgctgcc    3420
cggaattgca tggtagccga agatttcaca gtcaaaatcg gagattttgg tatgacgcga    3480
gatatctatg agacagacta ttaccggaaa ggagggaaag gctgctgcc cgtgcgctgg    3540 atgtctcctg agtccctcaa ggatggagtc ttcaccactt actcggacgt ctggtccttc    3600
ggggtcgtcc tctgggagat cgccacactg gccgagcagc cctaccaggg cttgtccaac    3660
gagcaagtcc ttcgcttcgt catggagggc ggccttctgg acaagccaga caactgtcct    3720
gacatgctgt ttgaactgat gcgcatgtgc tggcagtata accccaagat gaggccttcc    3780
ttcctggaga tcatcagcag catcaaagag gagatggagc ctggcttccg ggaggtctcc    3840
ttctactaca gcgaggagaa caagctgccc gagccggagg agctggacct ggagccagag    3900
aacatggaga gcgtccccct ggaccccctcg gcctcctcgt cctccctgcc actgcccgac    3960
agacactcag acacaaggc cgagaacggc cccggccctg gggtgctggt cctccgcgcc    4020
agcttcgacg agagacagcc ttacgcccac atgaacgggg gccgcaagaa cgagcgggcc    4080
ttgccgctgc cccagtcttc gacctgcgac tacaaagacg atgacgacaa gtgagcggcc   4140
gc                                                                 4142
```

<210> SEQ ID NO 23
<211> LENGTH: 4142
<212> TYPE: DNA
<213> ORGANISM: Artificial Sequence
<220> FEATURE:
<223> OTHER INFORMATION: Synthetic sequence, hIGF1R-D245N-A247T-
      E294D_FLAG

<400> SEQUENCE: 23

-continued

```
gaattcatga agtctggctc cggaggaggg tccccgacct cgctgtgggg gctcctgttt      60
ctctccgccg cgctctcgct ctggccgacg agtggagaaa tctgcgggcc aggcatcgac     120
atccgcaacg actatcagca gctgaagcgc ctggagaact gcacggtgat cgagggctac     180
ctccacatcc tgctcatctc caaggccgag gactaccgca gctaccgctt ccccaagctc     240
acggtcatta ccgagtactt gctgctgttc cgagtggctg gcctcgagag cctcggagac     300
ctcttcccca acctcacggt catccgcggc tggaaactct tctacaacta cgccctggtc     360
atcttcgaga tgaccaatct caaggatatt gggctttaca acctgaggaa cattactcgg     420
ggggccatca ggattgagaa aaatgctgac ctctgttacc tctccactgt ggactggtcc     480
ctgatcctgg atgcggtgtc caataactac attgtgggga ataagccccc aaaggaatgt     540
ggggacctgt gtccagggac catggaggag aagccgatgt gtgagaagac caccatcaac     600
aatgagtaca actaccgctg ctggaccaca aaccgctgcc agaaaatgtg cccaagcacg     660
tgtgggaagc gggcgtgcac cgagaacaat gagtgctgcc accccgagtg cctgggcagc     720
tgcagcgcgc tgacaacaa cacgaccgt gtagcttgcc gccactacta ctatgccggt      780
gtctgtgtgc ctgcctgccc gcccaacacc tacaggtttg agggctggcg ctgtgtggac     840
cgtgacttct gcgccaacat cctcagcgcc gagagcagcg actccgacgg gtttgtgatc     900
cacgacggcg agtgcatgca ggagtgcccc tcgggcttca tccgcaacgg cagccagagc     960
atgtactgca tccccttgtga aggtccttgc ccgaaggtct gtgaggaaga aaagaaaaca    1020
aagaccattg attctgttac ttctgctcag atgctccaag gatgcaccat cttcaagggc    1080
aatttgctca ttaacatccg acgggggaat aacattgctt cagagctgga gaacttcatg    1140
gggctcatcg aggtggtgac gggctacgtg aagatccgcc attctcatgc cttggtctcc    1200
ttgtccttcc taaaaaacct tcgcctcatc ctaggagagg agcagctaga agggaattac    1260
tccttctacg tcctcgacaa ccagaacttg cagcaactgt gggactggga ccaccgcaac    1320
ctgaccatca aagcagggaa aatgtacttt gctttcaatc ccaaattatg tgtttccgaa    1380
atttaccgca tggaggaagt gacggggact aaagggcgcc aaagcaaagg ggacataaac    1440
accaggaaca acggggagag agcctcctgt gaaagtgacg tcctgcattt cacctccacc    1500
accacgtcga agaatcgcat catcataacc tggcaccggt accggccccc tgactacagg    1560
gatctcatca gcttcaccgt ttactacaag gaagcaccct ttaagaatgt cacagagtat    1620
gatgggcagg atgcctgcgg ctccaacagc tggaacatgg tggacgtgga cctcccgccc    1680
aacaaggacg tggagcccgg catcttacta catgggctga agccctggac tcagtacgcc    1740
gtttacgtca aggctgtgac cctcaccatg gtggagaacg accatatccg tggggccaag    1800
agtgagatct tgtacattcg caccaatgct tcagttcctt ccattccctt ggacgttctt    1860
tcagcatcga actcctcttc tcagttaatc gtgaagtgga accctccctc tctgcccaac    1920
ggcaacctga gttactacat tgtgcgctgg cagcggcagc ctcaggacgg ctacctttac    1980
cggcacaatt actgctccaa agacaaaatc cccatcagga agtatgccga cggcaccatc    2040
gacattgagg aggtcacaga gaaccccaag actgaggtgt gtggtgggga gaagggcct     2100 tgctgcgcct gccccaaaac tgaagccgag aagcaggccg agaaggagga ggctgaatac    2160
cgcaaagtct ttgagaattt cctgcacaac tccatcttcg tgcccagacc tgaaaggaag    2220
cggagagatg tcatgcaagt ggccaacacc accatgtcca gccgaagcag gaacaccacg    2280
gccgcagaca cctacaacat caccgacccg gaagagctgg agacagagta cccctttcttt    2340 gagagcagag tggataacaa ggagagaact gtcatttcta accttcggcc tttcacattg    2400
```

```
taccgcatcg atatccacag ctgcaaccac gaggctgaga agctgggctg cagcgcctcc   2460
aacttcgtct ttgcaaggac tatgcccgca gaaggagcag atgacattcc tgggccagtg   2520
acctgggagc caaggcctga aaactccatc tttttaaagt ggccggaacc tgagaatccc   2580
aatggattga ttctaatgta tgaaataaaa tacggatcac aagttgagga tcagcgagaa   2640
tgtgtgtcca gacaggaata caggaagtat ggaggggcca agctaaaccg gctaaacccg   2700
gggaactaca cagcccggat tcaggccaca tctctctctg gaatgggtc gtggacagat    2760
cctgtgttct tctatgtcca ggccaaaaca ggatatgaaa acttcatcca tctgatcatc   2820
gctctgcccg tcgctgtcct gttgatcgtg ggagggttgg tgattatgct gtacgtcttc   2880
catagaaaga gaaataacag caggctgggg aatggagtgc tgtatgcctc tgtgaacccg   2940
gagtacttca gcgctgctga tgtgtacgtt cctgatgagt gggaggtggc tcgggagaag   3000
atcaccatga gccgggaact gggcagggg tcgtttggga tggtctatga aggagttgcc    3060
aagggtgtgg tgaaagatga acctgaaacc agagtggcca ttaaaacagt gaacgaggcc   3120
gcaagcatgc gtgagaggat tgagtttctc aacgaagctt ctgtgatgaa ggagttcaat   3180
tgtcaccatg tggtgcgatt gctgggtgtg gtgtcccaag ccagccaac actggtcatc    3240
atggaactga tgacacgggg cgatctcaaa agttatctcc ggtctctgag gccagaaatg   3300
gagaataatc cagtcctagc acctccaagc ctgagcaaga tgattcagat ggccggagag   3360
attgcagacg gcatggcata cctcaacgcc aataagttcg tccacagaga ccttgctgcc   3420
cggaattgca tggtagccga agatttcaca gtcaaaatcg gagattttgg tatgacgcga   3480
gatatctatg agacagacta ttaccggaaa ggagggaaag gctgctgcc cgtgcgctgg    3540
atgtctcctg agtccctcaa ggatggagtc ttcaccactt actcggacgt ctggtccttc   3600
ggggtcgtcc tctgggagat cgccacactg gccgagcagc cctaccaggg cttgtccaac   3660
gagcaagtcc ttcgcttcgt catggagggc ggccttctgg acaagccaga caactgtcct   3720
gacatgctgt ttgaactgat gcgcatgtgc tggcagtata cccaagat gaggccttcc     3780
ttcctggaga tcatcagcag catcaaagag gagatggagc ctggcttccg ggaggtctcc   3840
ttctactaca gcgaggagaa caagctgccc gagccggagg agctggacct ggagccagag   3900
aacatggaga gcgtccccct ggacccctcg gcctcctcgt cctccctgcc actgcccgac   3960
agacactcag gacacaaggc cgagaacggc cccggccctg gggtgctggt cctccgcgcc   4020
agcttcgacg agagacagcc ttacgcccac atgaacgggg gccgcaagaa cgagcgggcc   4080
ttgccgctgc cccagtcttc gacctgcgac tacaaagacg atgacgacaa gtgagcggcc   4140
gc                                                                  4142
```

<210> SEQ ID NO 24
<211> LENGTH: 4142
<212> TYPE: DNA
<213> ORGANISM: Artificial Sequence
<220> FEATURE:
<223> OTHER INFORMATION: Synthetic sequence, hIGF1R-G315S-S316T_FLAG

<400> SEQUENCE: 24

```
gaattcatga agtctggctc cggaggaggg tccccgacct cgctgtgggg gctcctgttt    60
ctctccgccg cgctctcgct ctggccgacg agtggagaaa tctgcgggcc aggcatcgac   120
atccgcaacg actatcagca gctgaagcgc ctggagaact gcacggtgat cgagggctac   180
ctccacatcc tgctcatctc caaggccgag gactaccgca gctaccgctt ccccaagctc   240
```

```
acggtcatta ccgagtactt gctgctgttc cgagtggctg gcctcgagag cctcggagac    300
ctcttcccca acctcacggt catccgcggc tggaaactct tctacaacta cgccctggtc    360
atcttcgaga tgaccaatct caaggatatt gggctttaca acctgaggaa cattactcgg    420
ggggccatca ggattgagaa aaatgctgac ctctgttacc tctccactgt ggactggtcc    480
ctgatcctgg atgcggtgtc aataactac attgtgggga ataagcccc aaaggaatgt     540
ggggacctgt gtccagggac catggaggag aagccgatgt gtgagaagac caccatcaac    600
aatgagtaca actaccgctg ctggaccaca aaccgctgcc agaaaatgtg cccaagcacg    660
tgtgggaagc gggcgtgcac cgagaacaat gagtgctgcc accccgagtg cctgggcagc    720
tgcagcgcgc ctgacaacga cacggcctgt gtagcttgcc gccactacta ctatgccggt    780
gtctgtgtgc ctgcctgccc gcccaacacc tacaggtttg agggctggcg ctgtgtggac    840
cgtgacttct gcgccaacat cctcagcgcc gagagcagcg actccgaggg gtttgtgatc    900
cacgacggcg agtgcatgca ggagtgcccc tcgggcttca tccgcaacag cacccagagc    960
atgtactgca tcccttgtga aggtccttgc ccgaaggtct gtgaggaaga aagaaaaca    1020
aagaccattg attctgttac ttctgctcag atgctccaag gatgcaccat cttcaagggc    1080
aatttgctca ttaacatccg acgggggaat aacattgctt cagagctgga gaacttcatg    1140
gggctcatcg aggtggtgac gggctacgtg aagatccgcc attctcatgc cttggtctcc    1200
ttgtccttcc taaaaaacct tcgcctcatc ctaggagagg agcagctaga agggaattac    1260
tccttctacg tcctcgacaa ccagaacttg cagcaactgt gggactggga ccaccgcaac    1320
ctgaccatca aagcagggaa aatgtacttt gctttcaatc ccaaattatg tgtttccgaa    1380
atttaccgca tggaggaagt gacggggact aaagggcgcc aaagcaaagg ggacataaac    1440
accaggaaca acggggagag agcctcctgt gaaagtgacg tcctgcattt cacctccacc    1500
accacgtcga agaatcgcat catcataacc tggcaccggt accggccccc tgactacagg    1560
gatctcatca gcttcaccgt ttactacaag gaagcaccct taagaatgt cacagagtat    1620
gatgggcagg atgcctgcgg ctccaacagc tggaacatgg tggacgtgga cctcccgccc    1680
aacaaggacg tggagcccgg catcttacta catgggctga agccctggac tcagtacgcc    1740
gtttacgtca aggctgtgac cctcaccatg gtggagaacg accatatccg tggggccaag    1800
agtgagatct tgtacattcg caccaatgct tcagttcctt ccattccctt ggacgttctt    1860
tcagcatcga actcctcttc tcagttaatc gtgaagtgga accctccctc tctgcccaac    1920
ggcaacctga gttactacat tgtgcgctgg cagcggcagc ctcaggacgg ctacctttac    1980
cggcacaatt actgctccaa agacaaaatc cccatcagga agtatgccga cggcaccatc    2040
gacattgagg aggtcacaga gaaccccaag actgaggtgt gtggtgggga gaagggcct   2100
tgctgcgcct gccccaaaac tgaagccgag aagcaggccg agaaggagga ggctgaatac   2160
cgcaaagtct ttgagaattt cctgcacaac tccatcttcg tgcccagacc tgaaaggaag   2220
cggagagatg tcatgcaagt ggccaacacc accatgtcca gccgaagcag gaacaccacg   2280
gccgcagaca cctacaacat caccgacccg gaagagctgg agacagagta ccctttcttt   2340
gagagcagag tggataacaa ggagagaact gtcatttcta accttcggcc tttcacattg   2400
taccgcatcg atatccacag ctgcaaccac gaggctgaga agctgggctg cagcgcctcc   2460
aacttcgtct ttgcaaggac tatgcccgca gaaggagcag atgacattcc tgggccagtg   2520
acctgggagc caaggcctga aaactccatc tttttaaagt ggccggaacc tgagaatccc   2580
aatggattga ttctaatgta tgaaataaaa tacggatcac aagttgagga tcagcgagaa   2640
```

```
tgtgtgtcca gacaggaata caggaagtat ggaggggcca agctaaaccg gctaaacccg    2700
gggaactaca cagcccggat tcaggccaca tctctctctg ggaatgggtc gtggacagat    2760
cctgtgttct tctatgtcca ggccaaaaca ggatatgaaa acttcatcca tctgatcatc    2820
gctctgcccg tcgctgtcct gttgatcgtg ggagggttgg tgattatgct gtacgtcttc    2880
catagaaaga gaaataacag caggctgggg aatggagtgc tgtatgcctc tgtgaacccg    2940
gagtacttca gcgctgctga tgtgtacgtt cctgatgagt gggaggtggc tcgggagaag    3000
atcaccatga gccgggaact tgggcagggg tcgtttggga tggtctatga aggagttgcc    3060
aagggtgtgg tgaaagatga acctgaaacc agagtggcca ttaaaacagt gaacgaggcc    3120
gcaagcatgc gtgagaggat tgagtttctc aacgaagctt ctgtgatgaa ggagttcaat    3180
tgtcaccatg tggtgcgatt gctgggtgtg gtgtcccaag ccagccaac actggtcatc     3240 atggaactga tgacacgggg cgatctcaaa agttatctcc ggtctctgag gccagaaatg    3300
gagaataatc cagtcctagc acctccaagc ctgagcaaga tgattcagat ggccggagag    3360
attgcagacg gcatggcata cctcaacgcc aataagttcg tccacagaga ccttgctgcc    3420
cggaattgca tggtagccga agatttcaca gtcaaaatcg gagattttgg tatgacgcga    3480
gatatctatg agacagacta ttaccggaaa ggagggaaag gctgctgcc cgtgcgctgg    3540 atgtctcctg agtccctcaa ggatggagtc ttcaccactt actcggacgt ctggtccttc    3600
ggggtcgtcc tctgggagat cgccacactg gccgagcagc cctaccaggg cttgtccaac    3660
gagcaagtcc ttcgcttcgt catggagggc ggccttctgg acaagccaga caactgtcct    3720
gacatgctgt ttgaactgat gcgcatgtgc tggcagtata cccccaagat gaggccttcc    3780
ttcctggaga tcatcagcag catcaaagag gagatggagc ctggcttccg ggaggtctcc    3840
ttctactaca gcgaggagaa caagctgccc gagccggagg agctggacct ggagccagag    3900
aacatggaga gcgtccccct ggaccccctcg gcctcctcgt cctccctgcc actgcccgac    3960
agacactcag gacacaaggc cgagaacggc cccggccctg gggtgctggt cctccgcgcc    4020
agcttcgacg agagacagcc ttacgcccac atgaacgggg gccgcaagaa cgagcgggcc    4080
ttgccgctgc cccagtcttc gacctgcgac tacaaagacg atgacgacaa gtgagcggcc    4140
gc                                                                  4142
```

<210> SEQ ID NO 25
<211> LENGTH: 239
<212> TYPE: PRT
<213> ORGANISM: Oryctolagus cuniculus

<400> SEQUENCE: 25

```
Glu Met Thr Asn Leu Lys Asp Ile Gly Leu Tyr Asn Leu Arg Asn Ile
1               5                   10                  15

Thr Arg Gly Ala Ile Arg Ile Glu Lys Asn Ala Asp Leu Cys Tyr Leu
            20                  25                  30

Ser Thr Val Asp Trp Ser Leu Ile Leu Asp Ala Val Ser Asn Asn Tyr
        35                  40                  45

Ile Val Gly Asn Lys Ser Pro Lys Glu Cys Gly Asp Met Cys Pro Gly
    50                  55                  60

Thr Leu Glu Glu Lys Pro Leu Cys Glu Lys Thr Ala Ile Asn Asn Glu
65                  70                  75                  80

Tyr Asn Tyr Arg Cys Trp Thr Thr Asn Arg Cys Gln Lys Met Cys Pro
                85                  90                  95
```

```
Ser Ala Cys Gly Lys Arg Ala Cys Thr Glu Asn Asn Glu Cys Cys His
            100                 105                 110

Pro Glu Cys Leu Gly Ser Cys His Ala Pro Asp Asp Thr Ala Cys
            115                 120                 125

Val Ala Cys Arg His Tyr Tyr Phe Ser Gly Val Cys Val Pro Ala Cys
            130                 135                 140

Pro Pro Asn Thr Tyr Arg Phe Glu Gly Trp Arg Cys Val Asp Arg Asp
145                 150                 155                 160

Phe Cys Ala Asn Ile Pro Asn Ala Asp Gly Asp Ser Glu Gly Phe
            165                 170                 175

Val Ile His Asp Gly Glu Cys Met Gln Glu Cys Pro Ser Gly Phe Ile
            180                 185                 190

Arg Asn Gly Ser Gln Ser Met Phe Cys Ile Pro Cys Glu Gly Pro Cys
            195                 200                 205

Pro Lys Val Cys Glu Glu Asp Lys Lys Thr Lys Thr Ile Asp Ser Val
            210                 215                 220

Asn Ser Ala Gln Met Leu Gln Gly Cys Thr Ile Phe Lys Gly Asn
225                 230                 235

<210> SEQ ID NO 26
<211> LENGTH: 240
<212> TYPE: PRT
<213> ORGANISM: Mus musculus

<400> SEQUENCE: 26

Glu Met Thr Asn Leu Lys Asp Ile Gly Leu Tyr Asn Leu Arg Asn Ile
1               5                   10                  15

Thr Arg Gly Ala Ile Arg Ile Glu Lys Asn Ala Asp Leu Cys Tyr Leu
            20                  25                  30

Ser Thr Ile Asp Trp Ser Leu Ile Leu Asp Ala Val Ser Asn Asn Tyr
            35                  40                  45

Ile Val Gly Asn Lys Pro Pro Lys Glu Cys Gly Asp Leu Cys Pro Gly
            50                  55                  60

Thr Leu Glu Glu Lys Pro Met Cys Glu Lys Thr Thr Ile Asn Asn Glu
65                  70                  75                  80

Tyr Asn Tyr Arg Cys Trp Thr Thr Asn Arg Cys Gln Lys Met Cys Pro
            85                  90                  95

Ser Val Cys Gly Lys Arg Ala Cys Thr Glu Asn Asn Glu Cys Cys His
            100                 105                 110

Pro Glu Cys Leu Gly Ser Cys His Thr Pro Asp Asp Asn Thr Thr Cys
            115                 120                 125

Val Ala Cys Arg His Tyr Tyr Tyr Lys Gly Val Cys Val Pro Ala Cys
            130                 135                 140

Pro Pro Gly Thr Tyr Arg Phe Glu Gly Trp Arg Cys Val Asp Arg Asp
145                 150                 155                 160

Phe Cys Ala Asn Ile Pro Asn Ala Glu Ser Asp Ser Asp Gly Phe
            165                 170                 175

Val Ile His Asp Asp Glu Cys Met Gln Glu Cys Pro Ser Gly Phe Ile
            180                 185                 190

Arg Asn Ser Thr Gln Ser Met Tyr Cys Ile Pro Cys Glu Gly Pro Cys
            195                 200                 205

Pro Lys Val Cys Gly Asp Glu Lys Lys Thr Lys Thr Ile Asp Ser
            210                 215                 220

Val Thr Ser Ala Gln Met Leu Gln Gly Cys Thr Ile Leu Lys Gly Asn
225                 230                 235                 240
```

<210> SEQ ID NO 27
<211> LENGTH: 240
<212> TYPE: PRT
<213> ORGANISM: Mus musculus

<400> SEQUENCE: 27

Glu Met Thr Asn Leu Lys Asp Ile Gly Leu Tyr Asn Leu Arg Asn Ile
1               5                   10                  15

Thr Arg Gly Ala Ile Arg Ile Glu Lys Asn Ala Asp Leu Cys Tyr Leu
            20                  25                  30

Ser Thr Ile Asp Trp Ser Leu Ile Leu Asp Ala Val Ser Asn Asn Tyr
        35                  40                  45

Ile Val Gly Asn Lys Pro Pro Lys Glu Cys Gly Asp Leu Cys Pro Gly
    50                  55                  60

Thr Leu Glu Glu Lys Pro Met Cys Glu Lys Thr Thr Ile Asn Asn Glu
65                  70                  75                  80

Tyr Asn Tyr Arg Cys Trp Thr Thr Asn Arg Cys Gln Lys Met Cys Pro
                85                  90                  95

Ser Val Cys Gly Lys Arg Ala Cys Thr Glu Asn Asn Glu Cys Cys His
            100                 105                 110

Pro Glu Cys Leu Gly Ser Cys His Thr Pro Asp Asp Asn Thr Thr Cys
        115                 120                 125

Val Ala Cys Arg His Tyr Tyr Tyr Lys Gly Val Cys Val Pro Ala Cys
    130                 135                 140

Pro Pro Gly Thr Tyr Arg Phe Glu Gly Trp Arg Cys Val Asp Arg Asp
145                 150                 155                 160

Phe Cys Ala Asn Ile Pro Asn Ala Glu Ser Ser Asp Ser Asp Gly Phe
                165                 170                 175

Val Ile His Asp Asp Glu Cys Met Gln Glu Cys Pro Ser Gly Phe Ile
            180                 185                 190

Arg Asn Ser Thr Gln Ser Met Tyr Cys Ile Pro Cys Glu Gly Pro Cys
        195                 200                 205

Pro Lys Val Cys Gly Asp Glu Glu Lys Lys Thr Lys Thr Ile Asp Ser
    210                 215                 220

Val Thr Ser Ala Gln Met Leu Gln Gly Cys Thr Ile Leu Lys Gly Asn
225                 230                 235                 240

<210> SEQ ID NO 28
<211> LENGTH: 239
<212> TYPE: PRT
<213> ORGANISM: Lepus brachyurus

<400> SEQUENCE: 28

Glu Met Thr Asn Leu Lys Asp Ile Gly Leu Tyr Asn Leu Arg Asn Ile
1               5                   10                  15

Thr Arg Gly Ala Ile Arg Ile Glu Lys Asn Ala Asp Leu Cys Tyr Leu
            20                  25                  30

Ser Thr Val Asp Trp Ser Leu Ile Leu Asp Ala Val Ser Asn Asn Tyr
        35                  40                  45

Ile Val Gly Asn Lys Ser Pro Lys Glu Cys Gly Asp Met Cys Pro Gly
    50                  55                  60

Thr Leu Glu Glu Lys Pro Leu Cys Glu Lys Thr Ala Ile Asn Asn Glu
65                  70                  75                  80

Tyr Asn Tyr Arg Cys Trp Thr Thr Asn Arg Cys Gln Lys Met Cys Pro
                85                  90                  95

-continued

```
Ser Ala Cys Gly Lys Arg Ala Cys Thr Glu Asn Asn Glu Cys Cys His
            100                 105                 110

Pro Glu Cys Leu Gly Ser Cys His Ala Pro Asp Asp Thr Ala Cys
        115                 120                 125

Val Ala Cys Arg His Tyr Tyr Phe Ser Gly Val Cys Val Pro Ala Cys
    130                 135                 140

Pro Pro Asn Thr Tyr Arg Phe Glu Gly Trp Arg Cys Val Asp Arg Asp
145                 150                 155                 160

Phe Cys Ala Asn Ile Pro Asn Ala Asp Gly Asp Ser Glu Gly Phe
                165                 170                 175

Val Ile His Asp Gly Glu Cys Met Gln Glu Cys Pro Ser Gly Phe Ile
            180                 185                 190

Arg Asn Gly Ser Gln Ser Met Phe Cys Ile Pro Cys Glu Gly Pro Cys
            195                 200                 205

Pro Lys Val Cys Glu Glu Asp Lys Lys Thr Lys Thr Ile Asp Ser Val
        210                 215                 220

Asn Ser Ala Gln Met Leu Gln Gly Cys Thr Ile Phe Lys Gly Asn
225                 230                 235

<210> SEQ ID NO 29
<211> LENGTH: 8
<212> TYPE: PRT
<213> ORGANISM: Artificial Sequence
<220> FEATURE:
<223> OTHER INFORMATION: FLAG tag

<400> SEQUENCE: 29

Asp Tyr Lys Asp Asp Asp Asp Lys
1               5

<210> SEQ ID NO 30
<211> LENGTH: 12
<212> TYPE: PRT
<213> ORGANISM: Homo sapiens

<400> SEQUENCE: 30

Pro Ser Gly Phe Ile Arg Asn Gly Ser Gln Ser Met
1               5                   10
```